(12) United States Patent
Schauer et al.

(10) Patent No.: US 11,707,431 B2
(45) Date of Patent: Jul. 25, 2023

(54) DENTAL STRIPS FOR THE DELIVERY OF SPECIFICALLY TARGETED ANTIMICROBIAL PEPTIDES

(71) Applicant: C3 Jian, LLC, Marina Del Rey, CA (US)

(72) Inventors: Evan Schauer, Los Angeles, CA (US); Miroslav Baudys, Marina Del Rey, CA (US); Brian C. Varnum, Santa Monica, CA (US); Duane Morris, Santa Monica, CA (US); Christopher W. Kaplan, Los Angeles, CA (US); Randal H. Eckert, Ellensburg, WA (US)

(73) Assignee: C3 Jian, LLC, Marina Del Rey, CA (US)

( * ) Notice: Subject to any disclaimer, the term of this patent is extended or adjusted under 35 U.S.C. 154(b) by 0 days.

(21) Appl. No.: 16/604,135

(22) PCT Filed: Apr. 12, 2018

(86) PCT No.: PCT/US2018/027357
§ 371 (c)(1),
(2) Date: Oct. 9, 2019

(87) PCT Pub. No.: WO2018/191533
PCT Pub. Date: Oct. 18, 2018

(65) Prior Publication Data
US 2020/0113818 A1    Apr. 16, 2020

Related U.S. Application Data

(60) Provisional application No. 62/485,793, filed on Apr. 14, 2017.

(51) Int. Cl.
| | | |
|---|---|---|
| A61K 9/00 | (2006.01) | |
| A61K 38/10 | (2006.01) | |
| A61K 38/16 | (2006.01) | |
| A61K 47/32 | (2006.01) | |
| A61K 47/34 | (2017.01) | |
| A61K 47/38 | (2006.01) | |

(52) U.S. Cl.
CPC .............. A61K 9/006 (2013.01); A61K 38/10 (2013.01); A61K 38/164 (2013.01); A61K 47/32 (2013.01); A61K 47/34 (2013.01); A61K 47/38 (2013.01)

(58) Field of Classification Search
None
See application file for complete search history.

(56) References Cited

U.S. PATENT DOCUMENTS

| | | | |
|---|---|---|---|
| 3,497,591 A | 2/1970 | Yankell et al. | |
| 5,330,746 A | 7/1994 | Friedman et al. | |
| 7,128,899 B2 * | 10/2006 | Chen | A61Q 11/02 424/53 |
| 7,846,895 B2 | 12/2010 | Eckert et al. | |
| 8,680,058 B2 | 3/2014 | Eckert et al. | |
| 9,351,490 B2 | 5/2016 | Eckert et al. | |
| 10,111,926 B2 | 10/2018 | Eckert et al. | |
| 2002/0176827 A1 * | 11/2002 | Rajaiah | A61K 8/8111 424/49 |
| 2005/0113510 A1 | 5/2005 | Feldstein et al. | |
| 2005/0175552 A1 | 8/2005 | Hoic et al. | |
| 2007/0003493 A1 | 1/2007 | Simonton et al. | |
| 2009/0191279 A1 | 7/2009 | Kennard et al. | |
| 2011/0039763 A1 | 2/2011 | Eckert et al. | |
| 2011/0244430 A1 | 10/2011 | Gibson et al. | |
| 2012/0039820 A1 | 2/2012 | Wagner-Doebler et al. | |
| 2014/0051036 A1 | 2/2014 | Wagner-Doebler et al. | |
| 2014/0162208 A1 | 6/2014 | Stookey et al. | |
| 2014/0248222 A1 | 9/2014 | Huo et al. | |
| 2014/0349917 A1 * | 11/2014 | Eckert | A61K 8/64 514/2.3 |
| 2015/0257983 A1 | 9/2015 | Lendenmann et al. | |
| 2016/0031941 A1 | 2/2016 | Eckert et al. | |

(Continued)

FOREIGN PATENT DOCUMENTS

| | | |
|---|---|---|
| WO | WO 2005/082407 A1 | 9/2005 |
| WO | WO 2008/030988 A2 | 3/2008 |

(Continued)

OTHER PUBLICATIONS

Eckert et al. "Targeted Killing of *Streptococcus mutans* by a Pheremone-Guided "Smart" Antimicrobial Peptide" Antimicrobial Agents and Chemotherapy 50:3651-3657. (Year: 2006).*
Mai et al. "A Novel Target-Specific, Salt-Resistant Antimicrobial Peptide against the Cariogenic Pathogen *Streptococcus mutans*" Antimicrobial Agents and Chemotherapy 55:5205-5213. (Year: 2011).*
Rogy et al. "A Phase 2 Study to Evaluate the Microbiology, Safety and Tolerability of C16G2 Dental Strip" ClinicalTrials.gov NCT03052842. (Year: 2017).*

(Continued)

*Primary Examiner* — Sudhakar Katakam
*Assistant Examiner* — Zachary J Miknis
(74) *Attorney, Agent, or Firm* — Tom Hunter; Weaver Austin Villeneuve & Sampson LLP

(57) ABSTRACT

In certain embodiments a dental strip for the prevention or reduction of dental caries is provided. In certain embodiments the dental strip is constructed to deliver effective amounts of specifically targeted antimicrobial peptides (or simple antimicrobial peptides) and comprises an orally compatible backing layer, a delivery layer disposed on one surface of the backing layer where the delivery layer comprises an orally compatible polymer, or combination of polymers, and a specifically targeted antimicrobial peptide (and/or simple antimicrobial peptide) capable of binding and killing *Streptococcus mutans*. In certain embodiments the dental strip additionally comprises a release liner.

14 Claims, 7 Drawing Sheets

Specification includes a Sequence Listing.

(56) References Cited

U.S. PATENT DOCUMENTS

| 2016/0303007 | A1 | 10/2016 | Blanvalet et al. |
| 2016/0368953 | A1 | 12/2016 | Renye, Jr. et al. |
| 2017/0027168 | A1 | 2/2017 | Heath |
| 2017/0135922 | A1 | 5/2017 | Yang et al. |
| 2020/0276103 | A1 | 9/2020 | Schauer et al. |

FOREIGN PATENT DOCUMENTS

| WO | WO 2010/091199 A2 | 8/2010 |
| WO | WO 2018/191529 A1 | 10/2018 |

OTHER PUBLICATIONS

Wei et al. "Effect of MUC7 peptides on the growth of bacteria and on *Streptococcus mutans* biofilm" J Antimicrobial Chemotherapy 57:1100-1109. (Year: 2006).*

PCT International Search Report and Written Opinion dated Jul. 26, 2018 issued in PCT/US2018/027350.
PCT International Preliminary Report on Patentability dated Oct. 15, 2019 issued in PCT/US2018/027350.
PCT International Search Report and Written Opinion dated Jul. 6, 2018 issued in PCT/US2018/027357.
PCT International Preliminary Report on Patentability dated Oct. 15, 2019 issued in PCT/US2018/027357.
U.S. Office Action [Restriction Requirement] dated Jun. 7, 2021 issued in U.S. Appl. No. 16/604,130.
U.S. Office Action dated Sep. 29, 2021 issued in U.S. Appl. No. 16/604,130.
EUDRAGIT® E 100, EUDRAGIT® E PO and EUDRAGIT® E 12,5 Technical Information (Jul. 2015) *Evonik Nutrition & Care GmbH* INFO 7.1/E [6 pages].
U.S. Final Office Action dated May 19, 2022, in U.S. Appl. No. 16/604,130.

* cited by examiner

SEQUENCE LISTING

<160> NUMBER OF SEQ ID NOS: 330

<210> SEQ ID NO 1
<211> LENGTH: 35
<212> TYPE: PRT
<213> ORGANISM: Artificial
<220> FEATURE:
<223> OTHER INFORMATION: Targeted antimicrobial peptide

<400> SEQUENCE: 1

Thr Phe Phe Arg Leu Phe Asn Arg Ser Phe Thr Gln Ala Leu Gly Lys
1               5                   10                  15

Gly Gly Gly Lys Asn Leu Arg Ile Ile Arg Lys Gly Ile His Ile Ile
            20                  25                  30

Lys Lys Tyr
        35

<210> SEQ ID NO 2
<211> LENGTH: 35
<212> TYPE: PRT
<213> ORGANISM: Artificial
<220> FEATURE:
<223> OTHER INFORMATION: Targeted antimicrobial peptide

<400> SEQUENCE: 2

Thr Phe Phe Arg Leu Phe Asn Arg Ser Phe Thr Gln Ala Leu Gly Lys
1               5                   10                  15

Gly Gly Gly Lys Asn Leu Arg Ile Ile Arg Lys Gly Ile His Ile Ile
            20                  25                  30

Lys Lys Tyr
        35

<210> SEQ ID NO 3
<211> LENGTH: 16
<212> TYPE: PRT
<213> ORGANISM: Artificial
<220> FEATURE:
<223> OTHER INFORMATION: Competence stimulating peptide

<400> SEQUENCE: 3

Thr Phe Phe Arg Leu Phe Asn Arg Ser Phe Thr Gln Ala Leu Gly Lys
1               5                   10                  15

<210> SEQ ID NO 4
<211> LENGTH: 15
<212> TYPE: PRT
<213> ORGANISM: Artificial
<220> FEATURE:
<223> OTHER INFORMATION: Antimicrobial peptide

<400> SEQUENCE: 4

Lys Asn Leu Arg Ile Ile Arg Lys Gly Ile His Ile Ile Lys Lys
1               5                   10                  15

<210> SEQ ID NO 5
<211> LENGTH: 21
<212> TYPE: PRT
<213> ORGANISM: Artificial
<220> FEATURE:
<223> OTHER INFORMATION: Competence stimulating peptide

<400> SEQUENCE: 5

Ser Gly Ser Leu Ser Thr Phe Phe Arg Leu Phe Asn Arg Ser Phe Thr
1               5                   10                  15

```
Gln Ala Leu Gly Lys
            20

<210> SEQ ID NO 6
<211> LENGTH: 17
<212> TYPE: PRT
<213> ORGANISM: Artificial
<220> FEATURE:
<223> OTHER INFORMATION: Competence stimulating peptide

<400> SEQUENCE: 6

Glu Met Arg Leu Ser Lys Phe Phe Arg Asp Phe Ile Leu Gln Arg Lys
1               5                   10                  15

Lys

<210> SEQ ID NO 7
<211> LENGTH: 17
<212> TYPE: PRT
<213> ORGANISM: Artificial
<220> FEATURE:
<223> OTHER INFORMATION: Competence stimulating peptide

<400> SEQUENCE: 7

Glu Met Arg Ile Ser Arg Ile Ile Leu Asp Phe Leu Phe Leu Arg Lys
1               5                   10                  15

Lys

<210> SEQ ID NO 8
<211> LENGTH: 8
<212> TYPE: PRT
<213> ORGANISM: Artificial
<220> FEATURE:
<223> OTHER INFORMATION: Competence stimulating peptide

<400> SEQUENCE: 8

Asn Ile Phe Glu Tyr Phe Leu Glu
1               5

<210> SEQ ID NO 9
<211> LENGTH: 8
<212> TYPE: PRT
<213> ORGANISM: Artificial
<220> FEATURE:
<223> OTHER INFORMATION: Competence stimulating peptide fragment

<400> SEQUENCE: 9

Thr Phe Phe Arg Leu Phe Asn Arg
1               5

<210> SEQ ID NO 10
<211> LENGTH: 9
<212> TYPE: PRT
<213> ORGANISM: Artificial
<220> FEATURE:
<223> OTHER INFORMATION: Competence stimulating peptide fragment

<400> SEQUENCE: 10

Thr Phe Phe Arg Leu Phe Asn Arg Ser
1               5

<210> SEQ ID NO 11
<211> LENGTH: 9
<212> TYPE: PRT
<213> ORGANISM: Artificial
<220> FEATURE:
<223> OTHER INFORMATION: Competence stimulating peptide fragment
```

<400> SEQUENCE: 11

Thr Phe Phe Arg Leu Phe Asn Arg Ser
1               5

<210> SEQ ID NO 12
<211> LENGTH: 10
<212> TYPE: PRT
<213> ORGANISM: Artificial
<220> FEATURE:
<223> OTHER INFORMATION: Competence stimulating peptide fragment

<400> SEQUENCE: 12

Thr Phe Phe Arg Leu Phe Asn Arg Ser Phe
1               5                   10

<210> SEQ ID NO 13
<211> LENGTH: 11
<212> TYPE: PRT
<213> ORGANISM: Artificial
<220> FEATURE:
<223> OTHER INFORMATION: Competence stimulating peptide fragment

<400> SEQUENCE: 13

Thr Phe Phe Arg Leu Phe Asn Arg Ser Phe Thr
1               5                   10

<210> SEQ ID NO 14
<211> LENGTH: 12
<212> TYPE: PRT
<213> ORGANISM: Artificial
<220> FEATURE:
<223> OTHER INFORMATION: Competence stimulating peptide fragment

<400> SEQUENCE: 14

Thr Phe Phe Arg Leu Phe Asn Arg Ser Phe Thr Gln
1               5                   10

<210> SEQ ID NO 15
<211> LENGTH: 13
<212> TYPE: PRT
<213> ORGANISM: Artificial
<220> FEATURE:
<223> OTHER INFORMATION: Competence stimulating peptide fragment

<400> SEQUENCE: 15

Thr Phe Phe Arg Leu Phe Asn Arg Ser Phe Thr Gln Ala
1               5                   10

<210> SEQ ID NO 16
<211> LENGTH: 14
<212> TYPE: PRT
<213> ORGANISM: Artificial
<220> FEATURE:
<223> OTHER INFORMATION: Competence stimulating peptide fragment

<400> SEQUENCE: 16

Thr Phe Phe Arg Leu Phe Asn Arg Ser Phe Thr Gln Ala Leu
1               5                   10

<210> SEQ ID NO 17
<211> LENGTH: 15
<212> TYPE: PRT
<213> ORGANISM: Artificial
<220> FEATURE:
<223> OTHER INFORMATION: Competence stimulating peptide fragment

```
<400> SEQUENCE: 17

Thr Phe Phe Arg Leu Phe Asn Arg Ser Phe Thr Gln Ala Leu Gly
1               5                   10                  15

<210> SEQ ID NO 18
<211> LENGTH: 16
<212> TYPE: PRT
<213> ORGANISM: Artificial
<220> FEATURE:
<223> OTHER INFORMATION: Competence stimulating peptide fragment

<400> SEQUENCE: 18

Thr Phe Phe Arg Leu Phe Asn Arg Ser Phe Thr Gln Ala Leu Gly Lys
1               5                   10                  15

<210> SEQ ID NO 19
<211> LENGTH: 9
<212> TYPE: PRT
<213> ORGANISM: Artificial
<220> FEATURE:
<223> OTHER INFORMATION: Competence stimulating peptide fragment

<400> SEQUENCE: 19

Ser Thr Phe Phe Arg Leu Phe Asn Arg
1               5

<210> SEQ ID NO 20
<211> LENGTH: 10
<212> TYPE: PRT
<213> ORGANISM: Artificial
<220> FEATURE:
<223> OTHER INFORMATION: Competence stimulating peptide fragment

<400> SEQUENCE: 20

Ser Thr Phe Phe Arg Leu Phe Asn Arg Ser
1               5                   10

<210> SEQ ID NO 21
<211> LENGTH: 10
<212> TYPE: PRT
<213> ORGANISM: Artificial
<220> FEATURE:
<223> OTHER INFORMATION: Competence stimulating peptide fragment

<400> SEQUENCE: 21

Ser Thr Phe Phe Arg Leu Phe Asn Arg Ser
1               5                   10

<210> SEQ ID NO 22
<211> LENGTH: 11
<212> TYPE: PRT
<213> ORGANISM: Artificial
<220> FEATURE:
<223> OTHER INFORMATION: Competence stimulating peptide fragment

<400> SEQUENCE: 22

Ser Thr Phe Phe Arg Leu Phe Asn Arg Ser Phe
1               5                   10

<210> SEQ ID NO 23
<211> LENGTH: 12
<212> TYPE: PRT
<213> ORGANISM: Artificial
<220> FEATURE:
<223> OTHER INFORMATION: Competence stimulating peptide fragment

<400> SEQUENCE: 23
```

Ser Thr Phe Phe Arg Leu Phe Asn Arg Ser Phe Thr
1               5                   10

<210> SEQ ID NO 24
<211> LENGTH: 13
<212> TYPE: PRT
<213> ORGANISM: Artificial
<220> FEATURE:
<223> OTHER INFORMATION: Competence stimulating peptide fragment

<400> SEQUENCE: 24

Ser Thr Phe Phe Arg Leu Phe Asn Arg Ser Phe Thr Gln
1               5                   10

<210> SEQ ID NO 25
<211> LENGTH: 14
<212> TYPE: PRT
<213> ORGANISM: Artificial
<220> FEATURE:
<223> OTHER INFORMATION: Competence stimulating peptide fragment

<400> SEQUENCE: 25

Ser Thr Phe Phe Arg Leu Phe Asn Arg Ser Phe Thr Gln Ala
1               5                   10

<210> SEQ ID NO 26
<211> LENGTH: 15
<212> TYPE: PRT
<213> ORGANISM: Artificial
<220> FEATURE:
<223> OTHER INFORMATION: Competence stimulating peptide fragment

<400> SEQUENCE: 26

Ser Thr Phe Phe Arg Leu Phe Asn Arg Ser Phe Thr Gln Ala Leu
1               5                   10                  15

<210> SEQ ID NO 27
<211> LENGTH: 16
<212> TYPE: PRT
<213> ORGANISM: Artificial
<220> FEATURE:
<223> OTHER INFORMATION: Competence stimulating peptide fragment

<400> SEQUENCE: 27

Ser Thr Phe Phe Arg Leu Phe Asn Arg Ser Phe Thr Gln Ala Leu Gly
1               5                   10                  15

<210> SEQ ID NO 28
<211> LENGTH: 17
<212> TYPE: PRT
<213> ORGANISM: Artificial
<220> FEATURE:
<223> OTHER INFORMATION: Competence stimulating peptide fragment

<400> SEQUENCE: 28

Ser Thr Phe Phe Arg Leu Phe Asn Arg Ser Phe Thr Gln Ala Leu Gly
1               5                   10                  15

Lys

<210> SEQ ID NO 29
<211> LENGTH: 10
<212> TYPE: PRT
<213> ORGANISM: Artificial
<220> FEATURE:
<223> OTHER INFORMATION: Competence stimulating peptide fragment

```
<400> SEQUENCE: 29

Leu Ser Thr Phe Phe Arg Leu Phe Asn Arg
1               5                   10

<210> SEQ ID NO 30
<211> LENGTH: 11
<212> TYPE: PRT
<213> ORGANISM: Artificial
<220> FEATURE:
<223> OTHER INFORMATION: Competence stimulating peptide fragment

<400> SEQUENCE: 30

Leu Ser Thr Phe Phe Arg Leu Phe Asn Arg Ser
1               5                   10

<210> SEQ ID NO 31
<211> LENGTH: 11
<212> TYPE: PRT
<213> ORGANISM: Artificial
<220> FEATURE:
<223> OTHER INFORMATION: Competence stimulating peptide fragment

<400> SEQUENCE: 31

Leu Ser Thr Phe Phe Arg Leu Phe Asn Arg Ser
1               5                   10

<210> SEQ ID NO 32
<211> LENGTH: 12
<212> TYPE: PRT
<213> ORGANISM: Artificial
<220> FEATURE:
<223> OTHER INFORMATION: Competence stimulating peptide fragment

<400> SEQUENCE: 32

Leu Ser Thr Phe Phe Arg Leu Phe Asn Arg Ser Phe
1               5                   10

<210> SEQ ID NO 33
<211> LENGTH: 13
<212> TYPE: PRT
<213> ORGANISM: Artificial
<220> FEATURE:
<223> OTHER INFORMATION: Competence stimulating peptide fragment

<400> SEQUENCE: 33

Leu Ser Thr Phe Phe Arg Leu Phe Asn Arg Ser Phe Thr
1               5                   10

<210> SEQ ID NO 34
<211> LENGTH: 14
<212> TYPE: PRT
<213> ORGANISM: Artificial
<220> FEATURE:
<223> OTHER INFORMATION: Competence stimulating peptide fragment

<400> SEQUENCE: 34

Leu Ser Thr Phe Phe Arg Leu Phe Asn Arg Ser Phe Thr Gln
1               5                   10

<210> SEQ ID NO 35
<211> LENGTH: 15
<212> TYPE: PRT
<213> ORGANISM: Artificial
<220> FEATURE:
<223> OTHER INFORMATION: Competence stimulating peptide fragment

<400> SEQUENCE: 35
```

```
Leu Ser Thr Phe Phe Arg Leu Phe Asn Arg Ser Phe Thr Gln Ala
1               5                   10                  15

<210> SEQ ID NO 36
<211> LENGTH: 16
<212> TYPE: PRT
<213> ORGANISM: Artificial
<220> FEATURE:
<223> OTHER INFORMATION: Competence stimulating peptide fragment

<400> SEQUENCE: 36

Leu Ser Thr Phe Phe Arg Leu Phe Asn Arg Ser Phe Thr Gln Ala Leu
1               5                   10                  15

<210> SEQ ID NO 37
<211> LENGTH: 17
<212> TYPE: PRT
<213> ORGANISM: Artificial
<220> FEATURE:
<223> OTHER INFORMATION: Competence stimulating peptide fragment

<400> SEQUENCE: 37

Leu Ser Thr Phe Phe Arg Leu Phe Asn Arg Ser Phe Thr Gln Ala Leu
1               5                   10                  15

Gly

<210> SEQ ID NO 38
<211> LENGTH: 18
<212> TYPE: PRT
<213> ORGANISM: Artificial
<220> FEATURE:
<223> OTHER INFORMATION: Competence stimulating peptide fragment

<400> SEQUENCE: 38

Leu Ser Thr Phe Phe Arg Leu Phe Asn Arg Ser Phe Thr Gln Ala Leu
1               5                   10                  15

Gly Lys

<210> SEQ ID NO 39
<211> LENGTH: 11
<212> TYPE: PRT
<213> ORGANISM: Artificial
<220> FEATURE:
<223> OTHER INFORMATION: Competence stimulating peptide fragment

<400> SEQUENCE: 39

Ser Leu Ser Thr Phe Phe Arg Leu Phe Asn Arg
1               5                   10

<210> SEQ ID NO 40
<211> LENGTH: 12
<212> TYPE: PRT
<213> ORGANISM: Artificial
<220> FEATURE:
<223> OTHER INFORMATION: Competence stimulating peptide fragment

<400> SEQUENCE: 40

Ser Leu Ser Thr Phe Phe Arg Leu Phe Asn Arg Ser
1               5                   10

<210> SEQ ID NO 41
<211> LENGTH: 12
<212> TYPE: PRT
<213> ORGANISM: Artificial
<220> FEATURE:
```

<223> OTHER INFORMATION: Competence stimulating peptide fragment

<400> SEQUENCE: 41

Ser Leu Ser Thr Phe Phe Arg Leu Phe Asn Arg Ser
1               5                   10

<210> SEQ ID NO 42
<211> LENGTH: 13
<212> TYPE: PRT
<213> ORGANISM: Artificial
<220> FEATURE:
<223> OTHER INFORMATION: Competence stimulating peptide fragment

<400> SEQUENCE: 42

Ser Leu Ser Thr Phe Phe Arg Leu Phe Asn Arg Ser Phe
1               5                   10

<210> SEQ ID NO 43
<211> LENGTH: 14
<212> TYPE: PRT
<213> ORGANISM: Artificial
<220> FEATURE:
<223> OTHER INFORMATION: Competence stimulating peptide fragment

<400> SEQUENCE: 43

Ser Leu Ser Thr Phe Phe Arg Leu Phe Asn Arg Ser Phe Thr
1               5                   10

<210> SEQ ID NO 44
<211> LENGTH: 15
<212> TYPE: PRT
<213> ORGANISM: Artificial
<220> FEATURE:
<223> OTHER INFORMATION: Competence stimulating peptide fragment

<400> SEQUENCE: 44

Ser Leu Ser Thr Phe Phe Arg Leu Phe Asn Arg Ser Phe Thr Gln
1               5                   10                  15

<210> SEQ ID NO 45
<211> LENGTH: 16
<212> TYPE: PRT
<213> ORGANISM: Artificial
<220> FEATURE:
<223> OTHER INFORMATION: Competence stimulating peptide fragment

<400> SEQUENCE: 45

Ser Leu Ser Thr Phe Phe Arg Leu Phe Asn Arg Ser Phe Thr Gln Ala
1               5                   10                  15

<210> SEQ ID NO 46
<211> LENGTH: 17
<212> TYPE: PRT
<213> ORGANISM: Artificial
<220> FEATURE:
<223> OTHER INFORMATION: Competence stimulating peptide fragment

<400> SEQUENCE: 46

Ser Leu Ser Thr Phe Phe Arg Leu Phe Asn Arg Ser Phe Thr Gln Ala
1               5                   10                  15

Leu

<210> SEQ ID NO 47
<211> LENGTH: 18
<212> TYPE: PRT
<213> ORGANISM: Artificial

```
<220> FEATURE:
<223> OTHER INFORMATION: Competence stimulating peptide fragment

<400> SEQUENCE: 47

Ser Leu Ser Thr Phe Phe Arg Leu Phe Asn Arg Ser Phe Thr Gln Ala
1               5                   10                  15

Leu Gly

<210> SEQ ID NO 48
<211> LENGTH: 19
<212> TYPE: PRT
<213> ORGANISM: Artificial
<220> FEATURE:
<223> OTHER INFORMATION: Competence stimulating peptide fragment

<400> SEQUENCE: 48

Ser Leu Ser Thr Phe Phe Arg Leu Phe Asn Arg Ser Phe Thr Gln Ala
1               5                   10                  15

Leu Gly Lys

<210> SEQ ID NO 49
<211> LENGTH: 12
<212> TYPE: PRT
<213> ORGANISM: Artificial
<220> FEATURE:
<223> OTHER INFORMATION: Competence stimulating peptide fragment

<400> SEQUENCE: 49

Gly Ser Leu Ser Thr Phe Phe Arg Leu Phe Asn Arg
1               5                   10

<210> SEQ ID NO 50
<211> LENGTH: 13
<212> TYPE: PRT
<213> ORGANISM: Artificial
<220> FEATURE:
<223> OTHER INFORMATION: Competence stimulating peptide fragment

<400> SEQUENCE: 50

Gly Ser Leu Ser Thr Phe Phe Arg Leu Phe Asn Arg Ser
1               5                   10

<210> SEQ ID NO 51
<211> LENGTH: 13
<212> TYPE: PRT
<213> ORGANISM: Artificial
<220> FEATURE:
<223> OTHER INFORMATION: Competence stimulating peptide fragment

<400> SEQUENCE: 51

Gly Ser Leu Ser Thr Phe Phe Arg Leu Phe Asn Arg Ser
1               5                   10

<210> SEQ ID NO 52
<211> LENGTH: 14
<212> TYPE: PRT
<213> ORGANISM: Artificial
<220> FEATURE:
<223> OTHER INFORMATION: Competence stimulating peptide fragment

<400> SEQUENCE: 52

Gly Ser Leu Ser Thr Phe Phe Arg Leu Phe Asn Arg Ser Phe
1               5                   10

<210> SEQ ID NO 53
```

```
<211> LENGTH: 15
<212> TYPE: PRT
<213> ORGANISM: Artificial
<220> FEATURE:
<223> OTHER INFORMATION: Competence stimulating peptide fragment

<400> SEQUENCE: 53

Gly Ser Leu Ser Thr Phe Phe Arg Leu Phe Asn Arg Ser Phe Thr
1               5                   10                  15

<210> SEQ ID NO 54
<211> LENGTH: 16
<212> TYPE: PRT
<213> ORGANISM: Artificial
<220> FEATURE:
<223> OTHER INFORMATION: Competence stimulating peptide fragment

<400> SEQUENCE: 54

Gly Ser Leu Ser Thr Phe Phe Arg Leu Phe Asn Arg Ser Phe Thr Gln
1               5                   10                  15

<210> SEQ ID NO 55
<211> LENGTH: 17
<212> TYPE: PRT
<213> ORGANISM: Artificial
<220> FEATURE:
<223> OTHER INFORMATION: Competence stimulating peptide fragment

<400> SEQUENCE: 55

Gly Ser Leu Ser Thr Phe Phe Arg Leu Phe Asn Arg Ser Phe Thr Gln
1               5                   10                  15

Ala

<210> SEQ ID NO 56
<211> LENGTH: 18
<212> TYPE: PRT
<213> ORGANISM: Artificial
<220> FEATURE:
<223> OTHER INFORMATION: Competence stimulating peptide fragment

<400> SEQUENCE: 56

Gly Ser Leu Ser Thr Phe Phe Arg Leu Phe Asn Arg Ser Phe Thr Gln
1               5                   10                  15

Ala Leu

<210> SEQ ID NO 57
<211> LENGTH: 19
<212> TYPE: PRT
<213> ORGANISM: Artificial
<220> FEATURE:
<223> OTHER INFORMATION: Competence stimulating peptide fragment

<400> SEQUENCE: 57

Gly Ser Leu Ser Thr Phe Phe Arg Leu Phe Asn Arg Ser Phe Thr Gln
1               5                   10                  15

Ala Leu Gly

<210> SEQ ID NO 58
<211> LENGTH: 20
<212> TYPE: PRT
<213> ORGANISM: Artificial
<220> FEATURE:
<223> OTHER INFORMATION: Competence stimulating peptide fragment

<400> SEQUENCE: 58
```

Gly Ser Leu Ser Thr Phe Phe Arg Leu Phe Asn Arg Ser Phe Thr Gln
1               5                   10                  15

Ala Leu Gly Lys
            20

<210> SEQ ID NO 59
<211> LENGTH: 13
<212> TYPE: PRT
<213> ORGANISM: Artificial
<220> FEATURE:
<223> OTHER INFORMATION: Competence stimulating peptide fragment

<400> SEQUENCE: 59

Ser Gly Ser Leu Ser Thr Phe Phe Arg Leu Phe Asn Arg
1               5                   10

<210> SEQ ID NO 60
<211> LENGTH: 14
<212> TYPE: PRT
<213> ORGANISM: Artificial
<220> FEATURE:
<223> OTHER INFORMATION: Competence stimulating peptide fragment

<400> SEQUENCE: 60

Ser Gly Ser Leu Ser Thr Phe Phe Arg Leu Phe Asn Arg Ser
1               5                   10

<210> SEQ ID NO 61
<211> LENGTH: 14
<212> TYPE: PRT
<213> ORGANISM: Artificial
<220> FEATURE:
<223> OTHER INFORMATION: Competence stimulating peptide fragment

<400> SEQUENCE: 61

Ser Gly Ser Leu Ser Thr Phe Phe Arg Leu Phe Asn Arg Ser
1               5                   10

<210> SEQ ID NO 62
<211> LENGTH: 15
<212> TYPE: PRT
<213> ORGANISM: Artificial
<220> FEATURE:
<223> OTHER INFORMATION: Competence stimulating peptide fragment

<400> SEQUENCE: 62

Ser Gly Ser Leu Ser Thr Phe Phe Arg Leu Phe Asn Arg Ser Phe
1               5                   10                  15

<210> SEQ ID NO 63
<211> LENGTH: 16
<212> TYPE: PRT
<213> ORGANISM: Artificial
<220> FEATURE:
<223> OTHER INFORMATION: Competence stimulating peptide fragment

<400> SEQUENCE: 63

Ser Gly Ser Leu Ser Thr Phe Phe Arg Leu Phe Asn Arg Ser Phe Thr
1               5                   10                  15

<210> SEQ ID NO 64
<211> LENGTH: 17
<212> TYPE: PRT
<213> ORGANISM: Artificial
<220> FEATURE:
<223> OTHER INFORMATION: Competence stimulating peptide fragment -continued

```
<400> SEQUENCE: 64

Ser Gly Ser Leu Ser Thr Phe Phe Arg Leu Phe Asn Arg Ser Phe Thr
1               5                   10                  15

Gln

<210> SEQ ID NO 65
<211> LENGTH: 18
<212> TYPE: PRT
<213> ORGANISM: Artificial
<220> FEATURE:
<223> OTHER INFORMATION: Competence stimulating peptide fragment

<400> SEQUENCE: 65

Ser Gly Ser Leu Ser Thr Phe Phe Arg Leu Phe Asn Arg Ser Phe Thr
1               5                   10                  15

Gln Ala

<210> SEQ ID NO 66
<211> LENGTH: 19
<212> TYPE: PRT
<213> ORGANISM: Artificial
<220> FEATURE:
<223> OTHER INFORMATION: Competence stimulating peptide fragment

<400> SEQUENCE: 66

Ser Gly Ser Leu Ser Thr Phe Phe Arg Leu Phe Asn Arg Ser Phe Thr
1               5                   10                  15

Gln Ala Leu

<210> SEQ ID NO 67
<211> LENGTH: 20
<212> TYPE: PRT
<213> ORGANISM: Artificial
<220> FEATURE:
<223> OTHER INFORMATION: Competence stimulating peptide fragment

<400> SEQUENCE: 67

Ser Gly Ser Leu Ser Thr Phe Phe Arg Leu Phe Asn Arg Ser Phe Thr
1               5                   10                  15

Gln Ala Leu Gly
            20

<210> SEQ ID NO 68
<211> LENGTH: 16
<212> TYPE: PRT
<213> ORGANISM: Artificial
<220> FEATURE:
<223> OTHER INFORMATION: Generic targeting peptide
<220> FEATURE:
<221> NAME/KEY: misc_feature
<222> LOCATION: (1)..(1)
<223> OTHER INFORMATION: Xaa is a polar amino acid or A
<220> FEATURE:
<221> NAME/KEY: misc_feature
<222> LOCATION: (2)..(2)
<223> OTHER INFORMATION: Xaa is F, W, Q, A, or an analog thereof
<220> FEATURE:
<221> NAME/KEY: misc_feature
<222> LOCATION: (5)..(5)
<223> OTHER INFORMATION: Xaa is a hydrophobic amino acid
<220> FEATURE:
<221> NAME/KEY: misc_feature
<222> LOCATION: (6)..(6)
<223> OTHER INFORMATION: Xaa is a hydrophobic amino acid, N, Q, or an
      analog thereof
<220> FEATURE:
<221> NAME/KEY: misc_feature
```

```
<222> LOCATION: (7)..(7)
<223> OTHER INFORMATION: Xaa is a polar amino acid, A, F, or an analog
      thereof
<220> FEATURE:
<221> NAME/KEY: misc_feature
<222> LOCATION: (9)..(9)
<223> OTHER INFORMATION: Xaa is a polar amino acid, A or an analog
      thereof
<220> FEATURE:
<221> NAME/KEY: misc_feature
<222> LOCATION: (10)..(10)
<223> OTHER INFORMATION: Xaa is a hydrophobic amino acid, Q, A, or an
      analog thereof
<220> FEATURE:
<221> NAME/KEY: misc_feature
<222> LOCATION: (11)..(11)
<223> OTHER INFORMATION: Xaa is a hydrophobic amino acid
<220> FEATURE:
<221> NAME/KEY: misc_feature
<222> LOCATION: (12)..(12)
<223> OTHER INFORMATION: Xaa is Q, A, or an analog thereof
<220> FEATURE:
<221> NAME/KEY: misc_feature
<222> LOCATION: (13)..(13)
<223> OTHER INFORMATION: Xaa is a non-polar amino acid
<220> FEATURE:
<221> NAME/KEY: misc_feature
<222> LOCATION: (14)..(14)
<223> OTHER INFORMATION: Xaa is a hydrophobic amino acid
<220> FEATURE:
<221> NAME/KEY: misc_feature
<222> LOCATION: (15)..(15)
<223> OTHER INFORMATION: Xaa is a non-polar amino acid, N, S, D, or an
      analog thereof
<220> FEATURE:
<221> NAME/KEY: misc_feature
<222> LOCATION: (16)..(16)
<223> OTHER INFORMATION: Xaa is a polar amino acid, F, A, or an analog
      thereof

<400> SEQUENCE: 68

Xaa Xaa Phe Arg Xaa Xaa Xaa Arg Xaa Xaa Xaa Xaa Xaa Xaa Xaa Xaa
1               5                   10                  15

<210> SEQ ID NO 69
<211> LENGTH: 16
<212> TYPE: PRT
<213> ORGANISM: Artificial
<220> FEATURE:
<223> OTHER INFORMATION: Targeting peptide

<400> SEQUENCE: 69

Thr Phe Phe Arg Leu Phe Asn Arg Ser Phe Thr Gln Ala Leu Gly Lys
1               5                   10                  15

<210> SEQ ID NO 70
<211> LENGTH: 16
<212> TYPE: PRT
<213> ORGANISM: Artificial
<220> FEATURE:
<223> OTHER INFORMATION: S. mutans targeting peptide

<400> SEQUENCE: 70

Ala Phe Phe Arg Ala Phe Asn Arg Ala Phe Ala Gln Ala Leu Ala Lys
1               5                   10                  15

<210> SEQ ID NO 71
<211> LENGTH: 16
<212> TYPE: PRT
<213> ORGANISM: Artificial
<220> FEATURE:
<223> OTHER INFORMATION: S. mutans targeting peptide
```

<400> SEQUENCE: 71

Thr Phe Phe Arg Ala Phe Ala Arg Ala Phe Ala Gln Ala Ala Ala Lys
1               5                   10                  15

<210> SEQ ID NO 72
<211> LENGTH: 16
<212> TYPE: PRT
<213> ORGANISM: Artificial
<220> FEATURE:
<223> OTHER INFORMATION: S. mutans targeting peptide

<400> SEQUENCE: 72

Ala Phe Phe Arg Ala Phe Ala Arg Ala Phe Ala Gln Ala Leu Ala Lys
1               5                   10                  15

<210> SEQ ID NO 73
<211> LENGTH: 16
<212> TYPE: PRT
<213> ORGANISM: Artificial
<220> FEATURE:
<223> OTHER INFORMATION: S. mutans targeting peptide

<400> SEQUENCE: 73

Ala Phe Phe Arg Leu Phe Ala Arg Ala Phe Ala Gln Ala Ala Ala Lys
1               5                   10                  15

<210> SEQ ID NO 74
<211> LENGTH: 16
<212> TYPE: PRT
<213> ORGANISM: Artificial
<220> FEATURE:
<223> OTHER INFORMATION: S. mutans targeting peptide

<400> SEQUENCE: 74

Thr Leu Phe Arg Leu Leu Asn Arg Ser Leu Thr Gln Ala Leu Gly Lys
1               5                   10                  15

<210> SEQ ID NO 75
<211> LENGTH: 16
<212> TYPE: PRT
<213> ORGANISM: Artificial
<220> FEATURE:
<223> OTHER INFORMATION: S. mutans targeting peptide

<400> SEQUENCE: 75

Thr Phe Phe Arg Leu Phe Asn Arg Ser Phe Thr Gln Ala Leu Phe Lys
1               5                   10                  15

<210> SEQ ID NO 76
<211> LENGTH: 16
<212> TYPE: PRT
<213> ORGANISM: Artificial
<220> FEATURE:
<223> OTHER INFORMATION: S. mutans targeting peptide

<400> SEQUENCE: 76

Thr Phe Phe Arg Leu Phe Asn Arg Ser Leu Thr Gln Ala Leu Gly Lys
1               5                   10                  15

<210> SEQ ID NO 77
<211> LENGTH: 16
<212> TYPE: PRT
<213> ORGANISM: Artificial
<220> FEATURE:
<223> OTHER INFORMATION: S. mutans targeting peptide

<400> SEQUENCE: 77

Thr Phe Phe Arg Leu Phe Asn Arg Ser Phe Thr Gln Ala Leu Asn Lys
1               5                   10                  15

<210> SEQ ID NO 78
<211> LENGTH: 16
<212> TYPE: PRT
<213> ORGANISM: Artificial
<220> FEATURE:
<223> OTHER INFORMATION: S. mutans targeting peptide

<400> SEQUENCE: 78

Ala Phe Phe Arg Ala Phe Ala Arg Ala Phe Ala Gln Ala Ala Ala Lys
1               5                   10                  15

<210> SEQ ID NO 79
<211> LENGTH: 16
<212> TYPE: PRT
<213> ORGANISM: Artificial
<220> FEATURE:
<223> OTHER INFORMATION: S. mutans targeting peptide

<400> SEQUENCE: 79

Ala Phe Phe Arg Ala Phe Asn Arg Ala Phe Ala Gln Ala Ala Ala Lys
1               5                   10                  15

<210> SEQ ID NO 80
<211> LENGTH: 16
<212> TYPE: PRT
<213> ORGANISM: Artificial
<220> FEATURE:
<223> OTHER INFORMATION: S. mutans targeting peptide

<400> SEQUENCE: 80

Thr Phe Phe Arg Leu Phe Asn Arg Ser Phe Thr Gln Ala Leu Ser Lys
1               5                   10                  15

<210> SEQ ID NO 81
<211> LENGTH: 16
<212> TYPE: PRT
<213> ORGANISM: Artificial
<220> FEATURE:
<223> OTHER INFORMATION: S. mutans targeting peptide

<400> SEQUENCE: 81

Ala Phe Phe Arg Ala Phe Ala Arg Ser Phe Ala Gln Ala Ala Ala Lys
1               5                   10                  15

<210> SEQ ID NO 82
<211> LENGTH: 16
<212> TYPE: PRT
<213> ORGANISM: Artificial
<220> FEATURE:
<223> OTHER INFORMATION: S. mutans targeting peptide

<400> SEQUENCE: 82

Ala Phe Phe Arg Ala Phe Ala Arg Ala Phe Ala Gln Ala Ala Gly Lys
1               5                   10                  15

<210> SEQ ID NO 83
<211> LENGTH: 16
<212> TYPE: PRT
<213> ORGANISM: Artificial
<220> FEATURE:
<223> OTHER INFORMATION: S. mutans targeting peptide

<400> SEQUENCE: 83

Ala Phe Phe Arg Ala Phe Ala Arg Ala Phe Thr Gln Ala Ala Lys
1               5                   10                  15

<210> SEQ ID NO 84
<211> LENGTH: 16
<212> TYPE: PRT
<213> ORGANISM: Artificial
<220> FEATURE:
<223> OTHER INFORMATION: S. mutans targeting peptide

<400> SEQUENCE: 84

Thr Phe Phe Arg Leu Phe Asn Arg Ser Phe Thr Gln Ala Leu Gly Gln
1               5                   10                  15

<210> SEQ ID NO 85
<211> LENGTH: 16
<212> TYPE: PRT
<213> ORGANISM: Artificial
<220> FEATURE:
<223> OTHER INFORMATION: S. mutans targeting peptide

<400> SEQUENCE: 85

Thr Phe Phe Arg Leu Leu Asn Arg Ser Phe Thr Gln Ala Leu Gly Lys
1               5                   10                  15

<210> SEQ ID NO 86
<211> LENGTH: 16
<212> TYPE: PRT
<213> ORGANISM: Artificial
<220> FEATURE:
<223> OTHER INFORMATION: S. mutans targeting peptide

<400> SEQUENCE: 86

Thr Trp Phe Arg Leu Phe Asn Arg Ser Phe Thr Gln Ala Leu Gly Lys
1               5                   10                  15

<210> SEQ ID NO 87
<211> LENGTH: 16
<212> TYPE: PRT
<213> ORGANISM: Artificial
<220> FEATURE:
<223> OTHER INFORMATION: S. mutans targeting peptide

<400> SEQUENCE: 87

Ala Phe Phe Arg Ala Phe Ala Arg Ala Phe Ala Gln Ala Phe Ala Lys
1               5                   10                  15

<210> SEQ ID NO 88
<211> LENGTH: 16
<212> TYPE: PRT
<213> ORGANISM: Artificial
<220> FEATURE:
<223> OTHER INFORMATION: S. mutans targeting peptide

<400> SEQUENCE: 88

Thr Gln Phe Arg Leu Phe Asn Arg Ser Phe Thr Gln Ala Leu Gly Lys
1               5                   10                  15

<210> SEQ ID NO 89
<211> LENGTH: 16
<212> TYPE: PRT
<213> ORGANISM: Artificial
<220> FEATURE:
<223> OTHER INFORMATION: S. mutans targeting peptide

<400> SEQUENCE: 89

Thr Phe Phe Arg Leu Phe Asn Arg Ser Phe Thr Gln Ala Leu Asp Lys

```
1               5                   10                  15
```

<210> SEQ ID NO 90
<211> LENGTH: 16
<212> TYPE: PRT
<213> ORGANISM: Artificial
<220> FEATURE:
<223> OTHER INFORMATION: S. mutans targeting peptide

<400> SEQUENCE: 90

```
Thr Phe Phe Arg Leu Phe Asn Arg Ser Phe Thr Gln Ala Leu Ala Lys
1               5                   10                  15
```

<210> SEQ ID NO 91
<211> LENGTH: 16
<212> TYPE: PRT
<213> ORGANISM: Artificial
<220> FEATURE:
<223> OTHER INFORMATION: S. mutans targeting peptide

<400> SEQUENCE: 91

```
Thr Phe Phe Arg Leu Phe Asn Arg Ser Phe Thr Gln Ala Leu Gly Glu
1               5                   10                  15
```

<210> SEQ ID NO 92
<211> LENGTH: 16
<212> TYPE: PRT
<213> ORGANISM: Artificial
<220> FEATURE:
<223> OTHER INFORMATION: S. mutans targeting peptide

<400> SEQUENCE: 92

```
Thr Phe Phe Arg Leu Phe Ser Arg Ser Phe Thr Gln Ala Leu Gly Lys
1               5                   10                  15
```

<210> SEQ ID NO 93
<211> LENGTH: 16
<212> TYPE: PRT
<213> ORGANISM: Artificial
<220> FEATURE:
<223> OTHER INFORMATION: S. mutans targeting peptide

<400> SEQUENCE: 93

```
Thr Phe Phe Arg Leu Phe Asn Arg Ser Phe Thr Gln Ala Leu Gly Ala
1               5                   10                  15
```

<210> SEQ ID NO 94
<211> LENGTH: 16
<212> TYPE: PRT
<213> ORGANISM: Artificial
<220> FEATURE:
<223> OTHER INFORMATION: S. mutans targeting peptide

<400> SEQUENCE: 94

```
Thr Phe Phe Arg Leu Phe Asp Arg Ser Phe Thr Gln Ala Leu Gly Lys
1               5                   10                  15
```

<210> SEQ ID NO 95
<211> LENGTH: 16
<212> TYPE: PRT
<213> ORGANISM: Artificial
<220> FEATURE:
<223> OTHER INFORMATION: S. mutans targeting peptide

<400> SEQUENCE: 95

```
Thr Phe Phe Arg Leu Phe Asn Arg Ser Phe Thr Gln Ala Leu Gly Phe
1               5                   10                  15
```

<210> SEQ ID NO 96
<211> LENGTH: 16
<212> TYPE: PRT
<213> ORGANISM: Artificial
<220> FEATURE:
<223> OTHER INFORMATION: S. mutans targeting peptide

<400> SEQUENCE: 96

Thr Phe Phe Arg Ala Phe Ala Arg Ser Phe Thr Gln Ala Ala Ala Lys
1               5                   10                  15

<210> SEQ ID NO 97
<211> LENGTH: 16
<212> TYPE: PRT
<213> ORGANISM: Artificial
<220> FEATURE:
<223> OTHER INFORMATION: S. mutans targeting peptide

<400> SEQUENCE: 97

Thr Phe Phe Arg Leu Phe Ala Arg Ser Phe Thr Gln Ala Ala Gly Lys
1               5                   10                  15

<210> SEQ ID NO 98
<211> LENGTH: 14
<212> TYPE: PRT
<213> ORGANISM: Artificial
<220> FEATURE:
<223> OTHER INFORMATION: S. mutans targeting peptide

<400> SEQUENCE: 98

Thr Phe Phe Arg Leu Phe Asn Arg Ser Phe Thr Gln Leu Lys
1               5                   10

<210> SEQ ID NO 99
<211> LENGTH: 16
<212> TYPE: PRT
<213> ORGANISM: Artificial
<220> FEATURE:
<223> OTHER INFORMATION: S. mutans targeting peptide

<400> SEQUENCE: 99

Thr Phe Phe Arg Leu Phe Asn Arg Ser Phe Thr Gln Ala Leu Gly Ser
1               5                   10                  15

<210> SEQ ID NO 100
<211> LENGTH: 16
<212> TYPE: PRT
<213> ORGANISM: Artificial
<220> FEATURE:
<223> OTHER INFORMATION: S. mutans targeting peptide

<400> SEQUENCE: 100

Thr Leu Phe Arg Leu Phe Asn Arg Ser Phe Thr Gln Ala Leu Gly Lys
1               5                   10                  15

<210> SEQ ID NO 101
<211> LENGTH: 16
<212> TYPE: PRT
<213> ORGANISM: Artificial
<220> FEATURE:
<223> OTHER INFORMATION: S. mutans targeting peptide

<400> SEQUENCE: 101

Thr Phe Phe Arg Leu Asn Phe Arg Ser Phe Thr Gln Ala Leu Gly Lys
1               5                   10                  15

```
<210> SEQ ID NO 102
<211> LENGTH: 16
<212> TYPE: PRT
<213> ORGANISM: Artificial
<220> FEATURE:
<223> OTHER INFORMATION: S. mutans targeting peptide

<400> SEQUENCE: 102

Thr Phe Phe Arg Leu Phe Asn Arg Ser Gln Thr Gln Ala Leu Gly Lys
1               5                   10                  15

<210> SEQ ID NO 103
<211> LENGTH: 16
<212> TYPE: PRT
<213> ORGANISM: Artificial
<220> FEATURE:
<223> OTHER INFORMATION: S. mutans targeting peptide

<400> SEQUENCE: 103

Thr Phe Phe Arg Leu Phe Ala Ala Ala Phe Thr Gln Ala Leu Gly Lys
1               5                   10                  15

<210> SEQ ID NO 104
<211> LENGTH: 16
<212> TYPE: PRT
<213> ORGANISM: Artificial
<220> FEATURE:
<223> OTHER INFORMATION: S. mutans targeting peptide

<400> SEQUENCE: 104

Thr Phe Phe Arg Leu Phe Asn Arg Ser Phe Thr Gln Ala Leu Gly Lys
1               5                   10                  15

<210> SEQ ID NO 105
<211> LENGTH: 16
<212> TYPE: PRT
<213> ORGANISM: Artificial
<220> FEATURE:
<223> OTHER INFORMATION: S. mutans targeting peptide

<400> SEQUENCE: 105

Thr Phe Phe Arg Leu Phe Asn Arg Ser Ala Ala Ala Ala Leu Gly Lys
1               5                   10                  15

<210> SEQ ID NO 106
<211> LENGTH: 16
<212> TYPE: PRT
<213> ORGANISM: Artificial
<220> FEATURE:
<223> OTHER INFORMATION: S. mutans targeting peptide

<400> SEQUENCE: 106

Thr Phe Phe Arg Leu Phe Phe Arg Ser Asn Thr Gln Ala Leu Gly Lys
1               5                   10                  15

<210> SEQ ID NO 107
<211> LENGTH: 16
<212> TYPE: PRT
<213> ORGANISM: Artificial
<220> FEATURE:
<223> OTHER INFORMATION: S. mutans targeting peptide

<400> SEQUENCE: 107

Thr Phe Phe Arg Leu Phe Asn Arg Ser Phe Thr Gln Pro Leu Gly Lys
1               5                   10                  15
```

```
<210> SEQ ID NO 108
<211> LENGTH: 16
<212> TYPE: PRT
<213> ORGANISM: Artificial
<220> FEATURE:
<223> OTHER INFORMATION: S. mutans targeting peptide

<400> SEQUENCE: 108

Thr Ala Phe Arg Leu Ala Asn Arg Ser Ala Thr Gln Ala Leu Gly Lys
1               5                   10                  15

<210> SEQ ID NO 109
<211> LENGTH: 16
<212> TYPE: PRT
<213> ORGANISM: Artificial
<220> FEATURE:
<223> OTHER INFORMATION: S. mutans targeting peptide

<400> SEQUENCE: 109

Thr Phe Phe Arg Leu Phe Asn Arg Ser Phe Thr Gln Ala Ala Ala Ala
1               5                   10                  15

<210> SEQ ID NO 110
<211> LENGTH: 16
<212> TYPE: PRT
<213> ORGANISM: Artificial
<220> FEATURE:
<223> OTHER INFORMATION: S. mutans targeting peptide

<400> SEQUENCE: 110

Thr Phe Phe Arg Leu Gln Asn Arg Ser Phe Thr Gln Ala Leu Gly Lys
1               5                   10                  15

<210> SEQ ID NO 111
<211> LENGTH: 16
<212> TYPE: PRT
<213> ORGANISM: Artificial
<220> FEATURE:
<223> OTHER INFORMATION: S. mutans targeting peptide

<400> SEQUENCE: 111

Thr Phe Phe Arg Leu Phe Asn Arg Ser Phe Thr Gln Ala Leu Pro Lys
1               5                   10                  15

<210> SEQ ID NO 112
<211> LENGTH: 16
<212> TYPE: PRT
<213> ORGANISM: Artificial
<220> FEATURE:
<223> OTHER INFORMATION: S. mutans targeting peptide

<400> SEQUENCE: 112

Thr Tyr Tyr Arg Leu Phe Asn Arg Ser Phe Thr Gln Ala Leu Gly Lys
1               5                   10                  15

<210> SEQ ID NO 113
<211> LENGTH: 15
<212> TYPE: PRT
<213> ORGANISM: Artificial
<220> FEATURE:
<223> OTHER INFORMATION: S. mutans targeting peptide

<400> SEQUENCE: 113

Thr Phe Phe Arg Leu Phe Arg Ser Phe Thr Gln Ala Leu Gly Lys
1               5                   10                  15

<210> SEQ ID NO 114
```

```
<211> LENGTH: 16
<212> TYPE: PRT
<213> ORGANISM: Artificial
<220> FEATURE:
<223> OTHER INFORMATION: S. mutans targeting peptide

<400> SEQUENCE: 114

Thr Gln Phe Arg Leu Gln Asn Arg Ser Gln Thr Gln Ala Leu Gly Lys
1               5                   10                  15

<210> SEQ ID NO 115
<211> LENGTH: 16
<212> TYPE: PRT
<213> ORGANISM: Artificial
<220> FEATURE:
<223> OTHER INFORMATION: Antimicrobial peptide

<400> SEQUENCE: 115

Lys Asn Leu Arg Ile Ile Arg Lys Gly Ile His Ile Ile Lys Lys Tyr
1               5                   10                  15

<210> SEQ ID NO 116
<211> LENGTH: 18
<212> TYPE: PRT
<213> ORGANISM: Artificial
<220> FEATURE:
<223> OTHER INFORMATION: Antimicrobial peptide

<400> SEQUENCE: 116

Lys Asn Leu Arg Arg Ile Ile Arg Lys Gly Ile His Ile Ile Lys Lys
1               5                   10                  15

Tyr Gly

<210> SEQ ID NO 117
<211> LENGTH: 18
<212> TYPE: PRT
<213> ORGANISM: Artificial
<220> FEATURE:
<223> OTHER INFORMATION: Antimicrobial peptide

<400> SEQUENCE: 117

Lys Asn Leu Arg Arg Ile Ile Arg Lys Thr Ile His Ile Ile Lys Lys
1               5                   10                  15

Tyr Gly

<210> SEQ ID NO 118
<211> LENGTH: 18
<212> TYPE: PRT
<213> ORGANISM: Artificial
<220> FEATURE:
<223> OTHER INFORMATION: Antimicrobial peptide

<400> SEQUENCE: 118

Lys Asn Leu Arg Arg Ile Gly Arg Lys Ile Ile His Ile Ile Lys Lys
1               5                   10                  15

Tyr Gly

<210> SEQ ID NO 119
<211> LENGTH: 18
<212> TYPE: PRT
<213> ORGANISM: Artificial
<220> FEATURE:
<223> OTHER INFORMATION: Antimicrobial peptide

<400> SEQUENCE: 119
```

```
Lys Asn Leu Arg Arg Ile Thr Arg Lys Ile Ile His Ile Ile Lys Lys
1               5                   10                  15

Tyr Gly

<210> SEQ ID NO 120
<211> LENGTH: 18
<212> TYPE: PRT
<213> ORGANISM: Artificial
<220> FEATURE:
<223> OTHER INFORMATION: Antimicrobial peptide

<400> SEQUENCE: 120

Lys Asn Leu Arg Arg Ile Ile Arg Lys Ile Ile His Ile Ile Lys Lys
1               5                   10                  15

Tyr Gly

<210> SEQ ID NO 121
<211> LENGTH: 18
<212> TYPE: PRT
<213> ORGANISM: Artificial
<220> FEATURE:
<223> OTHER INFORMATION: Antimicrobial peptide

<400> SEQUENCE: 121

Gly Leu Leu Arg Arg Leu Arg Lys Lys Ile Gly Glu Ile Phe Lys Lys
1               5                   10                  15

Tyr Gly

<210> SEQ ID NO 122
<211> LENGTH: 18
<212> TYPE: PRT
<213> ORGANISM: Artificial
<220> FEATURE:
<223> OTHER INFORMATION: Antimicrobial peptide

<400> SEQUENCE: 122

Arg Gly Gly Arg Leu Cys Tyr Cys Arg Arg Arg Phe Cys Val Cys Val
1               5                   10                  15

Gly Arg

<210> SEQ ID NO 123
<211> LENGTH: 17
<212> TYPE: PRT
<213> ORGANISM: Artificial
<220> FEATURE:
<223> OTHER INFORMATION: Antimicrobial peptide

<400> SEQUENCE: 123

Gly Leu Gly Arg Val Ile Gly Arg Leu Ile Lys Gln Ile Ile Trp Arg
1               5                   10                  15

Arg

<210> SEQ ID NO 124
<211> LENGTH: 19
<212> TYPE: PRT
<213> ORGANISM: Artificial
<220> FEATURE:
<223> OTHER INFORMATION: Antimicrobial peptide

<400> SEQUENCE: 124

Val Tyr Arg Lys Arg Lys Ser Ile Leu Lys Ile Tyr Ala Lys Leu Lys
1               5                   10                  15

Gly Trp His
```

<210> SEQ ID NO 125
<211> LENGTH: 20
<212> TYPE: PRT
<213> ORGANISM: Artificial
<220> FEATURE:
<223> OTHER INFORMATION: Antimicrobial peptide

<400> SEQUENCE: 125

Asn Tyr Arg Leu Val Asn Ala Ile Phe Ser Lys Ile Phe Lys Lys
1               5                   10                  15

Phe Ile Lys Phe
            20

<210> SEQ ID NO 126
<211> LENGTH: 11
<212> TYPE: PRT
<213> ORGANISM: Artificial
<220> FEATURE:
<223> OTHER INFORMATION: Antimicrobial peptide

<400> SEQUENCE: 126

Lys Ile Leu Lys Phe Leu Phe Lys Lys Val Phe
1               5                   10

<210> SEQ ID NO 127
<211> LENGTH: 11
<212> TYPE: PRT
<213> ORGANISM: Artificial
<220> FEATURE:
<223> OTHER INFORMATION: Antimicrobial peptide

<400> SEQUENCE: 127

Phe Ile Arg Lys Phe Leu Lys Lys Trp Leu Leu
1               5                   10

<210> SEQ ID NO 128
<211> LENGTH: 11
<212> TYPE: PRT
<213> ORGANISM: Artificial
<220> FEATURE:
<223> OTHER INFORMATION: Antimicrobial peptide

<400> SEQUENCE: 128

Lys Leu Phe Lys Phe Leu Arg Lys His Leu Leu
1               5                   10

<210> SEQ ID NO 129
<211> LENGTH: 11
<212> TYPE: PRT
<213> ORGANISM: Artificial
<220> FEATURE:
<223> OTHER INFORMATION: Antimicrobial peptide

<400> SEQUENCE: 129

Lys Ile Leu Lys Phe Leu Phe Lys Gln Val Phe
1               5                   10

<210> SEQ ID NO 130
<211> LENGTH: 11
<212> TYPE: PRT
<213> ORGANISM: Artificial
<220> FEATURE:
<223> OTHER INFORMATION: Antimicrobial peptide

<400> SEQUENCE: 130

Lys Ile Leu Lys Lys Leu Phe Lys Phe Val Phe
1               5                   10

<210> SEQ ID NO 131
<211> LENGTH: 11
<212> TYPE: PRT
<213> ORGANISM: Artificial
<220> FEATURE:
<223> OTHER INFORMATION: Antimicrobial peptide

<400> SEQUENCE: 131

Gly Ile Leu Lys Lys Leu Phe Thr Lys Val Phe
1               5                   10

<210> SEQ ID NO 132
<211> LENGTH: 9
<212> TYPE: PRT
<213> ORGANISM: Artificial
<220> FEATURE:
<223> OTHER INFORMATION: Antimicrobial peptide

<400> SEQUENCE: 132

Leu Arg Lys Phe Leu His Lys Leu Phe
1               5

<210> SEQ ID NO 133
<211> LENGTH: 9
<212> TYPE: PRT
<213> ORGANISM: Artificial
<220> FEATURE:
<223> OTHER INFORMATION: Antimicrobial peptide

<400> SEQUENCE: 133

Leu Arg Lys Asn Leu Arg Trp Leu Phe
1               5

<210> SEQ ID NO 134
<211> LENGTH: 11
<212> TYPE: PRT
<213> ORGANISM: Artificial
<220> FEATURE:
<223> OTHER INFORMATION: Antimicrobial peptide

<400> SEQUENCE: 134

Phe Ile Arg Lys Phe Leu Gln Lys Leu His Leu
1               5                   10

<210> SEQ ID NO 135
<211> LENGTH: 11
<212> TYPE: PRT
<213> ORGANISM: Artificial
<220> FEATURE:
<223> OTHER INFORMATION: Antimicrobial peptide

<400> SEQUENCE: 135

Phe Thr Arg Lys Phe Leu Lys Phe Leu His Leu
1               5                   10

<210> SEQ ID NO 136
<211> LENGTH: 12
<212> TYPE: PRT
<213> ORGANISM: Artificial
<220> FEATURE:
<223> OTHER INFORMATION: Antimicrobial peptide

<400> SEQUENCE: 136

Lys Lys Phe Lys Lys Phe Lys Val Leu Lys Ile Leu

<210> SEQ ID NO 137
<211> LENGTH: 12
<212> TYPE: PRT
<213> ORGANISM: Artificial
<220> FEATURE:
<223> OTHER INFORMATION: Antimicrobial peptide

<400> SEQUENCE: 137

Leu Leu Lys Leu Leu Lys Leu Lys Lys Leu Lys Phe
1               5                   10

<210> SEQ ID NO 138
<211> LENGTH: 14
<212> TYPE: PRT
<213> ORGANISM: Artificial
<220> FEATURE:
<223> OTHER INFORMATION: Antimicrobial peptide

<400> SEQUENCE: 138

Phe Leu Lys Phe Leu Lys Lys Phe Phe Lys Lys Leu Lys Tyr
1               5                   10

<210> SEQ ID NO 139
<211> LENGTH: 16
<212> TYPE: PRT
<213> ORGANISM: Artificial
<220> FEATURE:
<223> OTHER INFORMATION: Antimicrobial peptide

<400> SEQUENCE: 139

Gly Trp Leu Lys Met Phe Lys Lys Ile Ile Gly Lys Phe Gly Lys Phe
1               5                   10                  15

<210> SEQ ID NO 140
<211> LENGTH: 16
<212> TYPE: PRT
<213> ORGANISM: Artificial
<220> FEATURE:
<223> OTHER INFORMATION: Antimicrobial peptide

<400> SEQUENCE: 140

Gly Ile Phe Lys Lys Phe Val Lys Ile Leu Tyr Lys Val Gln Lys Leu
1               5                   10                  15

<210> SEQ ID NO 141
<211> LENGTH: 24
<212> TYPE: PRT
<213> ORGANISM: Artificial
<220> FEATURE:
<223> OTHER INFORMATION: Antimicrobial peptide

<400> SEQUENCE: 141

Gly Arg Leu Val Leu Glu Ile Thr Ala Asp Glu Val Lys Ala Leu Gly
1               5                   10                  15

Glu Ala Leu Ala Asn Ala Lys Ile
            20

<210> SEQ ID NO 142
<211> LENGTH: 21
<212> TYPE: PRT
<213> ORGANISM: Artificial
<220> FEATURE:
<223> OTHER INFORMATION: Antimicrobial peptide

<400> SEQUENCE: 142

```
Tyr Ile Gln Phe His Leu Asn Gln Gln Pro Arg Pro Lys Val Lys Lys
1               5                   10                  15

Ile Lys Ile Phe Leu
            20

<210> SEQ ID NO 143
<211> LENGTH: 32
<212> TYPE: PRT
<213> ORGANISM: Artificial
<220> FEATURE:
<223> OTHER INFORMATION: Antimicrobial peptide

<400> SEQUENCE: 143

Gly Ser Val Ile Lys Lys Arg Arg Lys Arg Met Ala Lys Lys Lys His
1               5                   10                  15

Arg Lys Leu Leu Lys Lys Thr Arg Ile Gln Arg Arg Ala Gly Lys
            20                  25                  30

<210> SEQ ID NO 144
<211> LENGTH: 30
<212> TYPE: PRT
<213> ORGANISM: Artificial
<220> FEATURE:
<223> OTHER INFORMATION: Antimicrobial peptide

<400> SEQUENCE: 144

Met Arg Phe Gly Ser Leu Ala Leu Val Ala Tyr Asp Ser Ala Ile Lys
1               5                   10                  15

His Ser Trp Pro Arg Pro Ser Val Arg Arg Leu Arg Met
            20                  25                  30

<210> SEQ ID NO 145
<211> LENGTH: 39
<212> TYPE: PRT
<213> ORGANISM: Artificial
<220> FEATURE:
<223> OTHER INFORMATION: Antimicrobial peptide

<400> SEQUENCE: 145

Phe Glu Ser Lys Ile Leu Asn Ala Ser Lys Glu Leu Asp Lys Glu Lys
1               5                   10                  15

Lys Val Asn Thr Ala Leu Ser Phe Asn Ser His Gln Asp Phe Ala Lys
            20                  25                  30

Ala Tyr Gln Asn Gly Lys Ile
        35

<210> SEQ ID NO 146
<211> LENGTH: 18
<212> TYPE: PRT
<213> ORGANISM: Artificial
<220> FEATURE:
<223> OTHER INFORMATION: Antimicrobial peptide

<400> SEQUENCE: 146

Trp Ser Arg Val Pro Gly His Ser Asp Thr Gly Trp Lys Val Trp His
1               5                   10                  15

Arg Trp

<210> SEQ ID NO 147
<211> LENGTH: 21
<212> TYPE: PRT
<213> ORGANISM: Artificial
<220> FEATURE:
```

<223> OTHER INFORMATION: Antimicrobial peptide

<400> SEQUENCE: 147

Met Gly Ile Ile Ala Gly Ile Ile Lys Phe Ile Lys Gly Leu Ile Glu
1               5                   10                  15

Lys Phe Thr Gly Lys
            20

<210> SEQ ID NO 148
<211> LENGTH: 16
<212> TYPE: PRT
<213> ORGANISM: Artificial
<220> FEATURE:
<223> OTHER INFORMATION: Antimicrobial peptide

<400> SEQUENCE: 148

Arg Glu Ser Lys Leu Ile Ala Met Ala Asp Met Ile Arg Arg Arg Ile
1               5                   10                  15

<210> SEQ ID NO 149
<211> LENGTH: 24
<212> TYPE: PRT
<213> ORGANISM: Artificial
<220> FEATURE:
<223> OTHER INFORMATION: Antimicrobial peptide

<400> SEQUENCE: 149

Leu Ser Leu Ala Thr Phe Ala Lys Ile Phe Met Thr Arg Ser Asn Trp
1               5                   10                  15

Ser Leu Lys Arg Phe Asn Arg Leu
            20

<210> SEQ ID NO 150
<211> LENGTH: 30
<212> TYPE: PRT
<213> ORGANISM: Artificial
<220> FEATURE:
<223> OTHER INFORMATION: Antimicrobial peptide

<400> SEQUENCE: 150

Met Ile Arg Ile Arg Ser Pro Thr Lys Lys Lys Leu Asn Arg Asn Ser
1               5                   10                  15

Ile Ser Asp Trp Lys Ser Asn Thr Ser Gly Arg Phe Phe Tyr
            20                  25                  30

<210> SEQ ID NO 151
<211> LENGTH: 37
<212> TYPE: PRT
<213> ORGANISM: Artificial
<220> FEATURE:
<223> OTHER INFORMATION: Antimicrobial peptide

<400> SEQUENCE: 151

Met Lys Arg Arg Arg Cys Asn Trp Cys Gly Lys Leu Phe Tyr Leu Glu
1               5                   10                  15

Glu Lys Ser Lys Glu Ala Tyr Cys Cys Lys Glu Cys Arg Lys Lys Ala
            20                  25                  30

Lys Lys Val Lys Lys
        35

<210> SEQ ID NO 152
<211> LENGTH: 28
<212> TYPE: PRT
<213> ORGANISM: Artificial

```
<220> FEATURE:
<223> OTHER INFORMATION: Antimicrobial peptide

<400> SEQUENCE: 152

Val Leu Pro Phe Pro Ala Ile Pro Leu Ser Arg Arg Ala Cys Val
1               5                   10                  15

Ala Ala Pro Arg Pro Arg Ser Arg Gln Arg Ala Ser
            20                  25

<210> SEQ ID NO 153
<211> LENGTH: 30
<212> TYPE: PRT
<213> ORGANISM: Artificial
<220> FEATURE:
<223> OTHER INFORMATION: Antimicrobial peptide

<400> SEQUENCE: 153

Lys Asn Lys Lys Gln Thr Asp Ile Leu Glu Lys Val Lys Glu Ile Leu
1               5                   10                  15

Asp Lys Lys Lys Lys Thr Lys Ser Val Gly Gln Lys Leu Tyr
            20                  25                  30

<210> SEQ ID NO 154
<211> LENGTH: 15
<212> TYPE: PRT
<213> ORGANISM: Artificial
<220> FEATURE:
<223> OTHER INFORMATION: Antimicrobial peptide

<400> SEQUENCE: 154

Ser Leu Gln Ser Gln Leu Gly Pro Cys Leu His Asp Gln Arg His
1               5                   10                  15

<210> SEQ ID NO 155
<211> LENGTH: 28
<212> TYPE: PRT
<213> ORGANISM: Artificial
<220> FEATURE:
<223> OTHER INFORMATION: Antimicrobial peptide

<400> SEQUENCE: 155

Lys Phe Gln Gly Glu Phe Thr Asn Ile Gly Gln Ser Tyr Ile Val Ser
1               5                   10                  15

Ala Ser His Met Ser Thr Ser Leu Asn Thr Gly Lys
            20                  25

<210> SEQ ID NO 156
<211> LENGTH: 41
<212> TYPE: PRT
<213> ORGANISM: Artificial
<220> FEATURE:
<223> OTHER INFORMATION: Antimicrobial peptide

<400> SEQUENCE: 156

Thr Lys Lys Ile Glu Leu Lys Arg Phe Val Asp Ala Phe Val Lys Lys
1               5                   10                  15

Ser Tyr Glu Asn Tyr Ile Leu Glu Arg Glu Leu Lys Lys Leu Ile Lys
            20                  25                  30

Ala Ile Asn Glu Glu Leu Pro Thr Lys
                35                  40

<210> SEQ ID NO 157
<211> LENGTH: 20
<212> TYPE: PRT
```

```
<213> ORGANISM: Artificial
<220> FEATURE:
<223> OTHER INFORMATION: Antimicrobial peptide

<400> SEQUENCE: 157

Lys Phe Ser Asp Gln Ile Asp Lys Gly Gln Asp Ala Leu Lys Asp Lys
1               5                   10                  15

Leu Gly Asp Leu
            20

<210> SEQ ID NO 158
<211> LENGTH: 13
<212> TYPE: PRT
<213> ORGANISM: Artificial
<220> FEATURE:
<223> OTHER INFORMATION: Antimicrobial peptide

<400> SEQUENCE: 158

Leu Ser Glu Met Glu Arg Arg Arg Leu Arg Lys Arg Ala
1               5                   10

<210> SEQ ID NO 159
<211> LENGTH: 25
<212> TYPE: PRT
<213> ORGANISM: Artificial
<220> FEATURE:
<223> OTHER INFORMATION: Antimicrobial peptide

<400> SEQUENCE: 159

Arg Arg Gly Cys Thr Glu Arg Leu Arg Arg Met Ala Arg Arg Asn Ala
1               5                   10                  15

Trp Asp Leu Tyr Ala Glu His Phe Tyr
            20                  25

<210> SEQ ID NO 160
<211> LENGTH: 26
<212> TYPE: PRT
<213> ORGANISM: Artificial
<220> FEATURE:
<223> OTHER INFORMATION: Antimicrobial peptide

<400> SEQUENCE: 160

Ser Lys Phe Lys Val Leu Arg Lys Ile Ile Ile Lys Glu Tyr Lys Gly
1               5                   10                  15

Glu Leu Met Leu Ser Ile Gln Lys Gln Arg
            20                  25

<210> SEQ ID NO 161
<211> LENGTH: 20
<212> TYPE: PRT
<213> ORGANISM: Artificial
<220> FEATURE:
<223> OTHER INFORMATION: Antimicrobial peptide

<400> SEQUENCE: 161

Phe Glu Leu Val Asp Trp Leu Glu Thr Asn Leu Gly Lys Ile Leu Lys
1               5                   10                  15

Ser Lys Ser Ala
            20

<210> SEQ ID NO 162
<211> LENGTH: 22
<212> TYPE: PRT
<213> ORGANISM: Artificial
<220> FEATURE:
```

```
<223> OTHER INFORMATION: Antimicrobial peptide

<400> SEQUENCE: 162

Leu Val Leu Arg Ile Cys Thr Asp Leu Phe Thr Phe Ile Lys Trp Thr
1               5                   10                  15

Ile Lys Gln Arg Lys Ser
            20

<210> SEQ ID NO 163
<211> LENGTH: 24
<212> TYPE: PRT
<213> ORGANISM: Artificial
<220> FEATURE:
<223> OTHER INFORMATION: Antimicrobial peptide

<400> SEQUENCE: 163

Val Tyr Ser Phe Leu Tyr Val Leu Val Ile Val Arg Lys Leu Leu Ser
1               5                   10                  15

Met Lys Lys Arg Ile Glu Arg Leu
            20

<210> SEQ ID NO 164
<211> LENGTH: 18
<212> TYPE: PRT
<213> ORGANISM: Artificial
<220> FEATURE:
<223> OTHER INFORMATION: Antimicrobial peptide

<400> SEQUENCE: 164

Gly Ile Val Leu Ile Gly Leu Lys Leu Ile Pro Leu Leu Ala Asn Val
1               5                   10                  15

Leu Arg

<210> SEQ ID NO 165
<211> LENGTH: 21
<212> TYPE: PRT
<213> ORGANISM: Artificial
<220> FEATURE:
<223> OTHER INFORMATION: Antimicrobial peptide

<400> SEQUENCE: 165

Val Met Gln Ser Leu Tyr Val Lys Pro Pro Leu Ile Leu Val Thr Lys
1               5                   10                  15

Leu Ala Gln Gln Asn
            20

<210> SEQ ID NO 166
<211> LENGTH: 16
<212> TYPE: PRT
<213> ORGANISM: Artificial
<220> FEATURE:
<223> OTHER INFORMATION: Antimicrobial peptide

<400> SEQUENCE: 166

Ser Phe Met Pro Glu Ile Gln Lys Asn Thr Ile Pro Thr Gln Met Lys
1               5                   10                  15

<210> SEQ ID NO 167
<211> LENGTH: 39
<212> TYPE: PRT
<213> ORGANISM: Artificial
<220> FEATURE:
<223> OTHER INFORMATION: Antimicrobial peptide

<400> SEQUENCE: 167
```

```
Leu Gly Leu Thr Ala Gly Val Ala Tyr Ala Ala Gln Pro Thr Asn Gln
1               5                   10                  15

Pro Thr Asn Gln Pro Thr Asn Gln Pro Thr Asn Gln Pro Thr Asn Gln
                20                  25                  30

Pro Thr Asn Gln Pro Arg Trp
                35

<210> SEQ ID NO 168
<211> LENGTH: 15
<212> TYPE: PRT
<213> ORGANISM: Artificial
<220> FEATURE:
<223> OTHER INFORMATION: Antimicrobial peptide

<400> SEQUENCE: 168

Cys Gly Lys Leu Leu Glu Gln Lys Asn Phe Phe Leu Lys Thr Arg
1               5                   10                  15

<210> SEQ ID NO 169
<211> LENGTH: 30
<212> TYPE: PRT
<213> ORGANISM: Artificial
<220> FEATURE:
<223> OTHER INFORMATION: Antimicrobial peptide

<400> SEQUENCE: 169

Ala Ser Lys Gln Ala Ser Lys Gln Ala Ser Lys Gln Ala Ser Lys Gln
1               5                   10                  15

Ala Ser Lys Gln Ala Ser Arg Ser Leu Lys Asn His Leu Leu
                20                  25                  30

<210> SEQ ID NO 170
<211> LENGTH: 24
<212> TYPE: PRT
<213> ORGANISM: Artificial
<220> FEATURE:
<223> OTHER INFORMATION: Antimicrobial peptide

<400> SEQUENCE: 170

Pro Asp Ala Pro Arg Thr Cys Tyr His Lys Pro Ile Leu Ala Ala Leu
1               5                   10                  15

Ser Arg Ile Val Val Thr Asp Arg
                20

<210> SEQ ID NO 171
<211> LENGTH: 8
<212> TYPE: PRT
<213> ORGANISM: Artificial
<220> FEATURE:
<223> OTHER INFORMATION: Antimicrobial peptide

<400> SEQUENCE: 171

Asn Tyr Ala Val Val Ser His Thr
1               5

<210> SEQ ID NO 172
<211> LENGTH: 23
<212> TYPE: PRT
<213> ORGANISM: Artificial
<220> FEATURE:
<223> OTHER INFORMATION: Antimicrobial peptide

<400> SEQUENCE: 172

Phe Gln Lys Pro Phe Thr Gly Glu Glu Val Glu Asp Phe Gln Asp Asp
```

```
1               5                   10                  15
Asp Glu Ile Pro Thr Ile Ile
            20

<210> SEQ ID NO 173
<211> LENGTH: 15
<212> TYPE: PRT
<213> ORGANISM: Artificial
<220> FEATURE:
<223> OTHER INFORMATION: Antimicrobial peptide

<400> SEQUENCE: 173

Gly Trp Arg Leu Ile Lys Lys Ile Leu Arg Val Phe Lys Gly Leu
1               5                   10                  15

<210> SEQ ID NO 174
<211> LENGTH: 11
<212> TYPE: PRT
<213> ORGANISM: Artificial
<220> FEATURE:
<223> OTHER INFORMATION: Antimicrobial peptide

<400> SEQUENCE: 174

Phe Lys Lys Phe Trp Lys Trp Phe Arg Arg Phe
1               5                   10

<210> SEQ ID NO 175
<211> LENGTH: 11
<212> TYPE: PRT
<213> ORGANISM: Artificial
<220> FEATURE:
<223> OTHER INFORMATION: Antimicrobial peptide

<400> SEQUENCE: 175

Leu Lys Arg Phe Leu Lys Trp Phe Lys Arg Phe
1               5                   10

<210> SEQ ID NO 176
<211> LENGTH: 11
<212> TYPE: PRT
<213> ORGANISM: Artificial
<220> FEATURE:
<223> OTHER INFORMATION: Antimicrobial peptide

<400> SEQUENCE: 176

Lys Leu Phe Lys Arg Trp Lys His Leu Phe Arg
1               5                   10

<210> SEQ ID NO 177
<211> LENGTH: 11
<212> TYPE: PRT
<213> ORGANISM: Artificial
<220> FEATURE:
<223> OTHER INFORMATION: Antimicrobial peptide

<400> SEQUENCE: 177

Arg Leu Leu Lys Arg Phe Lys His Leu Phe Lys
1               5                   10

<210> SEQ ID NO 178
<211> LENGTH: 11
<212> TYPE: PRT
<213> ORGANISM: Artificial
<220> FEATURE:
<223> OTHER INFORMATION: Antimicrobial peptide

<400> SEQUENCE: 178
```

```
Phe Lys Thr Phe Leu Lys Trp Leu His Arg Phe
1               5                   10

<210> SEQ ID NO 179
<211> LENGTH: 11
<212> TYPE: PRT
<213> ORGANISM: Artificial
<220> FEATURE:
<223> OTHER INFORMATION: Antimicrobial peptide

<400> SEQUENCE: 179

Ile Lys Gln Leu Leu His Phe Phe Gln Arg Phe
1               5                   10

<210> SEQ ID NO 180
<211> LENGTH: 11
<212> TYPE: PRT
<213> ORGANISM: Artificial
<220> FEATURE:
<223> OTHER INFORMATION: Antimicrobial peptide

<400> SEQUENCE: 180

Lys Leu Leu Gln Thr Phe Lys Gln Ile Phe Arg
1               5                   10

<210> SEQ ID NO 181
<211> LENGTH: 11
<212> TYPE: PRT
<213> ORGANISM: Artificial
<220> FEATURE:
<223> OTHER INFORMATION: Antimicrobial peptide

<400> SEQUENCE: 181

Arg Ile Leu Lys Glu Leu Lys Asn Leu Phe Lys
1               5                   10

<210> SEQ ID NO 182
<211> LENGTH: 11
<212> TYPE: PRT
<213> ORGANISM: Artificial
<220> FEATURE:
<223> OTHER INFORMATION: Antimicrobial peptide

<400> SEQUENCE: 182

Leu Lys Gln Phe Val His Phe Ile His Arg Phe
1               5                   10

<210> SEQ ID NO 183
<211> LENGTH: 11
<212> TYPE: PRT
<213> ORGANISM: Artificial
<220> FEATURE:
<223> OTHER INFORMATION: Antimicrobial peptide

<400> SEQUENCE: 183

Val Lys Thr Leu Leu His Ile Phe Gln Arg Phe
1               5                   10

<210> SEQ ID NO 184
<211> LENGTH: 11
<212> TYPE: PRT
<213> ORGANISM: Artificial
<220> FEATURE:
<223> OTHER INFORMATION: Antimicrobial peptide

<400> SEQUENCE: 184
```

```
Lys Leu Val Glu Gln Leu Lys Glu Ile Phe Arg
1               5                   10

<210> SEQ ID NO 185
<211> LENGTH: 11
<212> TYPE: PRT
<213> ORGANISM: Artificial
<220> FEATURE:
<223> OTHER INFORMATION: Antimicrobial peptide

<400> SEQUENCE: 185

Arg Val Leu Gln Glu Ile Lys Gln Ile Leu Lys
1               5                   10

<210> SEQ ID NO 186
<211> LENGTH: 11
<212> TYPE: PRT
<213> ORGANISM: Artificial
<220> FEATURE:
<223> OTHER INFORMATION: Antimicrobial peptide

<400> SEQUENCE: 186

Val Lys Asn Leu Ala Glu Leu Val His Arg Phe
1               5                   10

<210> SEQ ID NO 187
<211> LENGTH: 11
<212> TYPE: PRT
<213> ORGANISM: Artificial
<220> FEATURE:
<223> OTHER INFORMATION: Antimicrobial peptide

<400> SEQUENCE: 187

Ala Thr His Leu Leu His Ala Leu Gln Arg Phe
1               5                   10

<210> SEQ ID NO 188
<211> LENGTH: 11
<212> TYPE: PRT
<213> ORGANISM: Artificial
<220> FEATURE:
<223> OTHER INFORMATION: Antimicrobial peptide

<400> SEQUENCE: 188

Lys Leu Ala Glu Asn Val Lys Glu Ile Leu Arg
1               5                   10

<210> SEQ ID NO 189
<211> LENGTH: 11
<212> TYPE: PRT
<213> ORGANISM: Artificial
<220> FEATURE:
<223> OTHER INFORMATION: Antimicrobial peptide

<400> SEQUENCE: 189

Arg Ala Leu His Glu Ala Lys Glu Ala Leu Lys
1               5                   10

<210> SEQ ID NO 190
<211> LENGTH: 11
<212> TYPE: PRT
<213> ORGANISM: Artificial
<220> FEATURE:
<223> OTHER INFORMATION: Antimicrobial peptide

<400> SEQUENCE: 190

Phe His Tyr Phe Trp His Trp Phe His Arg Phe
```

```
1               5                   10
```

<210> SEQ ID NO 191
<211> LENGTH: 11
<212> TYPE: PRT
<213> ORGANISM: Artificial
<220> FEATURE:
<223> OTHER INFORMATION: Antimicrobial peptide

<400> SEQUENCE: 191

```
Leu Tyr His Phe Leu His Trp Phe Gln Arg Phe
1               5                   10
```

<210> SEQ ID NO 192
<211> LENGTH: 11
<212> TYPE: PRT
<213> ORGANISM: Artificial
<220> FEATURE:
<223> OTHER INFORMATION: Antimicrobial peptide

<400> SEQUENCE: 192

```
Tyr Leu Phe Gln Thr Trp Gln His Leu Phe Arg
1               5                   10
```

<210> SEQ ID NO 193
<211> LENGTH: 11
<212> TYPE: PRT
<213> ORGANISM: Artificial
<220> FEATURE:
<223> OTHER INFORMATION: Antimicrobial peptide

<400> SEQUENCE: 193

```
Tyr Leu Leu Thr Glu Phe Gln His Leu Phe Lys
1               5                   10
```

<210> SEQ ID NO 194
<211> LENGTH: 11
<212> TYPE: PRT
<213> ORGANISM: Artificial
<220> FEATURE:
<223> OTHER INFORMATION: Antimicrobial peptide

<400> SEQUENCE: 194

```
Phe Lys Thr Phe Leu Gln Trp Leu His Arg Phe
1               5                   10
```

<210> SEQ ID NO 195
<211> LENGTH: 11
<212> TYPE: PRT
<213> ORGANISM: Artificial
<220> FEATURE:
<223> OTHER INFORMATION: Antimicrobial peptide

<400> SEQUENCE: 195

```
Ile Lys Thr Leu Leu His Phe Phe Gln Arg Phe
1               5                   10
```

<210> SEQ ID NO 196
<211> LENGTH: 11
<212> TYPE: PRT
<213> ORGANISM: Artificial
<220> FEATURE:
<223> OTHER INFORMATION: Antimicrobial peptide

<400> SEQUENCE: 196

```
Lys Leu Leu Gln Thr Phe Asn Gln Ile Phe Arg
1               5                   10
```

<210> SEQ ID NO 197
<211> LENGTH: 11
<212> TYPE: PRT
<213> ORGANISM: Artificial
<220> FEATURE:
<223> OTHER INFORMATION: Antimicrobial peptide

<400> SEQUENCE: 197

Thr Ile Leu Gln Ser Leu Lys Asn Ile Phe Lys
1               5                   10

<210> SEQ ID NO 198
<211> LENGTH: 11
<212> TYPE: PRT
<213> ORGANISM: Artificial
<220> FEATURE:
<223> OTHER INFORMATION: Antimicrobial peptide

<400> SEQUENCE: 198

Leu Lys Gln Phe Val Lys Phe Ile His Arg Phe
1               5                   10

<210> SEQ ID NO 199
<211> LENGTH: 11
<212> TYPE: PRT
<213> ORGANISM: Artificial
<220> FEATURE:
<223> OTHER INFORMATION: Antimicrobial peptide

<400> SEQUENCE: 199

Val Lys Gln Leu Leu Lys Ile Phe Asn Arg Phe
1               5                   10

<210> SEQ ID NO 200
<211> LENGTH: 11
<212> TYPE: PRT
<213> ORGANISM: Artificial
<220> FEATURE:
<223> OTHER INFORMATION: Antimicrobial peptide

<400> SEQUENCE: 200

Lys Leu Val Gln Gln Leu Lys Asn Ile Phe Arg
1               5                   10

<210> SEQ ID NO 201
<211> LENGTH: 11
<212> TYPE: PRT
<213> ORGANISM: Artificial
<220> FEATURE:
<223> OTHER INFORMATION: Antimicrobial peptide

<400> SEQUENCE: 201

Arg Val Leu Asn Gln Val Lys Gln Ile Leu Lys
1               5                   10

<210> SEQ ID NO 202
<211> LENGTH: 11
<212> TYPE: PRT
<213> ORGANISM: Artificial
<220> FEATURE:
<223> OTHER INFORMATION: Antimicrobial peptide

<400> SEQUENCE: 202

Val Lys Lys Leu Ala Lys Leu Val Arg Arg Phe
1               5                   10

<210> SEQ ID NO 203
<211> LENGTH: 11
<212> TYPE: PRT
<213> ORGANISM: Artificial
<220> FEATURE:
<223> OTHER INFORMATION: Antimicrobial peptide

<400> SEQUENCE: 203

Ala Lys Arg Leu Leu Lys Val Leu Lys Arg Phe
1               5                   10

<210> SEQ ID NO 204
<211> LENGTH: 11
<212> TYPE: PRT
<213> ORGANISM: Artificial
<220> FEATURE:
<223> OTHER INFORMATION: Antimicrobial peptide

<400> SEQUENCE: 204

Lys Leu Ala Gln Lys Val Lys Arg Val Leu Arg
1               5                   10

<210> SEQ ID NO 205
<211> LENGTH: 11
<212> TYPE: PRT
<213> ORGANISM: Artificial
<220> FEATURE:
<223> OTHER INFORMATION: Antimicrobial peptide

<400> SEQUENCE: 205

Arg Ala Leu Lys Arg Ile Lys His Val Leu Lys
1               5                   10

<210> SEQ ID NO 206
<211> LENGTH: 7
<212> TYPE: PRT
<213> ORGANISM: Artificial
<220> FEATURE:
<223> OTHER INFORMATION: Antimicrobial peptide

<400> SEQUENCE: 206

Arg Arg Arg Arg Trp Trp Trp
1               5

<210> SEQ ID NO 207
<211> LENGTH: 7
<212> TYPE: PRT
<213> ORGANISM: Artificial
<220> FEATURE:
<223> OTHER INFORMATION: Antimicrobial peptide

<400> SEQUENCE: 207

Arg Arg Trp Trp Arg Arg Trp
1               5

<210> SEQ ID NO 208
<211> LENGTH: 7
<212> TYPE: PRT
<213> ORGANISM: Artificial
<220> FEATURE:
<223> OTHER INFORMATION: Antimicrobial peptide

<400> SEQUENCE: 208

Arg Arg Arg Trp Trp Trp Arg
1               5

```
<210> SEQ ID NO 209
<211> LENGTH: 7
<212> TYPE: PRT
<213> ORGANISM: Artificial
<220> FEATURE:
<223> OTHER INFORMATION: Antimicrobial peptide

<400> SEQUENCE: 209

Arg Trp Arg Trp Arg Trp Arg
1               5

<210> SEQ ID NO 210
<211> LENGTH: 7
<212> TYPE: PRT
<213> ORGANISM: Artificial
<220> FEATURE:
<223> OTHER INFORMATION: Antimicrobial peptide

<400> SEQUENCE: 210

Arg Arg Arg Phe Trp Trp Arg
1               5

<210> SEQ ID NO 211
<211> LENGTH: 7
<212> TYPE: PRT
<213> ORGANISM: Artificial
<220> FEATURE:
<223> OTHER INFORMATION: Antimicrobial peptide

<400> SEQUENCE: 211

Arg Arg Trp Trp Arg Arg Phe
1               5

<210> SEQ ID NO 212
<211> LENGTH: 7
<212> TYPE: PRT
<213> ORGANISM: Artificial
<220> FEATURE:
<223> OTHER INFORMATION: Antimicrobial peptide

<400> SEQUENCE: 212

Arg Arg Arg Trp Trp Trp Phe
1               5

<210> SEQ ID NO 213
<211> LENGTH: 7
<212> TYPE: PRT
<213> ORGANISM: Artificial
<220> FEATURE:
<223> OTHER INFORMATION: Antimicrobial peptide

<400> SEQUENCE: 213

Arg Trp Arg Trp Arg Trp Phe
1               5

<210> SEQ ID NO 214
<211> LENGTH: 7
<212> TYPE: PRT
<213> ORGANISM: Artificial
<220> FEATURE:
<223> OTHER INFORMATION: Antimicrobial peptide

<400> SEQUENCE: 214

Arg Arg Arg Arg Trp Trp Lys
1               5

<210> SEQ ID NO 215
```

```
<211> LENGTH: 7
<212> TYPE: PRT
<213> ORGANISM: Artificial
<220> FEATURE:
<223> OTHER INFORMATION: Antimicrobial peptide

<400> SEQUENCE: 215

Arg Arg Trp Trp Arg Arg Lys
1               5

<210> SEQ ID NO 216
<211> LENGTH: 7
<212> TYPE: PRT
<213> ORGANISM: Artificial
<220> FEATURE:
<223> OTHER INFORMATION: Antimicrobial peptide

<400> SEQUENCE: 216

Arg Arg Arg Trp Trp Trp Lys
1               5

<210> SEQ ID NO 217
<211> LENGTH: 7
<212> TYPE: PRT
<213> ORGANISM: Artificial
<220> FEATURE:
<223> OTHER INFORMATION: Antimicrobial peptide

<400> SEQUENCE: 217

Arg Trp Arg Trp Arg Trp Lys
1               5

<210> SEQ ID NO 218
<211> LENGTH: 7
<212> TYPE: PRT
<213> ORGANISM: Artificial
<220> FEATURE:
<223> OTHER INFORMATION: Antimicrobial peptide

<400> SEQUENCE: 218

Arg Arg Arg Lys Trp Trp Lys
1               5

<210> SEQ ID NO 219
<211> LENGTH: 7
<212> TYPE: PRT
<213> ORGANISM: Artificial
<220> FEATURE:
<223> OTHER INFORMATION: Antimicrobial peptide

<400> SEQUENCE: 219

Arg Arg Trp Lys Arg Arg Lys
1               5

<210> SEQ ID NO 220
<211> LENGTH: 7
<212> TYPE: PRT
<213> ORGANISM: Artificial
<220> FEATURE:
<223> OTHER INFORMATION: Antimicrobial peptide

<400> SEQUENCE: 220

Arg Arg Arg Lys Trp Trp Lys
1               5

<210> SEQ ID NO 221
<211> LENGTH: 7
```

```
<212> TYPE: PRT
<213> ORGANISM: Artificial
<220> FEATURE:
<223> OTHER INFORMATION: Antimicrobial peptide

<400> SEQUENCE: 221

Arg Trp Arg Lys Arg Trp Lys
1               5

<210> SEQ ID NO 222
<211> LENGTH: 14
<212> TYPE: PRT
<213> ORGANISM: Artificial
<220> FEATURE:
<223> OTHER INFORMATION: Antimicrobial peptide

<400> SEQUENCE: 222

Leu His Leu Leu His Gln Leu Leu His Leu Leu His Gln Phe
1               5                   10

<210> SEQ ID NO 223
<211> LENGTH: 14
<212> TYPE: PRT
<213> ORGANISM: Artificial
<220> FEATURE:
<223> OTHER INFORMATION: Antimicrobial peptide

<400> SEQUENCE: 223

Ala Gln Ala Ala His Gln Ala Ala His Ala Ala His Gln Phe
1               5                   10

<210> SEQ ID NO 224
<211> LENGTH: 14
<212> TYPE: PRT
<213> ORGANISM: Artificial
<220> FEATURE:
<223> OTHER INFORMATION: Antimicrobial peptide

<400> SEQUENCE: 224

Lys Leu Lys Lys Leu Leu Lys Lys Leu Lys Lys Leu Leu Lys
1               5                   10

<210> SEQ ID NO 225
<211> LENGTH: 14
<212> TYPE: PRT
<213> ORGANISM: Artificial
<220> FEATURE:
<223> OTHER INFORMATION: Antimicrobial peptide

<400> SEQUENCE: 225

Leu Lys Leu Leu Lys Lys Leu Leu Lys Leu Leu Lys Lys Phe
1               5                   10

<210> SEQ ID NO 226
<211> LENGTH: 14
<212> TYPE: PRT
<213> ORGANISM: Artificial
<220> FEATURE:
<223> OTHER INFORMATION: Antimicrobial peptide

<400> SEQUENCE: 226

Leu Gln Leu Leu Lys Gln Leu Leu Lys Leu Leu Lys Gln Phe
1               5                   10

<210> SEQ ID NO 227
<211> LENGTH: 14
<212> TYPE: PRT
```

<213> ORGANISM: Artificial
<220> FEATURE:
<223> OTHER INFORMATION: Antimicrobial peptide

<400> SEQUENCE: 227

Ala Gln Ala Ala Lys Gln Ala Ala Lys Ala Ala Lys Gln Phe
1               5                   10

<210> SEQ ID NO 228
<211> LENGTH: 14
<212> TYPE: PRT
<213> ORGANISM: Artificial
<220> FEATURE:
<223> OTHER INFORMATION: Antimicrobial peptide

<400> SEQUENCE: 228

Arg Trp Arg Arg Trp Trp Arg His Phe His His Phe Phe His
1               5                   10

<210> SEQ ID NO 229
<211> LENGTH: 14
<212> TYPE: PRT
<213> ORGANISM: Artificial
<220> FEATURE:
<223> OTHER INFORMATION: Antimicrobial peptide

<400> SEQUENCE: 229

Lys Leu Lys Lys Leu Leu Lys Arg Trp Arg Arg Trp Trp Arg
1               5                   10

<210> SEQ ID NO 230
<211> LENGTH: 14
<212> TYPE: PRT
<213> ORGANISM: Artificial
<220> FEATURE:
<223> OTHER INFORMATION: Antimicrobial peptide

<400> SEQUENCE: 230

Arg Trp Arg Arg Leu Leu Lys Lys Leu His His Leu Leu His
1               5                   10

<210> SEQ ID NO 231
<211> LENGTH: 14
<212> TYPE: PRT
<213> ORGANISM: Artificial
<220> FEATURE:
<223> OTHER INFORMATION: Antimicrobial peptide

<400> SEQUENCE: 231

Lys Leu Lys Lys Leu Leu Lys His Leu His His Leu Leu His
1               5                   10

<210> SEQ ID NO 232
<211> LENGTH: 15
<212> TYPE: PRT
<213> ORGANISM: Artificial
<220> FEATURE:
<223> OTHER INFORMATION: Antimicrobial peptide

<400> SEQUENCE: 232

Phe Val Phe Arg His Lys Trp Val Trp Lys His Arg Phe Leu Phe
1               5                   10                  15

<210> SEQ ID NO 233
<211> LENGTH: 15
<212> TYPE: PRT
<213> ORGANISM: Artificial

```
<220> FEATURE:
<223> OTHER INFORMATION: Antimicrobial peptide

<400> SEQUENCE: 233

Val Phe Ile His Arg His Val Trp Val His Lys His Val Leu Phe
1               5                   10                  15

<210> SEQ ID NO 234
<211> LENGTH: 15
<212> TYPE: PRT
<213> ORGANISM: Artificial
<220> FEATURE:
<223> OTHER INFORMATION: Antimicrobial peptide

<400> SEQUENCE: 234

Trp Arg Trp Arg Ala Arg Trp Arg Trp Arg Leu Arg Trp Arg Phe
1               5                   10                  15

<210> SEQ ID NO 235
<211> LENGTH: 15
<212> TYPE: PRT
<213> ORGANISM: Artificial
<220> FEATURE:
<223> OTHER INFORMATION: Antimicrobial peptide

<400> SEQUENCE: 235

Trp Arg Ile His Leu Arg Ala Arg Leu His Val Lys Phe Arg Phe
1               5                   10                  15

<210> SEQ ID NO 236
<211> LENGTH: 15
<212> TYPE: PRT
<213> ORGANISM: Artificial
<220> FEATURE:
<223> OTHER INFORMATION: Antimicrobial peptide

<400> SEQUENCE: 236

Leu Arg Ile His Ala Arg Phe Lys Val His Ile Arg Leu Lys Phe
1               5                   10                  15

<210> SEQ ID NO 237
<211> LENGTH: 15
<212> TYPE: PRT
<213> ORGANISM: Artificial
<220> FEATURE:
<223> OTHER INFORMATION: Antimicrobial peptide

<400> SEQUENCE: 237

Phe His Ile Lys Phe Arg Val His Leu Lys Val Arg Phe His Phe
1               5                   10                  15

<210> SEQ ID NO 238
<211> LENGTH: 15
<212> TYPE: PRT
<213> ORGANISM: Artificial
<220> FEATURE:
<223> OTHER INFORMATION: Antimicrobial peptide

<400> SEQUENCE: 238

Phe His Val Lys Ile His Phe Arg Leu His Val Lys Phe His Phe
1               5                   10                  15

<210> SEQ ID NO 239
<211> LENGTH: 15
<212> TYPE: PRT
<213> ORGANISM: Artificial
<220> FEATURE:
```

```
<223> OTHER INFORMATION: Antimicrobial peptide

<400> SEQUENCE: 239

Leu His Ile His Ala His Phe His Val His Ile His Leu His Phe
1               5                   10                  15

<210> SEQ ID NO 240
<211> LENGTH: 15
<212> TYPE: PRT
<213> ORGANISM: Artificial
<220> FEATURE:
<223> OTHER INFORMATION: Antimicrobial peptide

<400> SEQUENCE: 240

Phe Lys Ile His Phe Arg Leu Lys Val His Ile Arg Phe Lys Phe
1               5                   10                  15

<210> SEQ ID NO 241
<211> LENGTH: 15
<212> TYPE: PRT
<213> ORGANISM: Artificial
<220> FEATURE:
<223> OTHER INFORMATION: Antimicrobial peptide

<400> SEQUENCE: 241

Phe Lys Ala His Ile Arg Phe Lys Leu Arg Val Lys Phe His Phe
1               5                   10                  15

<210> SEQ ID NO 242
<211> LENGTH: 15
<212> TYPE: PRT
<213> ORGANISM: Artificial
<220> FEATURE:
<223> OTHER INFORMATION: Antimicrobial peptide

<400> SEQUENCE: 242

Leu Lys Ala Lys Ile Lys Phe Lys Val Lys Leu Lys Ile Lys Phe
1               5                   10                  15

<210> SEQ ID NO 243
<211> LENGTH: 14
<212> TYPE: PRT
<213> ORGANISM: Artificial
<220> FEATURE:
<223> OTHER INFORMATION: Antimicrobial peptide

<400> SEQUENCE: 243

Trp Ile Trp Lys His Lys Phe Leu His Arg His Phe Leu Phe
1               5                   10

<210> SEQ ID NO 244
<211> LENGTH: 14
<212> TYPE: PRT
<213> ORGANISM: Artificial
<220> FEATURE:
<223> OTHER INFORMATION: Antimicrobial peptide

<400> SEQUENCE: 244

Val Phe Leu His Arg His Val Ile Lys His Lys Leu Val Phe
1               5                   10

<210> SEQ ID NO 245
<211> LENGTH: 13
<212> TYPE: PRT
<213> ORGANISM: Artificial
<220> FEATURE:
<223> OTHER INFORMATION: Antimicrobial peptide
```

<400> SEQUENCE: 245

Phe Leu His Lys His Val Leu Arg His Arg Ile Val Phe
1               5                   10

<210> SEQ ID NO 246
<211> LENGTH: 13
<212> TYPE: PRT
<213> ORGANISM: Artificial
<220> FEATURE:
<223> OTHER INFORMATION: Antimicrobial peptide

<400> SEQUENCE: 246

Val Phe Lys His Lys Ile Val His Arg His Ile Leu Phe
1               5                   10

<210> SEQ ID NO 247
<211> LENGTH: 13
<212> TYPE: PRT
<213> ORGANISM: Artificial
<220> FEATURE:
<223> OTHER INFORMATION: Antimicrobial peptide

<400> SEQUENCE: 247

Phe Leu Phe Lys His Leu Phe Leu His Arg Ile Phe Phe
1               5                   10

<210> SEQ ID NO 248
<211> LENGTH: 12
<212> TYPE: PRT
<213> ORGANISM: Artificial
<220> FEATURE:
<223> OTHER INFORMATION: Antimicrobial peptide

<400> SEQUENCE: 248

Leu Phe Lys His Ile Leu Ile His Arg Val Ile Phe
1               5                   10

<210> SEQ ID NO 249
<211> LENGTH: 12
<212> TYPE: PRT
<213> ORGANISM: Artificial
<220> FEATURE:
<223> OTHER INFORMATION: Antimicrobial peptide

<400> SEQUENCE: 249

Phe Leu His Lys His Leu Phe Lys His Lys Leu Phe
1               5                   10

<210> SEQ ID NO 250
<211> LENGTH: 12
<212> TYPE: PRT
<213> ORGANISM: Artificial
<220> FEATURE:
<223> OTHER INFORMATION: Antimicrobial peptide

<400> SEQUENCE: 250

Val Phe Arg His Arg Phe Ile His Arg His Val Phe
1               5                   10

<210> SEQ ID NO 251
<211> LENGTH: 12
<212> TYPE: PRT
<213> ORGANISM: Artificial
<220> FEATURE:
<223> OTHER INFORMATION: Antimicrobial peptide

```
<400> SEQUENCE: 251

Phe Ile His Lys Leu Val His Lys His Val Leu Phe
1               5                   10

<210> SEQ ID NO 252
<211> LENGTH: 12
<212> TYPE: PRT
<213> ORGANISM: Artificial
<220> FEATURE:
<223> OTHER INFORMATION: Antimicrobial peptide

<400> SEQUENCE: 252

Val Leu Arg His Leu Phe Arg His Arg Ile Val Phe
1               5                   10

<210> SEQ ID NO 253
<211> LENGTH: 12
<212> TYPE: PRT
<213> ORGANISM: Artificial
<220> FEATURE:
<223> OTHER INFORMATION: Antimicrobial peptide

<400> SEQUENCE: 253

Leu Val His Lys Leu Ile Leu Arg His Leu Leu Phe
1               5                   10

<210> SEQ ID NO 254
<211> LENGTH: 12
<212> TYPE: PRT
<213> ORGANISM: Artificial
<220> FEATURE:
<223> OTHER INFORMATION: Antimicrobial peptide

<400> SEQUENCE: 254

Val Phe Lys Arg Val Leu Ile His Lys Leu Ile Phe
1               5                   10

<210> SEQ ID NO 255
<211> LENGTH: 12
<212> TYPE: PRT
<213> ORGANISM: Artificial
<220> FEATURE:
<223> OTHER INFORMATION: Antimicrobial peptide

<400> SEQUENCE: 255

Ile Val Arg Lys Phe Leu Phe Arg His Lys Val Phe
1               5                   10

<210> SEQ ID NO 256
<211> LENGTH: 12
<212> TYPE: PRT
<213> ORGANISM: Artificial
<220> FEATURE:
<223> OTHER INFORMATION: Antimicrobial peptide

<400> SEQUENCE: 256

Val Leu Lys His Val Ile Ala His Lys Arg Leu Phe
1               5                   10

<210> SEQ ID NO 257
<211> LENGTH: 11
<212> TYPE: PRT
<213> ORGANISM: Artificial
<220> FEATURE:
<223> OTHER INFORMATION: Antimicrobial peptide

<400> SEQUENCE: 257
```

```
Phe Ile Arg Lys Phe Leu Phe Lys His Leu Phe
1               5                   10
```

<210> SEQ ID NO 258
<211> LENGTH: 11
<212> TYPE: PRT
<213> ORGANISM: Artificial
<220> FEATURE:
<223> OTHER INFORMATION: Antimicrobial peptide

<400> SEQUENCE: 258

```
Val Ile Arg His Val Trp Val Arg Lys Leu Phe
1               5                   10
```

<210> SEQ ID NO 259
<211> LENGTH: 13
<212> TYPE: PRT
<213> ORGANISM: Artificial
<220> FEATURE:
<223> OTHER INFORMATION: Antimicrobial peptide

<400> SEQUENCE: 259

```
Phe Leu Phe Arg His Arg Phe Arg His Arg Leu Val Phe
1               5                   10
```

<210> SEQ ID NO 260
<211> LENGTH: 13
<212> TYPE: PRT
<213> ORGANISM: Artificial
<220> FEATURE:
<223> OTHER INFORMATION: Antimicrobial peptide

<400> SEQUENCE: 260

```
Leu Phe Leu His Lys His Ala Lys His Lys Phe Leu Phe
1               5                   10
```

<210> SEQ ID NO 261
<211> LENGTH: 11
<212> TYPE: PRT
<213> ORGANISM: Artificial
<220> FEATURE:
<223> OTHER INFORMATION: Antimicrobial peptide

<400> SEQUENCE: 261

```
Phe Lys His Lys Phe Lys His Lys Phe Ile Phe
1               5                   10
```

<210> SEQ ID NO 262
<211> LENGTH: 11
<212> TYPE: PRT
<213> ORGANISM: Artificial
<220> FEATURE:
<223> OTHER INFORMATION: Antimicrobial peptide

<400> SEQUENCE: 262

```
Leu Arg His Arg Leu Arg His Arg Leu Ile Phe
1               5                   10
```

<210> SEQ ID NO 263
<211> LENGTH: 11
<212> TYPE: PRT
<213> ORGANISM: Artificial
<220> FEATURE:
<223> OTHER INFORMATION: Antimicrobial peptide

<400> SEQUENCE: 263

```
Leu Ile Leu Lys Phe Leu Phe Lys Phe Val Phe
1               5                   10
```

<210> SEQ ID NO 264
<211> LENGTH: 11
<212> TYPE: PRT
<213> ORGANISM: Artificial
<220> FEATURE:
<223> OTHER INFORMATION: Antimicrobial peptide

<400> SEQUENCE: 264

```
Val Leu Ile Arg Ile Leu Val Arg Val Ile Phe
1               5                   10
```

<210> SEQ ID NO 265
<211> LENGTH: 9
<212> TYPE: PRT
<213> ORGANISM: Artificial
<220> FEATURE:
<223> OTHER INFORMATION: Antimicrobial peptide

<400> SEQUENCE: 265

```
Phe Arg His Arg Phe Arg His Arg Phe
1               5
```

<210> SEQ ID NO 266
<211> LENGTH: 9
<212> TYPE: PRT
<213> ORGANISM: Artificial
<220> FEATURE:
<223> OTHER INFORMATION: Antimicrobial peptide

<400> SEQUENCE: 266

```
Leu Lys His Lys Leu Lys His Lys Phe
1               5
```

<210> SEQ ID NO 267
<211> LENGTH: 9
<212> TYPE: PRT
<213> ORGANISM: Artificial
<220> FEATURE:
<223> OTHER INFORMATION: Antimicrobial peptide

<400> SEQUENCE: 267

```
Phe Lys Phe Lys His Lys Leu Ile Phe
1               5
```

<210> SEQ ID NO 268
<211> LENGTH: 9
<212> TYPE: PRT
<213> ORGANISM: Artificial
<220> FEATURE:
<223> OTHER INFORMATION: Antimicrobial peptide

<400> SEQUENCE: 268

```
Leu Arg Leu Arg His Arg Val Leu Phe
1               5
```

<210> SEQ ID NO 269
<211> LENGTH: 9
<212> TYPE: PRT
<213> ORGANISM: Artificial
<220> FEATURE:
<223> OTHER INFORMATION: Antimicrobial peptide

<400> SEQUENCE: 269

```
Phe Lys Phe Leu Phe Lys Phe Leu Phe
```

```
1               5
```

<210> SEQ ID NO 270
<211> LENGTH: 9
<212> TYPE: PRT
<213> ORGANISM: Artificial
<220> FEATURE:
<223> OTHER INFORMATION: Antimicrobial peptide

<400> SEQUENCE: 270

```
Leu Arg Leu Phe Leu Arg Trp Leu Phe
1               5
```

<210> SEQ ID NO 271
<211> LENGTH: 9
<212> TYPE: PRT
<213> ORGANISM: Artificial
<220> FEATURE:
<223> OTHER INFORMATION: Antimicrobial peptide

<400> SEQUENCE: 271

```
Phe Lys Phe Leu Phe Lys His Lys Phe
1               5
```

<210> SEQ ID NO 272
<211> LENGTH: 9
<212> TYPE: PRT
<213> ORGANISM: Artificial
<220> FEATURE:
<223> OTHER INFORMATION: Antimicrobial peptide

<400> SEQUENCE: 272

```
Leu Arg Leu Phe Leu Arg His Arg Phe
1               5
```

<210> SEQ ID NO 273
<211> LENGTH: 7
<212> TYPE: PRT
<213> ORGANISM: Artificial
<220> FEATURE:
<223> OTHER INFORMATION: Antimicrobial peptide

<400> SEQUENCE: 273

```
Phe Lys Phe Leu Phe Lys Phe
1               5
```

<210> SEQ ID NO 274
<211> LENGTH: 7
<212> TYPE: PRT
<213> ORGANISM: Artificial
<220> FEATURE:
<223> OTHER INFORMATION: Antimicrobial peptide

<400> SEQUENCE: 274

```
Leu Arg Leu Phe Leu Arg Phe
1               5
```

<210> SEQ ID NO 275
<211> LENGTH: 14
<212> TYPE: PRT
<213> ORGANISM: Artificial
<220> FEATURE:
<223> OTHER INFORMATION: Antimicrobial peptide

<400> SEQUENCE: 275

```
His His Phe Phe His His Phe His His Phe Phe His His Phe
1               5                   10
```

<210> SEQ ID NO 276
<211> LENGTH: 14
<212> TYPE: PRT
<213> ORGANISM: Artificial
<220> FEATURE:
<223> OTHER INFORMATION: Antimicrobial peptide

<400> SEQUENCE: 276

Phe His Phe Phe His His Phe Phe His Phe Phe His His Phe
1               5                   10

<210> SEQ ID NO 277
<211> LENGTH: 21
<212> TYPE: PRT
<213> ORGANISM: Artificial
<220> FEATURE:
<223> OTHER INFORMATION: Antimicrobial peptide

<400> SEQUENCE: 277

Lys Leu Leu Lys Gly Ala Thr Phe His Phe Phe His His Phe Phe His
1               5                   10                  15

Phe Phe His His Phe
            20

<210> SEQ ID NO 278
<211> LENGTH: 18
<212> TYPE: PRT
<213> ORGANISM: Artificial
<220> FEATURE:
<223> OTHER INFORMATION: Antimicrobial peptide

<400> SEQUENCE: 278

Lys Leu Leu Lys Phe His Phe Phe His His Phe Phe His Phe Phe His
1               5                   10                  15

His Phe

<210> SEQ ID NO 279
<211> LENGTH: 18
<212> TYPE: PRT
<213> ORGANISM: Artificial
<220> FEATURE:
<223> OTHER INFORMATION: Antimicrobial peptide

<400> SEQUENCE: 279

Phe His Phe Phe His His Phe Phe His Phe Phe His His Phe Lys Leu
1               5                   10                  15

Leu Lys

<210> SEQ ID NO 280
<211> LENGTH: 7
<212> TYPE: PRT
<213> ORGANISM: Artificial
<220> FEATURE:
<223> OTHER INFORMATION: Antimicrobial peptide

<400> SEQUENCE: 280

Tyr Ser Pro Trp Thr Asn Phe
1               5

<210> SEQ ID NO 281
<211> LENGTH: 37
<212> TYPE: PRT
<213> ORGANISM: Artificial
<220> FEATURE:

-continued

<223> OTHER INFORMATION: Antimicrobial peptide

<400> SEQUENCE: 281

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser
        35

<210> SEQ ID NO 282
<211> LENGTH: 38
<212> TYPE: PRT
<213> ORGANISM: Artificial
<220> FEATURE:
<223> OTHER INFORMATION: Antimicrobial peptide

<400> SEQUENCE: 282

Cys Leu Leu Gly Asp Phe Phe Arg Lys Ser Lys Glu Lys Ile Gly Lys
1               5                   10                  15

Glu Phe Lys Arg Ile Val Gln Arg Ile Lys Asp Phe Leu Arg Asn Leu
            20                  25                  30

Val Pro Arg Thr Glu Ser
        35

<210> SEQ ID NO 283
<211> LENGTH: 16
<212> TYPE: PRT
<213> ORGANISM: Artificial
<220> FEATURE:
<223> OTHER INFORMATION: Antimicrobial peptide

<400> SEQUENCE: 283

Phe Lys Arg Ile Val Gln Arg Ile Lys Asp Phe Leu Arg Asn Leu Val
1               5                   10                  15

<210> SEQ ID NO 284
<211> LENGTH: 39
<212> TYPE: PRT
<213> ORGANISM: Artificial
<220> FEATURE:
<223> OTHER INFORMATION: Antimicrobial peptide

<400> SEQUENCE: 284

Cys Leu Leu Gly Asp Phe Phe Arg Lys Ser Lys Glu Lys Ile Gly Lys
1               5                   10                  15

Glu Phe Lys Arg Ile Val Gln Arg Ile Lys Asp Phe Leu Arg Asn Leu
            20                  25                  30

Val Pro Arg Thr Glu Ser Cys
        35

<210> SEQ ID NO 285
<211> LENGTH: 13
<212> TYPE: PRT
<213> ORGANISM: Artificial
<220> FEATURE:
<223> OTHER INFORMATION: Antimicrobial peptide

<400> SEQUENCE: 285

Phe Lys Arg Ile Val Gln Arg Ile Lys Asp Phe Leu Arg
1               5                   10

<210> SEQ ID NO 286

```
<211> LENGTH: 21
<212> TYPE: PRT
<213> ORGANISM: Artificial
<220> FEATURE:
<223> OTHER INFORMATION: Antimicrobial peptide

<400> SEQUENCE: 286

Phe Lys Arg Ile Val Gln Arg Ile Lys Asp Phe Leu Arg Asn Leu Val
1               5                   10                  15

Pro Arg Thr Glu Ser
            20

<210> SEQ ID NO 287
<211> LENGTH: 21
<212> TYPE: PRT
<213> ORGANISM: Artificial
<220> FEATURE:
<223> OTHER INFORMATION: Antimicrobial peptide

<400> SEQUENCE: 287

Gly Lys Glu Phe Lys Arg Ile Val Gln Arg Ile Lys Asp Phe Leu Arg
1               5                   10                  15

Asn Leu Val Pro Arg
            20

<210> SEQ ID NO 288
<211> LENGTH: 20
<212> TYPE: PRT
<213> ORGANISM: Artificial
<220> FEATURE:
<223> OTHER INFORMATION: Antimicrobial peptide

<400> SEQUENCE: 288

Lys Arg Ile Val Gln Arg Ile Lys Asp Phe Leu Arg Asn Leu Val Pro
1               5                   10                  15

Arg Thr Glu Ser
            20

<210> SEQ ID NO 289
<211> LENGTH: 21
<212> TYPE: PRT
<213> ORGANISM: Artificial
<220> FEATURE:
<223> OTHER INFORMATION: Antimicrobial peptide

<400> SEQUENCE: 289

Leu Leu Gly Asp Phe Phe Arg Lys Ser Lys Glu Lys Ile Gly Lys Glu
1               5                   10                  15

Phe Lys Arg Ile Val
            20

<210> SEQ ID NO 290
<211> LENGTH: 31
<212> TYPE: PRT
<213> ORGANISM: Artificial
<220> FEATURE:
<223> OTHER INFORMATION: Antimicrobial peptide

<400> SEQUENCE: 290

Arg Lys Ser Lys Glu Lys Ile Gly Lys Glu Phe Lys Arg Ile Val Gln
1               5                   10                  15

Arg Ile Lys Asp Phe Leu Arg Asn Leu Val Pro Arg Thr Glu Ser
            20                  25                  30
```

-continued

```
<210> SEQ ID NO 291
<211> LENGTH: 21
<212> TYPE: PRT
<213> ORGANISM: Artificial
<220> FEATURE:
<223> OTHER INFORMATION: Antimicrobial peptide

<400> SEQUENCE: 291

Ser Lys Glu Lys Ile Gly Lys Glu Phe Lys Arg Ile Val Gln Arg Ile
1               5                   10                  15

Lys Asp Phe Leu Arg
            20

<210> SEQ ID NO 292
<211> LENGTH: 38
<212> TYPE: PRT
<213> ORGANISM: Artificial
<220> FEATURE:
<223> OTHER INFORMATION: Antimicrobial peptide

<400> SEQUENCE: 292

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser Cys
        35

<210> SEQ ID NO 293
<211> LENGTH: 11
<212> TYPE: PRT
<213> ORGANISM: Artificial
<220> FEATURE:
<223> OTHER INFORMATION: Antimicrobial peptide

<400> SEQUENCE: 293

Lys Leu Phe Lys Phe Leu Arg Lys His Leu Leu
1               5                   10

<210> SEQ ID NO 294
<211> LENGTH: 13
<212> TYPE: PRT
<213> ORGANISM: Artificial
<220> FEATURE:
<223> OTHER INFORMATION: Antimicrobial peptide

<400> SEQUENCE: 294

Phe Leu Lys Phe Leu Lys Lys Phe Phe Lys Lys Leu Lys
1               5                   10

<210> SEQ ID NO 295
<211> LENGTH: 16
<212> TYPE: PRT
<213> ORGANISM: Artificial
<220> FEATURE:
<223> OTHER INFORMATION: Antimicrobial peptide

<400> SEQUENCE: 295

Phe Ile Gly Ala Ile Ala Arg Leu Leu Ser Lys Ile Phe Gly Lys Arg
1               5                   10                  15

<210> SEQ ID NO 296
<211> LENGTH: 18
<212> TYPE: PRT
<213> ORGANISM: Artificial
<220> FEATURE:
```

<223> OTHER INFORMATION: Antimicrobial peptide

<400> SEQUENCE: 296

Gly Ile Phe Ser Lys Leu Ala Gly Lys Lys Ile Lys Asn Leu Leu Ile
1               5                   10                  15

Ser Gly

<210> SEQ ID NO 297
<211> LENGTH: 21
<212> TYPE: PRT
<213> ORGANISM: Artificial
<220> FEATURE:
<223> OTHER INFORMATION: Antimicrobial peptide

<400> SEQUENCE: 297

Gly Ile Phe Ser Lys Leu Ala Gly Lys Lys Ile Lys Asn Leu Leu Ile
1               5                   10                  15

Ser Gly Leu Lys Gly
            20

<210> SEQ ID NO 298
<211> LENGTH: 20
<212> TYPE: PRT
<213> ORGANISM: Artificial
<220> FEATURE:
<223> OTHER INFORMATION: Antimicrobial peptide

<400> SEQUENCE: 298

Gly Leu Phe Ser Lys Phe Val Gly Lys Gly Ile Lys Asn Phe Leu Ile
1               5                   10                  15

Lys Gly Val Lys
            20

<210> SEQ ID NO 299
<211> LENGTH: 19
<212> TYPE: PRT
<213> ORGANISM: Artificial
<220> FEATURE:
<223> OTHER INFORMATION: Antimicrobial peptide

<400> SEQUENCE: 299

Lys Ala Tyr Ser Thr Pro Arg Cys Lys Gly Leu Phe Arg Ala Leu Met
1               5                   10                  15

Cys Trp Leu

<210> SEQ ID NO 300
<211> LENGTH: 19
<212> TYPE: PRT
<213> ORGANISM: Artificial
<220> FEATURE:
<223> OTHER INFORMATION: Antimicrobial peptide

<400> SEQUENCE: 300

Lys Ile Phe Gly Ala Ile Trp Pro Leu Ala Leu Gly Ala Leu Lys Asn
1               5                   10                  15

Leu Ile Lys

<210> SEQ ID NO 301
<211> LENGTH: 25
<212> TYPE: PRT
<213> ORGANISM: Artificial
<220> FEATURE:
<223> OTHER INFORMATION: Antimicrobial peptide

```
<400> SEQUENCE: 301

Gly Trp Gly Ser Phe Lys Lys Ala Ala His Val Gly Lys His Val
1               5                   10                  15

Gly Lys Ala Ala Leu Thr His Tyr Leu
            20                  25

<210> SEQ ID NO 302
<211> LENGTH: 18
<212> TYPE: PRT
<213> ORGANISM: Artificial
<220> FEATURE:
<223> OTHER INFORMATION: Antimicrobial peptide

<400> SEQUENCE: 302

Arg Gly Leu Arg Arg Leu Gly Arg Lys Ile Ala His Gly Val Lys Lys
1               5                   10                  15

Tyr Gly

<210> SEQ ID NO 303
<211> LENGTH: 29
<212> TYPE: PRT
<213> ORGANISM: Artificial
<220> FEATURE:
<223> OTHER INFORMATION: Antimicrobial peptide

<400> SEQUENCE: 303

Arg Gly Leu Arg Arg Leu Gly Arg Lys Ile Ala His Gly Val Lys Lys
1               5                   10                  15

Tyr Gly Pro Thr Val Leu Arg Ile Ile Arg Ile Ala Gly
            20                  25

<210> SEQ ID NO 304
<211> LENGTH: 18
<212> TYPE: PRT
<213> ORGANISM: Artificial
<220> FEATURE:
<223> OTHER INFORMATION: Antimicrobial peptide

<400> SEQUENCE: 304

Lys Ile Ala His Gly Val Lys Lys Tyr Gly Pro Thr Val Leu Arg Ile
1               5                   10                  15

Ile Arg

<210> SEQ ID NO 305
<211> LENGTH: 37
<212> TYPE: PRT
<213> ORGANISM: Artificial
<220> FEATURE:
<223> OTHER INFORMATION: Antimicrobial peptide

<400> SEQUENCE: 305

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser
        35

<210> SEQ ID NO 306
<211> LENGTH: 13
<212> TYPE: PRT
<213> ORGANISM: Artificial
<220> FEATURE:
```

<223> OTHER INFORMATION: Antimicrobial peptide

<400> SEQUENCE: 306

Phe Leu Pro Leu Ile Gly Arg Val Leu Ser Gly Ile Leu
1               5                   10

<210> SEQ ID NO 307
<211> LENGTH: 21
<212> TYPE: PRT
<213> ORGANISM: Artificial
<220> FEATURE:
<223> OTHER INFORMATION: Antimicrobial peptide

<400> SEQUENCE: 307

Ile Gly Lys Phe Leu Lys Lys Ala Lys Lys Phe Gly Lys Ala Phe Val
1               5                   10                  15

Lys Ile Leu Lys Lys
            20

<210> SEQ ID NO 308
<211> LENGTH: 18
<212> TYPE: PRT
<213> ORGANISM: Artificial
<220> FEATURE:
<223> OTHER INFORMATION: Antimicrobial peptide

<400> SEQUENCE: 308

Gly Lys Phe Leu Lys Lys Ala Lys Lys Phe Gly Lys Ala Phe Val Lys
1               5                   10                  15

Ile Leu

<210> SEQ ID NO 309
<211> LENGTH: 15
<212> TYPE: PRT
<213> ORGANISM: Artificial
<220> FEATURE:
<223> OTHER INFORMATION: Antimicrobial peptide

<400> SEQUENCE: 309

Trp Phe Leu Lys Phe Leu Lys Lys Phe Phe Lys Lys Leu Lys Tyr
1               5                   10                  15

<210> SEQ ID NO 310
<211> LENGTH: 17
<212> TYPE: PRT
<213> ORGANISM: Artificial
<220> FEATURE:
<223> OTHER INFORMATION: Antimicrobial peptide

<400> SEQUENCE: 310

Arg Gly Leu Arg Arg Leu Gly Arg Lys Ile Ala His Gly Val Lys Lys
1               5                   10                  15

Tyr

<210> SEQ ID NO 311
<211> LENGTH: 13
<212> TYPE: PRT
<213> ORGANISM: Artificial
<220> FEATURE:
<223> OTHER INFORMATION: Antimicrobial peptide

<400> SEQUENCE: 311

Leu Leu Gly Asp Phe Phe Arg Lys Ser Lys Glu Lys Ile
1               5                   10

<210> SEQ ID NO 312
<211> LENGTH: 12
<212> TYPE: PRT
<213> ORGANISM: Artificial
<220> FEATURE:
<223> OTHER INFORMATION: Antimicrobial peptide

<400> SEQUENCE: 312

Ile Leu Arg Trp Pro Trp Trp Pro Trp Arg Arg Lys
1               5                   10

<210> SEQ ID NO 313
<211> LENGTH: 19
<212> TYPE: PRT
<213> ORGANISM: Artificial
<220> FEATURE:
<223> OTHER INFORMATION: Antimicrobial peptide

<400> SEQUENCE: 313

Lys Leu Phe Gly Ala Leu Trp Pro Leu Ala Leu Gly Ala Leu Lys Asn
1               5                   10                  15

Leu Leu Lys

<210> SEQ ID NO 314
<211> LENGTH: 16
<212> TYPE: PRT
<213> ORGANISM: Artificial
<220> FEATURE:
<223> OTHER INFORMATION: Mutated novispirin G10

<400> SEQUENCE: 314

Lys Asn Leu Arg Ile Ile Arg Lys Gly Ile His Ile Ile Lys Lys Tyr
1               5                   10                  15

<210> SEQ ID NO 315
<211> LENGTH: 5
<212> TYPE: PRT
<213> ORGANISM: Artificial
<220> FEATURE:
<223> OTHER INFORMATION: Peptide linker

<400> SEQUENCE: 315

Pro Ser Gly Ser Pro
1               5

<210> SEQ ID NO 316
<211> LENGTH: 5
<212> TYPE: PRT
<213> ORGANISM: Artificial
<220> FEATURE:
<223> OTHER INFORMATION: Peptide linker

<400> SEQUENCE: 316

Ala Ser Ala Ser Ala
1               5

<210> SEQ ID NO 317
<211> LENGTH: 15
<212> TYPE: PRT
<213> ORGANISM: Artificial
<220> FEATURE:
<223> OTHER INFORMATION: Peptide linker

<400> SEQUENCE: 317

Gly Gly Gly Gly Ser Gly Gly Gly Ser Gly Gly Gly Gly Ser
1               5                   10                  15

```
<210> SEQ ID NO 318
<211> LENGTH: 4
<212> TYPE: PRT
<213> ORGANISM: Artificial
<220> FEATURE:
<223> OTHER INFORMATION: Peptide linker

<400> SEQUENCE: 318

Gly Gly Gly Gly
1

<210> SEQ ID NO 319
<211> LENGTH: 5
<212> TYPE: PRT
<213> ORGANISM: Artificial
<220> FEATURE:
<223> OTHER INFORMATION: Peptide linker

<400> SEQUENCE: 319

Pro Ser Pro Ser Pro
1               5

<210> SEQ ID NO 320
<211> LENGTH: 5
<212> TYPE: PRT
<213> ORGANISM: Artificial
<220> FEATURE:
<223> OTHER INFORMATION: Peptide linker

<400> SEQUENCE: 320

Pro Ser Pro Ser Pro
1               5

<210> SEQ ID NO 321
<211> LENGTH: 4
<212> TYPE: PRT
<213> ORGANISM: Artificial
<220> FEATURE:
<223> OTHER INFORMATION: Peptide linker

<400> SEQUENCE: 321

Lys Lys Lys Lys
1

<210> SEQ ID NO 322
<211> LENGTH: 4
<212> TYPE: PRT
<213> ORGANISM: Artificial
<220> FEATURE:
<223> OTHER INFORMATION: Peptide linker

<400> SEQUENCE: 322

Arg Arg Arg Arg
1

<210> SEQ ID NO 323
<211> LENGTH: 5
<212> TYPE: PRT
<213> ORGANISM: Artificial
<220> FEATURE:
<223> OTHER INFORMATION: Peptide linker

<400> SEQUENCE: 323

Ala Ser Ala Ser Ala
1               5
```

<210> SEQ ID NO 324
<211> LENGTH: 6
<212> TYPE: PRT
<213> ORGANISM: Artificial
<220> FEATURE:
<223> OTHER INFORMATION: Peptide linker

<400> SEQUENCE: 324

Gly Gly Ser Gly Gly Ser
1               5

<210> SEQ ID NO 325
<211> LENGTH: 5
<212> TYPE: PRT
<213> ORGANISM: Artificial
<220> FEATURE:
<223> OTHER INFORMATION: Peptide linker

<400> SEQUENCE: 325

Gly Gly Gly Gly Ser
1               5

<210> SEQ ID NO 326
<211> LENGTH: 10
<212> TYPE: PRT
<213> ORGANISM: Artificial
<220> FEATURE:
<223> OTHER INFORMATION: Peptide linker

<400> SEQUENCE: 326

Gly Gly Gly Gly Ser Gly Gly Gly Gly Ser
1               5                   10

<210> SEQ ID NO 327
<211> LENGTH: 15
<212> TYPE: PRT
<213> ORGANISM: Artificial
<220> FEATURE:
<223> OTHER INFORMATION: Peptide linker

<400> SEQUENCE: 327

Gly Gly Gly Gly Ser Gly Gly Gly Gly Ser Gly Gly Gly Gly Ser
1               5                   10                  15

<210> SEQ ID NO 328
<211> LENGTH: 20
<212> TYPE: PRT
<213> ORGANISM: Artificial
<220> FEATURE:
<223> OTHER INFORMATION: Peptide linker

<400> SEQUENCE: 328

Gly Gly Gly Gly Ser Gly Gly Gly Gly Ser Gly Gly Gly Gly Ser Gly
1               5                   10                  15

Gly Gly Gly Ser
            20

<210> SEQ ID NO 329
<211> LENGTH: 25
<212> TYPE: PRT
<213> ORGANISM: Artificial
<220> FEATURE:
<223> OTHER INFORMATION: Peptide linker

<400> SEQUENCE: 329

Gly Gly Gly Gly Ser Gly Gly Gly Gly Ser Gly Gly Gly Gly Ser Gly

```
                1               5              10              15
Gly Gly Gly Ser Gly Gly Gly Ser
                20              25

<210> SEQ ID NO 330
<211> LENGTH: 30
<212> TYPE: PRT
<213> ORGANISM: Artificial
<220> FEATURE:
<223> OTHER INFORMATION: Peptide linker

<400> SEQUENCE: 330

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
                20              25                  30
```

DENTAL STRIPS FOR THE DELIVERY OF SPECIFICALLY TARGETED ANTIMICROBIAL PEPTIDES

CROSS-REFERENCE TO RELATED APPLICATIONS

This application is a U.S. 371 National Phase of PCT/US2018/027357, filed on Apr. 12, 2018, which claims benefit of and priority to U.S. Ser. No. 62/485,793, filed on Apr. 14, 2017, both of which are incorporated herein by reference in their entirety for all purposes.

STATEMENT OF GOVERNMENTAL SUPPORT

[Not Applicable]

INCORPORATION BY REFERENCE OF SEQUENCE LISTING PROVIDED AS A TEXT FILE

This application contains references to nucleic acid sequences that have been submitted concurrently herewith as the sequence listing text file "C3JN-P028US_ST25.txt", file size 80.3 kb, created on Nov. 19, 2021, which is incorporated by reference in its entirety pursuant to 37 C.F.R. § 1.52(e)(5).

BACKGROUND

Products by which various oral care substances or actives can be delivered to the soft and hard tissues of the oral cavity have previously been known. Examples of such oral care products include, for example, brushing aids such as dentifrice products for delivery of anti-caries agents such as fluoride for the reduction of the bacteria that lead to the formation of plaque, and mouthwashes containing breath freshening agents and/or enamel hardening agents, and the like. In addition, bleaching agents such as peroxide that can be applied directly to the surfaces of the teeth, i.e., to the tooth enamel, have been developed.

Sheet-like substrates for administration of oral treatments have been known for some time. A variety of advantages are achieved with such substrates, such as ease of handling, storage and packaging. Use of such sheet-like substrates has typically been limited to the application of whitening substances to the enamel surfaces of the teeth or for the application of desensitizing agents.

It has been found that many such product forms typically do not provide delivery kinetics for positively charged antimicrobial peptides, or antimicrobials, or remineralization agents that maintain agent activity on the hard and soft oral tissues for a period of time sufficient to enhance or prolong the desired therapeutic, prophylactic, and/or cosmetic benefits.

SUMMARY

In various embodiments dental strips that preserve the efficacy and stability of antimicrobial peptides and that deliver such peptides at therapeutically relevant levels are provided. In various embodiments the dental strips additionally or alternatively deliver remineralization, enamel hardening, and/or various positively charged antimicrobial agents, preserving the stability and efficacy of such agents at therapeutically relevant levels for a sufficient time period. It was discovered that various specifically targeted antimicrobial peptides (STAMPs) and/or simple antimicrobial peptides (AMPs) have bioactivity profiles that are dependent on release kinetics that achieve a local high concentration for the efficacy of such peptides when incorporated into dental strips. In certain embodiments desirable release kinetics for a STAMP and/or AMP achieve a local $C_{max}$ concentration of peptide at an oral surface preferably in about 1 minute to 3 hours (after application of the dental strip), or in about 15 minutes to 1 hour, or in about 30 minutes to 1 hour, or about 30 minutes. Accordingly, in certain embodiments, methods and devices (e.g., dental strips) described herein provide for long-term peptide stability and high activity of STAMPs and/or AMPs into dental strips. The dental strips are conveniently applied to tooth surfaces and act to reduce or prevent the formation of dental carries.

In certain embodiments a dental strip is provided that includes a film backing, and a delivery layer comprising one or more specifically targeted antimicrobial peptides (or in certain embodiments simple antimicrobial peptides), on one surface of the film backing. In certain embodiments the delivery layer additionally functions as an adhesive layer that affixes the dental strip to the tooth surface. In certain embodiments the delivery layer comprises one or more polymers that may or may not be water soluble (dissolvable) and/or water-swellable.

Also provided herein are methods of delivering specifically targeted antimicrobial peptides (or in certain embodiments simple antimicrobial peptides) to the surface of a tooth, or gum in an oral cavity. In certain embodiments the method comprises applying a dental strip to teeth in a mammal (e.g., a human subject or a non-human mammal) where the dental strip comprises one or more specifically targeted antimicrobial peptides as described herein (or simple antimicrobial peptides). The dental strip is fabricated to deliver effective doses of the specifically targeted antimicrobial peptide (or simple antimicrobial peptide) over a time frame sufficient that such treatments provide a reduction in the incidence or severity of dental caries and/or prevent the formation of dental caries.

Various embodiments cnetemplated herein may include, but need not be limited to, one or more of the following:

Embodiment 1: A dental strip for the delivery of effective amounts of specifically targeted antimicrobial peptides, said dental strip comprising:
an orally compatible backing layer; and
a delivery layer disposed on one surface of said backing layer wherein said delivery layer comprises an orally compatible polymer, or combination of polymers, and a specifically targeted antimicrobial peptide capable of binding and killing *Streptococcus mutans*.

Embodiment 2: The dental strip of embodiment 1, wherein said delivery layer is distributed on said backing layer as a plurality of dots or regions.

Embodiment 3: The dental strip of embodiment 1, wherein said delivery layer is distributed on said backing layer as a substantially continuous layer.

Embodiment 4: The dental strip according to any one of embodiments 1-3, wherein said delivery or adhesive layer (e.g., dots or layer) range in thickness from about 20 μm up to about 500 μm.

Embodiment 5: The dental strip according to any one of embodiments 1-3, wherein said delivery layer contains said specifically targeted antimicrobial peptide at an amount ranging from about 0.1 mg/cm$^2$ up to about 20.0 mg/cm$^2$ of dental strip.

Embodiment 6: The dental strip according to any one of embodiments 1-3, wherein said dental strip contains a total amount of specifically targeted antimicrobial peptide ranging from about 0.969 mg/strip, or from about 1.94 mg/strip, or from about 4 mg/strip or from about 8 mg/strip up to about 50 mg/strip, or up to about 40 mg/strip, or up to about 30 mg/strip, or up to about 20 mg/strip., and/or comprises about 9.2 mg/strip or about 18.4 mg/strip, or about 36.8 mg/strip, or about 73.6 mg/strip, or about 147.2 mg/strip, or about 193.8 mg/strip, or about 387.6 mg/strip.

Embodiment 7: The dental strip according to any one of embodiments 1-6, wherein said dental strip, when applied to a tooth surface delivers sufficient specifically targeted antimicrobial peptide to kill or to inhibit the growth and/or proliferation of *S. mutans* on said tooth surface and/or adjacent gums.

Embodiment 8: The dental strip according to any one of embodiments 1-7, wherein said delivery layer is provided on said strip in a substantially dry form.

Embodiment 9: The dental strip according to any one of embodiments 1-8, wherein the orally compatible polymer comprising said delivery layer is hydratable and/or dissolvable in the mouth.

Embodiment 10: The dental strip of embodiment 9, wherein the orally compatible polymer dissolves over a period of time ranging from about 1 minute or from about 2 minutes or from about 5 minutes, or from about 10 minutes up to about 1 hour, or up to about 45 minutes, or up to about 30 minutes, or up to about 20 minutes.

Embodiment 11: The dental strip according to any one of embodiments 1-10, wherein the orally compatible polymer comprising said delivery layer comprises a material selected from the group consisting of hydroxyethylcellulose, hydroxypropylcellulose, polyvinylacetate, polylactic acid, polyethylene glycol, polyurethanes, methacrylate/acrylate co-polymers and/or their esters.

Embodiment 12: The dental strip of embodiment 11, wherein the orally compatible polymer comprising said delivery layer comprises (hydroxypropyl) methylcellulose, or a methacrylate/acrylate copolymers and their esters.

Embodiment 13: The dental strip of embodiment 11, wherein the orally compatible polymer comprising said delivery layer comprises polyvinylpyrrolidone.

Embodiment 14: The dental strip according to any one of embodiments 1-13, wherein the MW of the orally compatible polymer(s) ranges from about 3000 to about 2,000,000, or about 300,000 to about 400,000.

Embodiment 15: The dental strip according to any one of embodiments 1-14, wherein said backing layer is water permeable.

Embodiment 16: The dental strip of embodiment 15, wherein said backing layer comprises one or more materials selected from the group consisting of hydroxypropylmethylcellulose, hydroxypropylcellulose, hydroxyethylcellulose, and polyethylene glycol.

Embodiment 17: The dental strip according to any one of embodiments 1-14, wherein said backing layer is water impermeable.

Embodiment 18: The dental strip of embodiment 17, wherein said backing layer comprises a material selected from the group consisting of ethyl cellulose, propyl cellulose, polyethylene, polypropylene, polyolefin, polyurethane, polyethylene terephthalate, polylactic acid, polyacrylates, and ethylene vinyl acetate.

Embodiment 19: The dental strip according to any one of embodiments 1-18, wherein the molecular weight of polymers comprising said backing layer ranges from about 18,000 to 300,000, or from about 60,000 to about 200,000, and/or where the backing layer comprises ethylcellulose and the ethylcellulose has a viscosity of 90 to 110 mPa*s as a 5% solution in 80% toluene, 20% ethanol.

Embodiment 20: The dental strip according to any one of embodiments 1-19, wherein the backing layer contains a plasticizer.

Embodiment 21: The dental strip of embodiment 20, wherein said plasticizer comprise a material selected from the group consisting of castor oil, triethyl citrate, glycerine triacetate, dibutyl sebacate, parabens, and isopropyl myristate.

Embodiment 22: The dental strip of embodiment 21, wherein said backing layer comprises ethyl cellulose and castor oil.

Embodiment 23: The dental strip of embodiment 22, wherein said backing layer comprises ethyl cellulose at an amount ranging from about 5 to 80% (w/w), or from about 10 to 80% (w/w), or about 67.5% (w/w), and castor oil at an amount ranging from about 1 to about 60% (w/w), or from about 5% to about 40% (w/w), or about 37.5% (w/w).

Embodiment 24: The dental strip according to any one of embodiments 1-23, wherein said backing layer ranges in thickness from about 5 µm to about 500 µm, or from about 15 µm to about 50 µm.

Embodiment 25: The dental strip according to any one of embodiments 1-24, wherein a release liner film is disposed on said delivery layer.

Embodiment 26: The dental strip of embodiment 25, wherein said release liner can be peeled from the underlying delivery layer without substantially removing said delivery layer from said backing layer.

Embodiment 27: The dental strip according to any one of embodiments 25-26, wherein said release liner comprises a material selected from the group consisting of polyethylene, polypropylene, various polyurethanes, polyethylene terephthalate, various other polyesters, polytetrafluoroethylene, polysiloxanes, and combinations thereof.

Embodiment 28: The dental strip of embodiment 27, wherein said release liner comprises a polyethylene terephthalate and polytetrafluoroethylene film.

Embodiment 29: The dental strip according to any one of embodiments 25-28, wherein said release liner ranges in thickness from about 10 µm to about 200 µm, or about 25 µm to about 100 µm, or about 80 µm.

Embodiment 30: The dental strip according to any one of embodiments 1-29, wherein said delivery layer further comprises a colorant.

Embodiment 31: The dental strip according to any one of embodiments 1-30, wherein said delivery layer further comprises a flavor agent.

Embodiment 32: The dental strip according to any one of embodiments 1-31, wherein said dental strip comprises: about 90 mg to 100 mg polyvinylpyrrolidone; and about 5 mg to about 390 mg specifically targeted antimicrobial peptide.

Embodiment 33: The dental strip of embodiment 32, wherein said dental strip comprises about 3 mg to about 4 mg sucralose.

Embodiment 34: The dental strip according to any one of embodiments 32-33, wherein said dental strip comprises about 25 mg to about 30 mg flavoring agent.

Embodiment 35: The dental strip according to any one of embodiments 32-34, wherein said backing layer comprises ethylcellulose with a viscosity of 90 to 110 mPa*s as a 5% solution in 80% toluene, 20% ethanol.

Embodiment 36: The dental strip according to any one of embodiments 32-35, wherein said dental strip comprise a release liner disposed on said delivery layer wherein said release liner comprises a polyethylene terephthalate and polytetrafluoroethylene film.

Embodiment 37: The dental strip according to any one of embodiments 32-36, wherein the delivery layer comprise a formulation selected from the group consisting of:

| Component | Function | Amount per Strip |
|---|---|---|
| Specifically targeted antimicrobial peptide | Active Agent | 9.2 mg |
| Polyvinylpyrrolidone, K90 | Polymer | 94.7 mg |
| Sucralose, NF | Flavoring Agent | 3.2 mg |
| Cool Mint Flavor | Flavoring agent | 26.3 mg |
| FD&C Blue No. 1 | Coloring Agent | 0.1 mg, |

| Component | Function | Strip |
|---|---|---|
| Specifically targeted antimicrobial peptide | Active Agent | 18.4 mg |
| Polyvinylpyrrolidone, K90 | Polymer | 94.7 mg |
| Sucralose, NF | Flavoring Agent | 3.2 mg |
| Cool Mint Flavor | Flavoring agent | 26.3 mg |
| FD&C Blue No. 1 | Coloring Agent | 0.1 mg, | and

| Component | Function | Amount per strip |
|---|---|---|
| Specifically targeted antimicrobial peptide | Active Agent | 36.8 mg |
| Polyvinylpyrrolidone, K90 | Polymer | 95.7 mg |
| Sucralose, NF | Flavoring Agent | 3.7 mg |
| Cool Mint Flavor | Flavoring agent | 26.1 mg |
| FD&C Blue No. 1 | Coloring Agent | 0.1 mg. |

Embodiment 38: The dental strip according to any one of embodiments 1-37, wherein said specifically targeted antimicrobial peptide comprises a targeting peptide that binds *Streptococcus mutans* and said targeting peptide is attached to an antimicrobial peptide directly or through an amino acid or a peptide linker.

Embodiment 39: The dental strip of embodiment 38, wherein the sequence of said specifically targeted antimicrobial peptide comprises or consists of the amino acid sequence TFFRLFNRSFTQALGKGGGKNLRIIRKGI-HIIKKY (SEQ ID NO:1).

Embodiment 40: The dental strip of embodiment 39, wherein said specifically targeted antimicrobial peptide is amidated at the carboxyl terminus.

Embodiment 41: The dental strip of embodiment 38, wherein said targeting peptide comprises a peptide that ranges in length from 5 amino acid, or from 6 amino acids, or from 7 amino acids, or from 8 amino acids up to about 50 amino acids, or up to about 40 amino acids, or up to about 30 amino acids, or up to about 20 amino acids.

Embodiment 42: The dental strip according to any one of embodiments 38 or 41, wherein said targeting peptide comprises or consists of an amino acid sequence selected from the group consisting of SGSLSTFFRLFNRSFTQALGK (CSP, SEQ ID NO:5) or a fragment thereof, EMRL-SKFFRDFILQRKK (CSP1, (SEQ ID NO:6) or a fragment thereof, and EMRISRIILDFLFLRKK (CSP2, (SEQ ID NO:7), NIFEYFLE (SEQ ID NO:8). or a fragment thereof.

Embodiment 43: The dental strip according to any one of embodiments 38 or 41, wherein the amino acid sequence of said targeting peptide comprises or consists of the amino acid sequence TFFRLFNR and comprises at least 8, or at least 9, or at least 10, or at least 11, or at least 12, or at least 13, or at least 14, or at least 15, or at least 16, or at least 17, or at least 18, or at least 19, or at least 20, or 21 contiguous amino acids of CSP.

Embodiment 44: The dental strip of embodiment 43, wherein the amino acid sequence of said targeting peptide comprises or consists of an amino acid sequence selected from the group consisting of TFFRLFNR (SEQ ID NO:9), TFFRLFNRS (SEQ ID NO:10), TFFRLFNRS (SEQ ID NO:11), TFFRLFNRSF (SEQ ID NO:12), TFFRLFNRSFT (SEQ ID NO:13), TFFRLFNRSFTQ (SEQ ID NO:14), TFFRLFNRSFTQA (SEQ ID NO:15), TFFRLFNRSFTQAL (SEQ ID NO:16), TFFRLFNRSFTQALG (SEQ ID NO:17), TFFRLFNRSFTQALGK (SEQ ID NO:18), STFFRLFNR (SEQ ID NO:19), STFFRLFNRS (SEQ ID NO:20), STFFRLFNRS (SEQ ID NO:21), STFFRLFNRSF (SEQ ID NO:22), STFFRLFNRSFT (SEQ ID NO:23), STFFRLFNRSFTQ (SEQ ID NO:24), STFFRLFNRSFTQA (SEQ ID NO:25), STFFRLFNRSFTQAL (SEQ ID NO:26), STFFRLFNRSFTQALG (SEQ ID NO:27), STFFRLFNRSFTQALGK (SEQ ID NO:28), LSTFFRLFNR (SEQ ID NO:29), LSTFFRLFNRS (SEQ ID NO:30), LSTFFRLFNRS (SEQ ID NO:31), LSTFFRLFNRSF (SEQ ID NO:32), LSTFFRLFNRSFT (SEQ ID NO:33), LSTFFRLFNRSFTQ (SEQ ID NO:34), LSTFFRLFNRSFTQA (SEQ ID NO:35), LSTFFRLFNRSFTQAL (SEQ ID NO:36), LSTFFRLFNRSFTQALG (SEQ ID NO:37), LSTFFRLFNRSFTQALGK (SEQ ID NO:38), SLSTFFRLFNR (SEQ ID NO:39), SLSTFFRLFNRS (SEQ ID NO:40), SLSTFFRLFNRS (SEQ ID NO:41), SLSTFFRLFNRSF (SEQ ID NO:42), SLSTFFRLFNRSFT (SEQ ID NO:43), SLSTFFRLFNRSFTQ (SEQ ID NO:44), SLSTFFRLFNRSFTQA (SEQ ID NO:45), SLSTFFRLFNRSFTQAL (SEQ ID NO:46), SLSTFFRLFNRSFTQALG (SEQ ID NO:47), SLSTFFRLFNRSFTQALGK (SEQ ID NO:48), GSL-STFFRLFNR (SEQ ID NO:49), GSLSTFFRLFNRS (SEQ ID NO:50), GSLSTFFRLFNRS (SEQ ID NO:51), GSL-STFFRLFNRSF (SEQ ID NO:52), GSLSTFFRLFNRSFT (SEQ ID NO:53), GSLSTFFRLFNRSFTQ (SEQ ID NO:54), GSLSTFFRLFNRSFTQA (SEQ ID NO:55), GSL-STFFRLFNRSFTQAL (SEQ ID NO:56), GSL-STFFRLFNRSFTQALG (SEQ ID NO:57), GSL-STFFRLFNRSFTQALGK (SEQ ID NO:58), SGSLSTFFRLFNR (SEQ ID NO:59), SGSLSTFFRLFNRS (SEQ ID NO:60), SGSLSTFFRLFNRS (SEQ ID NO:61), SGSLSTFFRLFNRSF (SEQ ID NO:62), SGSL-STFFRLFNRSFT (SEQ ID NO:63), SGSL-STFFRLFNRSFTQ (SEQ ID NO:64), SGSL-STFFRLFNRSFTQA (SEQ ID NO:65), SGSLSTFFRLFNRSFTQAL (SEQ ID NO:66), and SGSL-STFFRLFNRSFTQALG (SEQ ID NO:67).

Embodiment 45: The dental strip according to any one of embodiments 38 or 41, wherein said targeting peptide comprises or consists of the amino acid sequence $$X^1-X^2-F-R-X^5-X^6-X^7-R-X^9-X^{10}-X^{11}-X^{12}-X^{13}-X^{14}-X^{15}-X^{16}$$ (SEQ ID NO:68)

or the inverse of said amino acid sequence, wherein:
$X^1$ is a polar amino acid, or A;
$X^2$ is F, W, Q, A, or an analog thereof;
$X^5$ is a hydrophobic amino acid;

$X^6$ is a hydrophobic amino acid, N, Q, or an analog thereof;
$X^7$ is a polar amino acid, A, F, or an analog thereof;
$X^9$ is a polar amino acid, A or an analog thereof;
$X^{10}$ is a hydrophobic amino acid, Q, A, or an analog thereof;
$X^{11}$ is a hydrophobic amino acid;
$X^{12}$ is Q, A, or an analog thereof;
$X^{13}$ is a non-polar amino acid;
$X^{14}$ is a hydrophobic amino acid;
$X^{15}$ is a non-polar amino acid, N, S, D, or an analog thereof;
$X^{16}$ is a polar amino acid, F, A, or an analog thereof, and said peptide ranges in length up to 100 amino acids.

Embodiment 46: The dental strip of embodiment 45, wherein $X^1$ is A or T.

Embodiment 47: The dental strip according to any one of embodiments 45-46, wherein $X^2$ is F, W, Q, or A.

Embodiment 48: The dental strip of embodiment 47, wherein $X^2$ is F.

Embodiment 49: The dental strip according to any one of embodiments 45-48, wherein $X^5$ is L, A, or an analogue thereof.

Embodiment 50: The dental strip of embodiment 49, wherein $X^5$ is L.

Embodiment 51: The dental strip according to any one of embodiments 45-50, wherein $X^6$ is F, L, N, A, Q, or an analog thereof.

Embodiment 52: The dental strip of embodiment 51, wherein $X^6$ is a hydrophobic amino acid.

Embodiment 53: The dental strip of embodiment 51, wherein $X^6$ is F.

Embodiment 54: The dental strip according to any one of embodiments 45-53, wherein $X^7$ is a polar amino acid, A, or F.

Embodiment 55: The dental strip of embodiment 54, wherein $X^7$ is a polar amino acid or A.

Embodiment 56: The dental strip of embodiment 54, wherein $X^7$ is N, A, S, D, or F.

Embodiment 57: The dental strip of embodiment 54, wherein $X^7$ is N or A.

Embodiment 58: The dental strip of embodiment 54, wherein $X^7$ is N.

Embodiment 59: The dental strip according to any one of embodiments 45-58, wherein $X^9$ is a polar amino acid, or A.

Embodiment 60: The dental strip of embodiment 59, wherein $X^9$ is S or A.

Embodiment 61: The dental strip of embodiment 59, wherein $X^9$ is S.

Embodiment 62: The dental strip according to any one of embodiments 45-61, wherein $X^{10}$ is a hydrophobic amino acid, Q, or A.

Embodiment 63: The dental strip of embodiment 62, wherein $X^{10}$ is a hydrophobic amino acid.

Embodiment 64: The dental strip of embodiment 63, wherein $X^{10}$ is F, L, or an analog thereof.

Embodiment 65: The dental strip of embodiment 63, wherein $X^{10}$ is F.

Embodiment 66: The dental strip according to any one of embodiments 45-65, wherein $X^{11}$ is T, A, or an analog thereof.

Embodiment 67: The dental strip of embodiment 66, wherein $X^{11}$ is T.

Embodiment 68: The dental strip according to any one of embodiments 45-67, wherein $X^{12}$ is Q or A.

Embodiment 69: The dental strip of embodiment 68, wherein $X^{12}$ is Q.

Embodiment 70: The dental strip according to any one of embodiments 45-69, wherein $X^{13}$ is P, A, or an analog thereof.

Embodiment 71: The dental strip of embodiment 70, wherein $X^{13}$ is A.

Embodiment 72: The dental strip according to any one of embodiments 45-71, wherein $X^{14}$ is L, A, or an analog thereof.

Embodiment 73: The dental strip of embodiment 72, wherein $X^{14}$ is L.

Embodiment 74: The dental strip according to any one of embodiments 45-73, wherein $X^{15}$ is a non-polar amino acid, N, S, or D.

Embodiment 75: The dental strip of embodiment 74, wherein $X^{15}$ is G, A, F, N, S, D, or an analog thereof.

Embodiment 76: The dental strip of embodiment 75, wherein $X^{15}$ is G, or A.

Embodiment 77: The dental strip according to any one of embodiments 45-76, wherein $X^{16}$ is $X^{16}$ is a polar amino acid, F, or A.

Embodiment 78: The dental strip of embodiment 77, wherein $X^{16}$ is a polar amino acid.

Embodiment 79: The dental strip of embodiment 78, wherein $X^{16}$ is K, Q, or an analog thereof.

Embodiment 80: The dental strip of embodiment 78, wherein $X^{16}$ is K.

Embodiment 81: The dental strip according to any one of embodiments 45-80, wherein said peptide does not comprise the amino acid sequence TFFRLFNRSFTQALGK.

Embodiment 82: The dental strip of embodiment 45, wherein said peptide comprises or consists of an amino acid sequence selected from the group consisting of AFFRAFNRAFAQALAK (SEQ ID NO:70), TFFRAFARAFAQAAAK (SEQ ID NO:71), AFFRAFARAFAQALAK (SEQ ID NO:72), AFFRLFARAFAQAAAK (SEQ ID NO:73), TLFRLLNRSLTQALGK (SEQ ID NO:74), TFFRLFNRSFTQALFK (SEQ ID NO:75), TFFRLFNRSLTQALGK (SEQ ID NO:76), TFFRLFNRSFTQALNK (SEQ ID NO:77), AFFRAFARAFAQAAAK (SEQ ID NO:78), AFFRAFNRAFAQAAAK (SEQ ID NO:79), TFFRLFNRSFTQALSK (SEQ ID NO:80), AFFRAFARSFAQAAAK (SEQ ID NO:81), AFFRAFARAFAQAAGK (SEQ ID NO:82), AFFRAFARAFTQAAAK (SEQ ID NO:83), TFFRLFNRSFTQALGQ (SEQ ID NO:84), TFFRLLNRSFTQALGK (SEQ ID NO:85), TWFRLFNRSFTQALGK (SEQ ID NO:86), AFFRAFARAFAQAFAK (SEQ ID NO:87), TQFRLFNRSFTQALGK (SEQ ID NO:88), TFFRLFNRSFTQALDK (SEQ ID NO:89), TFFRLFNRSFTQALAK (SEQ ID NO:90), TFFRLFNRSFTQALGE (SEQ ID NO:91), TFFRLFSRSFTQALGK (SEQ ID NO:92), TFFRLFNRSFTQALGA (SEQ ID NO:93), TFFRLFDRSFTQALGK (SEQ ID NO:94), TFFRLFNRSFTQALGF (SEQ ID NO:95), TFFRAFARSFTQAAAK (SEQ ID NO:96), TFFRLFARSFTQAAGK (SEQ ID NO:97), TFFRLFNRSFTQ L K (SEQ ID NO:98), TFFRLFNRSFTQALGS (SEQ ID NO:99), TLFRLFNRSFTQALGK (SEQ ID NO:100), TFFRLNFRSFTQALGK (SEQ ID NO:101), TFFRLFNRSQTQALGK (SEQ ID NO:102), TFFRLFAAAFTQALGK (SEQ ID NO:103), TFFRLFNRSFTQALGK (SEQ ID NO:104), TFFRLFNRSAAAALGK (SEQ ID NO:105), TFFRLFFRSNTQALGK* (SEQ ID NO:106), TFFRLFNRSFTQPLGK (SEQ ID NO:107), TAFRLANRSATQALGK (SEQ ID NO:108), TFFRLFNRSFTQAAAA (SEQ ID NO:109), TFFRLQNRSFTQALGK (SEQ ID NO:110), TFFRLFNRSFTQALPK (SEQ ID NO:111), TYYRLFNRSFTQALGK (SEQ ID NO:112), TFFRLF RSFTQALGK (SEQ ID NO:113), and TQFRLQNR- SQTQALGK (SEQ ID NO:114).

Embodiment 83: The dental strip according to any one of embodiments 45-82, wherein the amino acid sequence of said peptide is the inverse of said sequence.

Embodiment 84: The dental strip according to any one of embodiments 45-83, wherein said targeting peptide ranges in length up to 50 amino acids or up to 25 amino acids, or up to 20 amino acids.

Embodiment 85: The dental strip according to any one of embodiments 45-84, wherein said targeting peptide is an "L" peptide.

Embodiment 86: The dental strip according to any one of embodiments 45-84, wherein said targeting peptide is a "D" peptide.

Embodiment 87: The dental strip according to any one of embodiments 45-84, wherein said targeting peptide is a beta peptide.

Embodiment 88: The dental strip according to any one of embodiments 38, and 40-87, wherein said targeting peptide is attached to an antimicrobial peptide comprising or consisting of an amino acid sequence found in Table 3.

Embodiment 89: The dental strip according to any one of embodiments 38, and 40-87, wherein said targeting peptide is attached to an antimicrobial peptide comprising or consisting of an amino acid sequence selected from the group consisting of G2 KNLRIIRKGIHIIKKY* (SEQ ID NO:115), Novispirin G10 KNLRRIIRKGIHIIKKYG (SEQ ID NO:116), Novispirin T10 KNLRRIIRKTIHIIKKYG (SEQ ID NO:117), Novispirin G7 KNLRRIGRKIIHIIK-KYG (SEQ ID NO:118), Novispirin T7 KNLRRITRKII-HIIKKYG (SEQ ID NO:119), Ovispirin KNLRRIIRKII-HIIKKYG (SEQ ID NO:120), PGG GLLRRLRKKIGEIFKKYG (SEQ ID NO:121), Protegrin-1 RGGRLCYCRRRFCVCVGR* (SEQ ID NO:122), K-1 GLGRVIGRLIKQIIWRR (SEQ ID NO:123), K-2 VYRKRKSILKIYAKLKGWH (SEQ ID NO:124), K-7 NYRLVNAIFSKIFKKKFIKF (SEQ ID NO:125), K-8 KILKFLFKKVF (SEQ ID NO:126), K-9 FIRKFLKKWLL (SEQ ID NO:127), K-10 KLFKFLRKHLL (SEQ ID NO:128), K-11 KILKFLFKQVF (SEQ ID NO:129), K-12 KILKKLFKFVF (SEQ ID NO:130), K-13 GILKKLFTKVF (SEQ ID NO:131), K-14 LRKFLHKLF (SEQ ID NO:132), K-15 LRKNLRWLF (SEQ ID NO:133), K-16 FIRKFLQKLHL (SEQ ID NO:134), K-17 FTRKFLKFLHL (SEQ ID NO:135), K-18 KKFKKFKVLKIL (SEQ ID NO:136), K-19 LLKLLKLKKLKF (SEQ ID NO:137), K-20 FLKFLKKFFKKLKY (SEQ ID NO:138), K-21 GWLKMFKKIIGKFGKF (SEQ ID NO:139), K-22 GIFKKFVKILYKVQKL (SEQ ID NO:140), and B-33 FKKFWKWFRRF (SEQ ID NO:174).

Embodiment 90: The dental strip according to any one of embodiments 38, and 40-89, wherein said targeting peptide and/or said antimicrobial peptide is an "L" peptide.

Embodiment 91: The dental strip according to any one of embodiments 38, and 40-89, wherein said targeting peptide and/or said antimicrobial peptide is a "D" peptide.

Embodiment 92: The dental strip according to any one of embodiments 38, and 40-89, wherein said targeting peptide and/or said antimicrobial peptide is a beta peptide.

Embodiment 93: The dental strip according to any one of embodiments 38, and 40-92, wherein said targeting peptide is chemically conjugated to said antimicrobial peptide.

Embodiment 94: The dental strip of embodiment 93, wherein said targeting peptide is chemically conjugated to said antimicrobial peptide via a linker.

Embodiment 95: The dental strip of embodiment 94, wherein said targeting peptide is chemically conjugated to said effector via a linker comprising a polyethylene glycol (PEG) or a non-peptide linker found in Table 4.

Embodiment 96: The dental strip according to any one of embodiments 38, and 40-92, wherein said targeting peptide is attached directly to said antimicrobial peptide (i.e., without a linker).

Embodiment 97: The dental strip according to any one of embodiments 38, and 40-92, wherein said targeting peptide is attached to said antimicrobial peptide via a peptide linkage.

Embodiment 98: The dental strip of embodiment 97, wherein said effector comprises an antimicrobial peptide and said construct is a fusion protein.

Embodiment 99: The dental strip according to any one of embodiments 97 and 98, wherein said targeting peptide is attached to said antimicrobial peptide by a peptide linker comprising or consisting of an amino acid sequence found in Table 4.

Embodiment 100: The dental strip of embodiment 99, wherein said peptide linker comprises or consists of the amino acid sequence GGG.

Embodiment 101: The dental strip according to any one of embodiments 38, and 40-100, wherein said peptide bears no terminal protecting groups.

Embodiment 102: The dental strip according to any one of embodiments 45-100, wherein said specifically targeted antimicrobial peptide bears one or more protecting groups.

Embodiment 103: The dental strip of embodiment 102, wherein said one or more protecting groups are independently selected from the group consisting of acetyl, amide, 3 to 20 carbon alkyl groups, Fmoc, Tboc, 9-fluoreneacetyl group, 1-fluorenecarboxylic group, 9-florenecarboxylic group, 9-fluorenone-1-carboxylic group, benzyloxycarbonyl, Xanthyl (Xan), Trityl (Trt), 4-methyltrityl (Mtt), 4-methoxytrityl (Mmt), 4-methoxy-2,3,6-trimethyl-benzenesulphonyl (Mtr), Mesitylene-2-sulphonyl (Mts), 4,4-dimethoxybenzhydryl (Mbh),Tosyl (Tos), 2,2,5,7,8-pentamethyl chroman-6-sulphonyl (Pmc), 4-methylbenzyl (MeBzl), 4-methoxybenzyl (MeOBzl), Benzyloxy (BzlO), Benzyl (Bzl), Benzoyl (Bz), 3-nitro-2-pyridinesulphenyl (Npys), 1-(4,4-dimentyl-2,6-diaxocyclohexylidene)ethyl (Dde), 2,6-dichlorobenzyl (2,6-DiCl-Bzl), 2-chlorobenzyloxycarbonyl (2-Cl—Z), 2-bromobenzyloxycarbonyl (2-Br-Z), Benzyloxymethyl (Bom), t-butoxycarbonyl (Boc), cyclohexyloxy (cHxO),t-butoxymethyl (Bum), t-butoxy (tBuO), t-Butyl (tBu), and Trifluoroacetyl (TFA).

Embodiment 104: The dental strip of embodiment 102, wherein said specifically targeted antimicrobial peptide comprises a protecting group at a carboxyl and/or amino terminus.

Embodiment 105: The dental strip of embodiment 104, wherein a carboxyl terminus is amidated.

Embodiment 106: The dental strip according to any one of embodiments 1-105, wherein said dental strip contains a fluoride.

Embodiment 107: The dental strip of embodiment 106, wherein said fluoride is disposed in said delivery layer.

Embodiment 108: The dental strip according to any one of embodiments 106-107, wherein said fluoride comprises an agent selected from the group consisting of sodium fluoride, stannous fluoride, sodium monofluorophosphate, zinc hexafluorosilicate, sodium hexafluorosilicate, ammonium fluoride, calcium fluoro-phosphate ($Ca_5[F(PO_4)_3]$) or fluorapatite, fluorine-doped hydroxyapatite (e.g., $Ca_5(PO_4)_3$(OH,F), calcium fluoride ($CaF_2$) or fluorite or fluorspar, diofluorisilane, $TiF_4$, and acidulated fluoride.

Embodiment 109: The dental strip according to any one of embodiments 1-108, wherein said dental strip additionally contains a positively charged compound that is antimicrobial and/or that promotes remineralization.

Embodiment 110: The dental strip of embodiment 109, wherein said dental strip contains a compound selected from the group consisting of cetylpyridinium chloride, benzalkonium chloride, chlorhexidine, polyhexamethylene biguanide (PHMB), cationic antimicrobial nanoparticles, bleach, synthetic peptides comprising a single DSS or ESS or repeats of DSS or ESS, dentin-sialophosphoprotein (DSP), dentin phosphoprotein, Arg-calcium carbonate, and xylitol.

Embodiment 111: A method of reducing or preventing the formation of dental caries disease in a mammal, said method comprising applying a dental strip according to any one of embodiments 1-110 to the teeth of said mammal.

Embodiment 112: The method of embodiment 111, wherein said applying comprises applying said strip with said delivery layer on the tooth surface and pressing and/or shaping dental strip until strip remains on a tooth surface.

Embodiment 113: The method according to any one of embodiments 111-112, wherein said dental strip comprises a release liner and said applying comprises removing said release liner and prior to application of the dental strip to said teeth.

Embodiment 114: The method according to any one of embodiments 111-113, wherein said mammal is a human.

Embodiment 115: The method according to any one of embodiments 111-113, wherein said mammal is a human infant.

Embodiment 116: The method according to any one of embodiments 111-113, wherein said mammal is a non-human mammal.

Embodiment 117: The method according to any one of embodiments 111-116, wherein said dental strip is retained on teeth for a period of time ranging from about 1 minute or from about 2 minutes or from about 5 minutes, or from about 10 minutes up to about 1 hour, or up to about 45 minutes, or up to about 30 minutes, or up to about 20 minutes.

Embodiment 118: A kit comprising: a container containing a dental strip according to any one of embodiments 1-105.

Embodiment 119: The kit of embodiment 118, wherein said kit contains 2 to 36, or 2 to 30, or 2 to 24, or 2 to 18 strips, and includes strips to cover upper and lower molars and bicuspids.

Embodiment 120: The kit of embodiment 119, wherein said kit contains 4 strips.

Embodiment 121: The kit of embodiment 119, wherein a package in said kit contains 4 strips.

Definitions

A "dental strip" or "dental strips" refer to one or more flexible substrates onto or into which are disposed one or more active agent(s) that are to be delivered to the surface(s) of one or more teeth. In certain embodiments the dental strips are configured so that they adhere to the tooth surface and provide delivery of the active agent(s) over a period of time (e.g., 5 or 10 minutes up to 1, 2, 3, or 4 hours). In certain embodiments dental strips are fabricated to attach to and deliver one or more active agent(s) to the facial and/or lingual surfaces and/or occlusal surface(s) of the teeth. In certain embodiments one or more dental strips are designed to deliver active agent(s) to one or more surface(s) of incisors, and/or cuspids, and/or bicuspids, and/or molars. In various embodiments the dental strips contemplated herein expressly exclude whitening agents.

The terms "subject," "individual," and "patient" may be used interchangeably and refer to humans, the as well as non-human mammals (e.g., non-human primates, canines, equines, felines, porcines, bovines, ungulates, lagomorphs, and the like). In various embodiments, the subject can be a human (e.g., adult male, adult female, adolescent male, adolescent female, male child, female child) under the care of a physician or other health worker in a hospital, as an outpatient, or other clinical context. In certain embodiments, the subject may not be under the care or prescription of a physician or other health worker.

The term "peptide" as used herein refers to a polymer of amino acid residues typically ranging in length from 2 to about 50 or about 60 residues. In certain embodiments the peptide ranges in length from about 2, 3, 4, 5, 7, 9, 10, or 11 residues to about 60, 50, 45, 40, 45, 30, 25, 20, or 15 residues. In certain embodiments the peptide ranges in length from about 8, 9, 10, 11, or 12 residues to about 15, 20 or 25 residues. In certain embodiments the amino acid residues comprising the peptide are "L-form" amino acid residues, however, it is recognized that in various embodiments, "D" amino acids can be incorporated into the peptide. Peptides also include amino acid polymers in which one or more amino acid residues is an artificial chemical analogue of a corresponding naturally occurring amino acid, as well as to naturally occurring amino acid polymers. In addition, the term applies to amino acids joined by a peptide linkage or by other, "modified linkages" (e.g., where the peptide bond is replaced by an α-ester, a β-ester, a thioamide, sulfonamide or phosphoramide, carbamate or carbonate, hydroxylate, and the like (see, e.g., Spatola, (1983) *Chem. Biochem. Amino Acids and Proteins* 7: 267-357), where the amide is replaced with a saturated amine (see, e.g., Skiles et al., U.S. Pat. No. 4,496,542, which is incorporated herein by reference, and Kaltenbronn et al., (1990) Pp. 969-970 in Proc. 11th American Peptide Symposium, ESCOM Science Publishers, The Netherlands, and the like)).

The term "residue"" as used herein refers to natural, synthetic, or modified amino acids. Various amino acid analogues include, but are not limited to 2-aminoadipic acid, 3-aminoadipic acid, beta-alanine (beta-aminopropionic acid), 2-aminobutyric acid, 4-aminobutyric acid, piperidinic acid, 6-aminocaproic acid, 2-aminoheptanoic acid, 2-aminoisobutyric acid, 3-aminoisobutyric acid, 2-aminopimelic acid, 2,4 diaminobutyric acid, desmosine, 2,2'-diaminopimelic acid, 2,3-diaminopropionic acid, N-ethylglycine, N-ethylasparagine, hydroxylysine, allo-hydroxylysine, 3-hydroxyproline, 4-hydroxyproline, isodesmosine, allo-isoleucine, N-methylglycine, sarcosine, N-methylisoleucine, 6-N-methyllysine, N-methylvaline, norvaline, norleucine, ornithine, and the like. These modified amino acids are illustrative and not intended to be limiting.

"β-peptides" comprise of "β amino acids", which have their amino group bonded to the β carbon rather than the α-carbon as in the 20 standard biological amino acids. The only commonly naturally occurring β amino acid is β-alanine.

Peptoids, or N-substituted glycines, are a specific subclass of peptidomimetics. They are closely related to their natural peptide counterparts, but differ chemically in that their side chains are appended to nitrogen atoms along the molecule's backbone, rather than to the α-carbons (as they are in natural amino acids).

The terms "conventional" and "natural" as applied to peptides herein refer to peptides, constructed only from the naturally-occurring amino acids: Ala, Cys, Asp, Glu, Phe, Gly, His, Ile, Lys, Leu, Met, Asn, Pro, Gln, Arg, Ser, Thr, Val, Trp, and Tyr. A compound of the invention "corresponds" to a natural peptide if it elicits a biological activity (e.g., antimicrobial activity) related to the biological activity and/or specificity of the naturally occurring peptide. The elicited activity may be the same as, greater than or less than that of the natural peptide. In general, such a peptoid will have an essentially corresponding monomer sequence, where a natural amino acid is replaced by an N-substituted glycine derivative, if the N-substituted glycine derivative resembles the original amino acid in hydrophilicity, hydrophobicity, polarity, etc. The following are illustrative, but non-limiting N-substituted glycine replacements: N-(1-methylprop-1-yl) glycine substituted for isoleucine (Ile), N-(prop-2-yl) glycine for valine (Val), N-benzylglycine for phenylanlaine (Phe), N-(2-hydroxyethyl) glycine for serine (Ser), and the like. In certain embodiments substitutions need not be "exact". Thus for example, in certain embodiments N-(2-hydroxyethyl) glycine may substitute for Ser, Thr, Cys, and/or Met; N-(2-methylprop-1-yl)glycine may substitute for Val, Leu, and/or Ile. In certain embodiments N-(2-hydroxyethyl) glycine can be used to substitute for Thr and Ser, despite the structural differences: the side chain in N-(2-hydroxyethyl)glycine is one methylene group longer than that of Ser, and differs from Thr in the site of hydroxy-substitution. In general, one may use an N-hydroxyalkyl-substituted glycine to substitute for any polar amino acid, an N-benzyl- or N-aralkyl-substituted glycine to replace any aromatic amino acid (e.g., Phe, Trp, etc.), an N-alkyl-substituted glycine such as N-butylglycine to replace any nonpolar amino acid (e.g., Leu, Val, Ile, etc.), and an N-(aminoalkyl)glycine derivative to replace any basic polar amino acid (e.g., Lys and Arg).

Where an amino acid sequence is provided herein, L-, D-, or beta amino acid versions of the sequence are also contemplated as well as retro, inversion, and retro-inversion isoforms. In addition, conservative substitutions (e.g., in the binding peptide, and/or antimicrobial peptide, and/or linker peptide) are contemplated. Non-protein backbones, such as PEG, alkane, ethylene bridged, ester backbones, and other backbones are also contemplated. Also fragments ranging in length from about 5, 6, 7, 8, 9, 10, 11, 12, 13, 14, 15, 16, 17, 18, 19, 20, 21, 22, 23, 24, or 25 amino acids up to the full length minus one amino acid of the peptide are contemplated where the fragment retains at least 50%, preferably at least 60% 70% or 80%, more preferably at least 90%, 95%, 98%, 99%, or at least 100% of the activity (e.g., binding specificity and/or avidity, antimicrobial activity, etc.) of the full length peptide are contemplated.

A "compound antimicrobial peptide" or "compound AMP" refers to a construct comprising two or more AMPs joined together. The AMPs can be joined directly or through a linker. They can be chemically conjugated or, where joined directly together or through a peptide linker can comprise a fusion protein.

In certain embodiments, conservative substitutions of the amino acids comprising any of the sequences described herein are contemplated. In various embodiments one, two, three, four, or five different residues are substituted. The term "conservative substitution" is used to reflect amino acid substitutions that do not substantially alter the activity (e.g., antimicrobial activity and/or specificity) of the molecule. Typically conservative amino acid substitutions involve substitution one amino acid for another amino acid with similar chemical properties (e.g. charge or hydrophobicity). Certain conservative substitutions include "analog substitutions" where a standard amino acid is replaced by a non-standard (e.g., rare, synthetic, etc) amino acid differing minimally from the parental residue. Amino acid analogs are considered to be derived synthetically from the standard amino acids without sufficient change to the structure of the parent, are isomers, or are metabolite precursors. Examples of such "analog substitutions" include, but are not limited to, 1) Lys-Orn, 2) Leu-Norleucine, 3) Lys-Lys[TFA], 4) Phe-Phe[Gly], and 5) δ-amino butylglycine-ξamino hexylglycine, where Phe[Gly] refers to phenylglycine(a Phe derivative with a H rather than $CH_3$ component in the R group), and Lys[TFA] refers to a Lys where a negatively charged ion (e.g., TFA) is attached to the amine R group. Other conservative substitutions include "functional substitutions" where the general chemistries of the two residues are similar, and can be sufficient to mimic or partially recover the function of the native peptide. Strong functional substitutions include, but are not limited to 1) Gly/Ala, 2) Arg/Lys, 3) Ser/Tyr/Thr, 4) Leu/Ile/Val, 5) Asp/Glu, 6) Gln/Asn, and 7) Phe/Trp/Tyr, while other functional substitutions include, but are not limited to 8) Gly/Ala/Pro, 9) Tyr/His, 10) Arg/Lys/His, 11) Ser/Thr/Cys, 12) Leu/Ile/Val/Met, and 13) Met/Lys (special case under hydrophobic conditions). Various "broad conservative substations" include substitutions where amino acids replace other amino acids from the same biochemical or biophysical grouping. This is similarity at a basic level and stems from efforts to classify the original 20 natural amino acids. Such substitutions include 1) nonpolar side chains: Gly/Ala/Val/Leu/Ile/Met/Pro/Phe/Trp, and/or 2) uncharged polar side chains Ser/Thr/Asn/Gln/Tyr/Cys. In certain embodiments broad-level substitutions can also occur as paired substitutions. For example, Any hydrophilic neutral pair [Ser, Thr, Gln, Asn, Tyr, Cys]+[Ser, Thr, Gln, Asn, Tyr, Cys] can may be replaced by a charge-neutral charged pair [Arg, Lys, His]+[Asp, Glu]. The following six groups each contain amino acids that, in certain embodiments, are typical conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K), Histidine (H); 5) Isoleucine (I), Leucine (L), Methionine (M), Valine (V); and 6) Phenylalanine (F), Tyrosine (Y), Tryptophan (W). Where amino acid sequences are disclosed herein, amino acid sequences comprising, one or more of the above-identified conservative substitutions are also contemplated.

In certain embodiments, targeting peptides, antimicrobial peptides, and/or STAMPs compromising at least 80%, preferably at least 85% or 90%, and more preferably at least 95% or 98% sequence identity with any of the sequences described herein are also contemplated. The terms "identical" or percent "identity," refer to two or more sequences that are the same or have a specified percentage of amino acid residues that are the same, when compared and aligned for maximum correspondence, as measured using one of the following sequence comparison algorithms or by visual inspection. With respect to the peptides of this invention sequence identity is determined over the full length of the peptide. For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. Optimal alignment of sequences for comparison can be conducted, e.g., by the local homology algorithm of Smith & Waterman (1981)*Adv. Appl. Math.* 2: 482, by the homology alignment algorithm of Needleman & Wunsch (1970)*J Mol. Biol.* 48: 443, by the search for similarity method of Pearson & Lipman (1988) *Proc. Natl. Acad. Sci., USA,* 85: 2444, by computerized implementations of these algorithms (GAP, BESTFIT, FASTA, and TFASTA in the Wisconsin Genetics Software Package, Genetics Computer Group, 575 Science Dr., Madison, Wis.), or by visual inspection.

The term "specificity" when used with respect to the antimicrobial activity of a peptide indicates that the peptide preferentially inhibits growth and/or proliferation and/or kills a particular microbial species as compared to other related and/or unrelated microbes. In certain embodiments the preferential inhibition or killing is at least 10% greater (e.g., $LD_{50}$ is 10% lower), preferably at least 20%, 30%, 40%, or 50%, more preferably at least 2-fold, at least 5-fold, or at least 10-fold greater for the target species.

The term "consisting essentially of" when used with respect to an antimicrobial peptide (AMP) or AMP motif as described herein, indicates that the peptide or peptides encompassed by the library or variants, analogues, or derivatives thereof possess substantially the same or greater antimicrobial activity and/or specificity as the referenced peptide. In certain embodiments substantially the same or greater antimicrobial activity indicates at least 80%, preferably at least 90%, and more preferably at least 95% of the antimicrobial activity of the referenced peptide(s) against a particular bacterial species (e.g., *S. mutans*).

The term "STAMP" refers to a Specifically Targeted AntiMicrobial Peptide. In various embodiments, a STAMP comprises one or more peptide targeting moieties attached to one or more antimicrobial moieties (e.g., antimicrobial peptides (AMPs)). The term C16G2 refers to a STAMP whose amino acid sequence consists of the sequence TFFRLFNRSFTQALGKGGGKNLRIIRKGIHIIKKY (SEQ ID NO:1). In various embodiments the carboxyl terminus of the sequence is amidated.

The term "simple antimicrobial peptide" or "AMP" refer to antimicrobial peptides that are not attached to a targeting moiety.

As used herein, the term "about" refers to a measurable value such as an amount, a time duration, and the like, and encompasses variations of ±20%, ±10%, ±5%, ±1%, ±0.5%, or ±0.1% from the specified value.

The term "effective amount" or "therapeutically effective amount" as used herein refers to the amount of a pharmaceutical composition comprising one or more peptides as disclosed herein or a mutant, variant, analog or derivative thereof, to decrease the level of *Streptococcus mutans* and prevent tooth decay, and relates to a sufficient amount of pharmacological composition to provide the desired effect. A therapeutically or prophylactically significant reduction in *S. mutans* is, for example, at least about 10%, at least about 20%, at least about 30%, at least about 40%, at least about 50%, at least about 60%, at least about 70%, at least about 80%, at least about 90%, at least 2 log 10, at least 3 log 10, at least 4 log 10, or at least 5 log 10 or more in CFU/mL as compared to a control or non-treated subject or the state of the subject prior to administering the oligopeptides described herein. Measured or measurable parameters can include clinically detectable markers of disease, for example, within the process of tooth decay. It will be understood, however, that the total daily usage of the compositions and formulations as disclosed herein will be decided by the attending physician or dentist within the scope of sound professional judgment.

BRIEF DESCRIPTION OF THE DRAWINGS

FIG. 2A shows a perspective view of the flat dental strip coated with a delivery layer D containing one or more STAMPs (and/or simple AMPs) and a backing layer (B). FIG. 2B shows a cross-sectional view of a dental strip (e.g., a-a in FIG. 2A) where the delivery layer (D) is disposed in discrete areas (e.g., droplets) on the backing layer (B). FIG. 2C shows a cross-sectional view (e.g., a-a in FIG. 2A) of a dental strip in which the backing layer (B) contains shallow pockets (P) that hold additional volume of the delivery layer (D).

FIG. 3A shows 4 dental strips applied to the rear molars, centered on the occlusal surface (B), but also wraps around the tooth covering both the lingual (A) and buccal surfaces (C), which provides coverage of the molars and bicuspids to treat the biological niche of *S. mutans* with a STAMP. FIG. 3B shows a cross-sectional plan view illustrating the dental strip applied to, and conforming to the surface, of a tooth (C) above the gum tissue (T). In this embodiment the strip is adhesively attached to the teeth by means of the delivery layer (D) which is disposed on backing layer (B).

DETAILED DESCRIPTION

In various embodiments dental strips are provided herein for the delivery of specifically targeted antimicrobial peptides. In certain embodiments the specifically targeted antimicrobial peptides target and kill *S. mutans*, and the dental strips are designed for the delivery of the targeted antimicrobial peptide to a surface of a tooth, to the gums, or to any other surface in the oral cavity.

Accordingly, in various embodiments dental strips are provided that deliver an effective dose of one or more specifically targeted antimicrobial peptide(s) (STAMPs) and/or one or more antimicrobial peptides (AMPs). The STAMPs or AMPs are typically STAMPs or AMPs that kill or inhibit the growth and/or proliferation of bacteria, specifically *Streptococcus mutans* (*S. mutans*). The dental strips are designed to provide a release profile of the STAMP(s) and/or AMPs such that periodic use of the strips reduces the frequency and/or severity of dental caries and/or that inhibits the formation of dental caries. In various embodiments, other agents such as remineralization or other non-peptide antimicrobial compounds can be added to the formulation.

Figure 1:
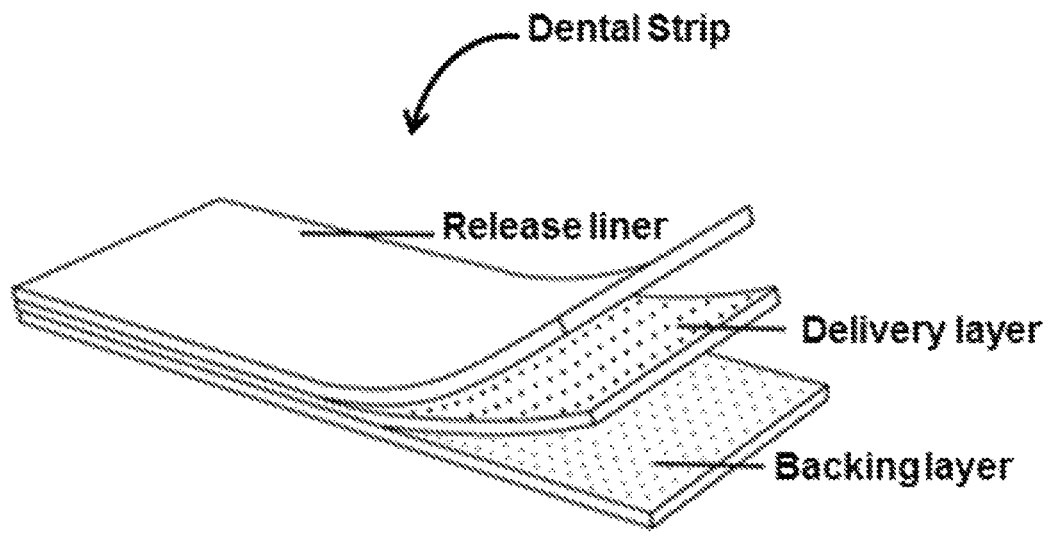
FIG. 1 illustrates one embodiment of a dental strip incorporating a specifically targeted antimicrobial peptide (STAMP) in the delivery layer. In the illustrated embodiments, the dental strip comprises a protective backing layer, an adhesive delivery layer containing the targeted antimicrobial peptide, and an optional release liner.

One illustrative, but non-limiting embodiment, of such a dental strip is shown in FIGS. 1 and 2. As illustrated therein in certain embodiments the dental strip comprises a backing layer (B) with a delivery layer (D) disposed thereon. The delivery layer typically contains one or more specifically targeted antimicrobial peptides as described herein (and/or one or more simple AMPs). In certain embodiments the dental strip can additionally comprise an optimal release liner. In certain embodiments, the delivery layer (e.g., adhesive layer) can contain a plasticizer. Examples of plasticizers useful for incorporation include, but are not limited to, glycols such as propylene glycol, polyethylene glycol (PEG), polyhydric alcohols such as glycerin and sorbitol and glycerol esters such as glycerol triacetate. In certain embodiments the plasticizer comprises an oil (e.g., castor oil).

Figure 2A:
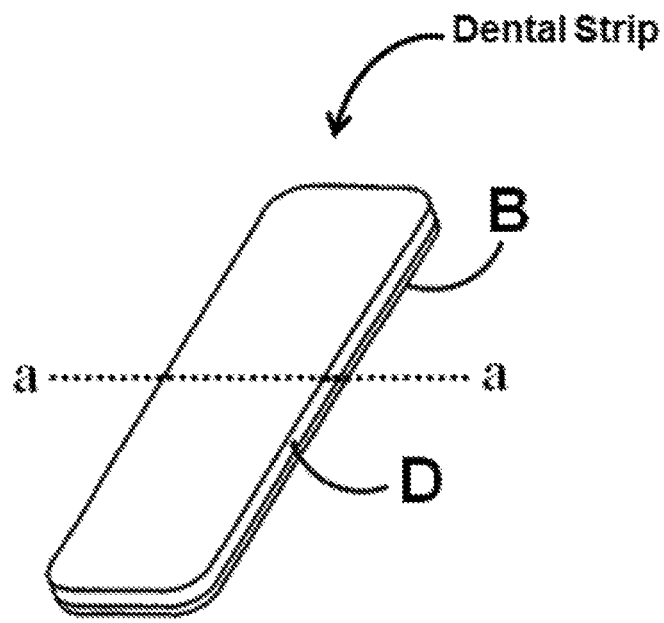
FIGS. 2A-2C, show various illustrative, but non-limiting embodiments of the dental strips described herein.
Figure 2B:
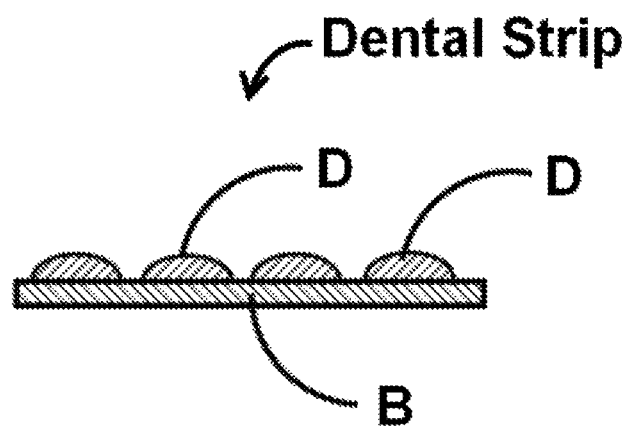

As illustrated in the dental strip shown in FIG. 2A, in certain embodiments the delivery layer (D) is substantially homogeneous, uniformly and continuously coated onto the backing layer (B). However, in certain embodiments, the delivery layer may be a laminate or separated layers of components, an amorphous mixture of components, separate stripes or spots (see, e.g., FIG. 2B), or other patterns of different components, or a combination of these structures including a continuous coating of the delivery layer along a longitudinal axis of a portion of the backing layer B.

Figure 2C:
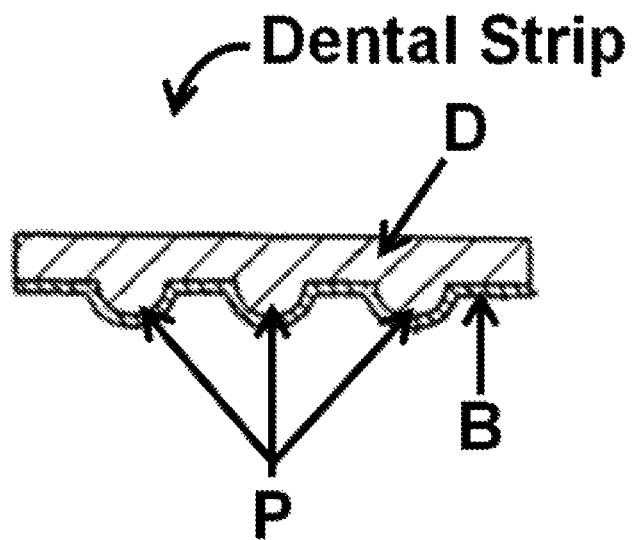

As illustrated in FIG. 2C, in certain embodiments, the backing layer (B) may have shallow pockets (P) formed therein. When the delivery layer (D) is coated on the backing layer, additional delivery layer material fills shallow pockets (P) to provide reservoirs of additional material.

Figure 3A:
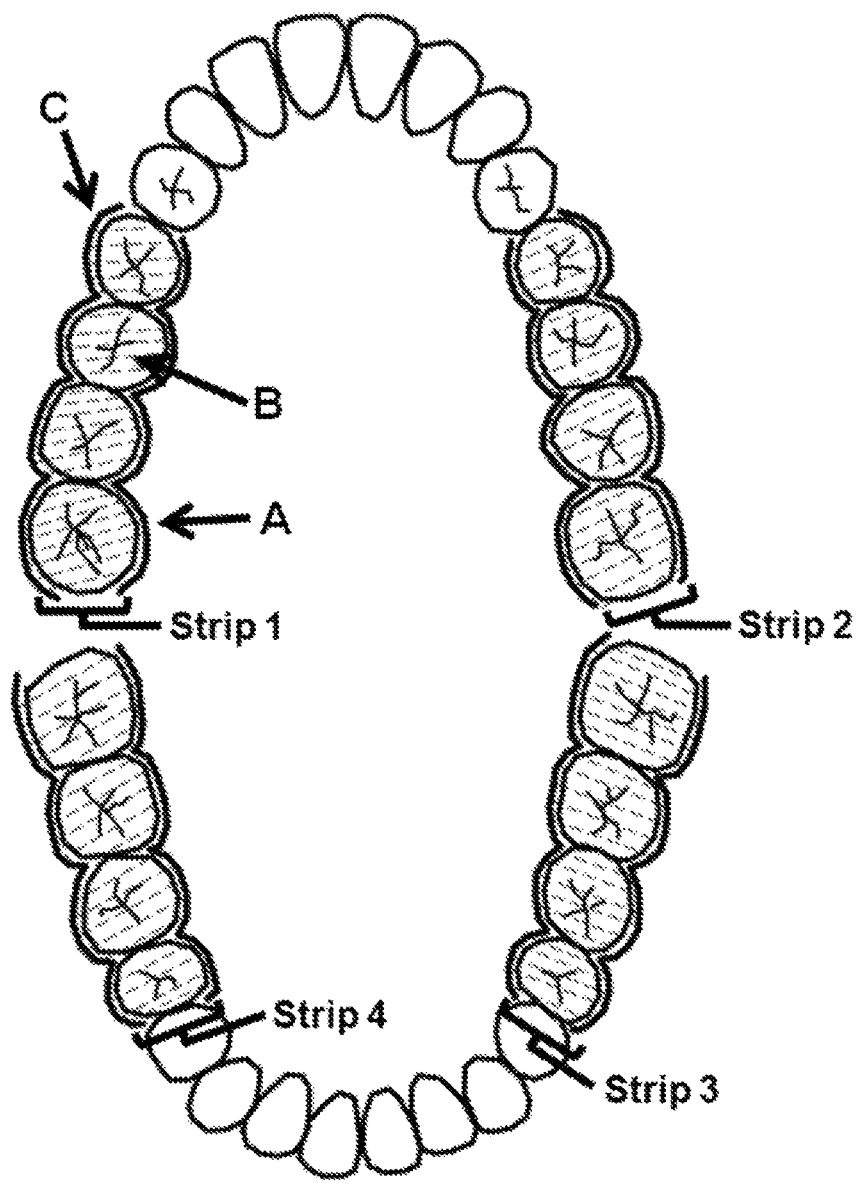
FIGS. 3A and 3B illustrate a dental strip applied to the surface(s) of teeth.
Figure 3B:
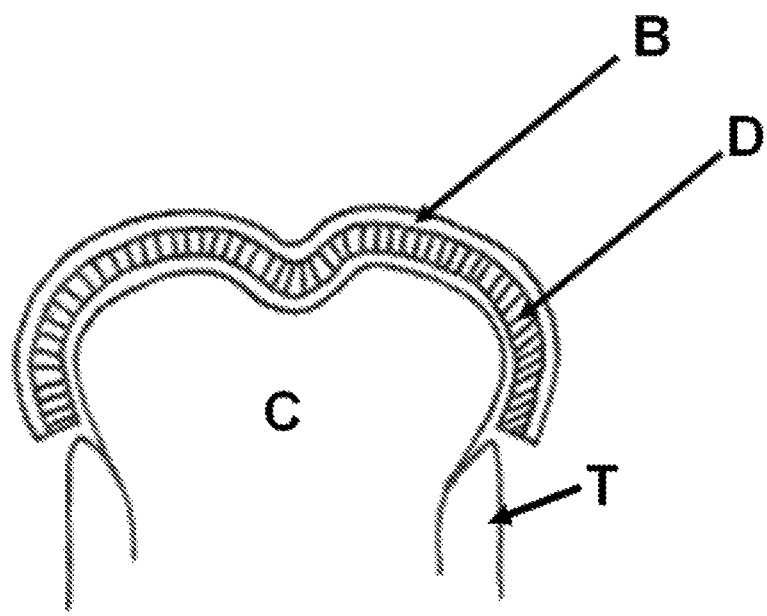
Figure 4:
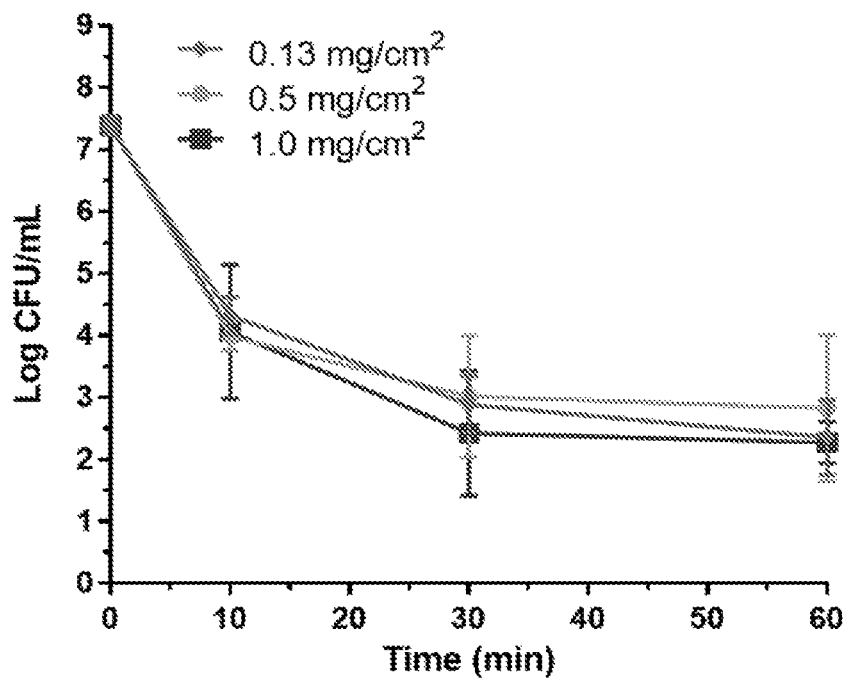
FIG. 4 illustrates the bioactivity of C16G2 in a dental strip formulation as it relates to dose level.
Figure 5:
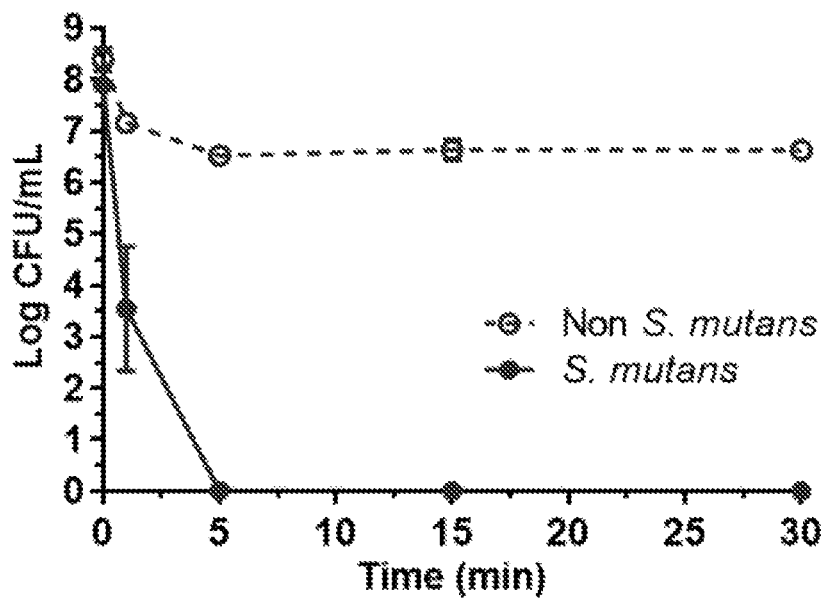
FIG. 5 illustrates the specificity and bioactivity of a C16G2 containing dental strip as described herein.

FIGS. 3A and 3B illustrate the dental strip conformed to the surface of a plurality of adjacent teeth that are embedded in adjacent soft tissue (T). As illustrated, in certain embodiments, the strip is placed on the occlusal surface of the tooth and wraps around the lingual and buccal surfaces of the tooth. Adjacent soft tissue (T) is herein defined as soft tissue surfaces surrounding the tooth structure including, for example, papilla, marginal gingiva, gingival sulculus, inter dental gingiva, gingival gum structure on lingual and buccal surfaces up to and including muco-gingival junction and the pallet.

In FIG. 3B the dental strip comprises a backing layer (B) as described above, and a delivery layer (D) containing the STAMPs and/or simple AMPs facing the surface of the tooth (C). When applied, e.g., as illustrated in FIGS. 3A and 3B, the dental strips are effective to deliver one or more STAMPs (or simple AMPs) to the tooth surface.

In certain embodiments the delivery layer (D) can be pre-applied to the backing (B) layer, or in certain embodiments, may be applied to the backing layer (B) by the user, e.g., just prior to application of the dental strip. In either case, the backing layer (B) typically has a thickness and flexural stiffness that enable it to conform to the contoured surfaces of teeth. Thus, the backing layer typically has sufficient flexibility to form to the contours of the oral surface, in FIGS. 3A and 3B the surface being a plurality of adjacent teeth. In various embodiments the backing layer is also readily conformable to tooth surfaces and to the interstitial tooth spaces without permanent deformation during application.

Backing Layer.

The backing layer (B) typically serves to carry the delivery layer(s) (D) containing the specifically targeted antimicrobial peptides described herein (and/or simple antimicrobial peptides) and facilitates the application of the compositions to the oral surfaces. In certain embodiments the backing layer is one that after application, remains affixed to the teeth during the "treatment time", e.g., (5 minutes up to about 1 hour, or from about 5 minutes to 10 minutes, or from about 10 minutes to 20 minutes, or from about 20 minutes to 30 minutes, for from about 30 minutes to 40 minutes, or from about 40 minutes to 1 hour.) and then is mechanically removed. In certain embodiments the backing layer comprises a material that dissolves over the period of time of the treatment and does not require mechanical removal. In certain embodiments, remaining backing material can simply be removed by tooth brushing, an implement or tool, or an oral rinse.

In certain embodiments the backing layer (B) can serve as a protective barrier for the delivery layer (D). In such instances it can prevent substantial leaching and/or erosion of the delivery layer by for example, the wearer's lips, tongue, as well as saliva. This allows the STAMPs and/or simple AMPs in the delivery layer to act upon the oral surface at a therapeutically relevant concentration for an extended period of time, e.g., from several minutes to several hours. The term "act upon" is herein defined as bringing about a desired change (e.g., the killing and/or inhibition of *S. mutans*).

In certain embodiments the backing layer is removable, i.e., it need not be worn in the oral cavity for the duration of the time that the delivery layer material is present in the oral cavity. Thus, in one such embodiment, the dental strip can be applied to the tooth surface and peeled away leaving the delivery layer remaining affixed to the tooth surface. As used herein, the term "removable" is intended to include manual removal of the backing layer, e.g., by peeling with fingers or a tool, as well as removal of the backing layer as a result of in situ dissolution in the oral cavity, i.e., that occurs without the need for manual peeling.

In certain embodiments the backing layer can be a single layer of material or a laminate of more than one layer. In certain embodiments the backing layer is substantially water impermeable while in other embodiments the backing layer material is water permeable and may be water soluble. In certain embodiments the backing layer is selected to provide a desired dissolution rate in the oral cavity.

In various embodiments, the backing layer typically comprises a non-toxic material. In certain embodiments the backing material is a single material or a combination of materials that meet the required flexural stiffness to facilitate conformation with the tooth surface in an oral cavity and are compatible with the delivery layer material(s). Examples of suitable non-toxic substrates include, but are not limited to, various resins, polymers/elastomers, and paper, and the like. Suitable materials useful as a backing layer include, but are not limited to various polymers such as ethylene oxide polymers, polyethylene, polyvinylacetate, polyesters, and combinations thereof. Other materials suitable for film backing include, but are not limited to cellulose and derivatives thereof derivatives such as ethyl cellulose, propyl cellulose, isopropyl cellulose, butyl cellulose, t-butyl cellulose, cellulose acetate, and polyvinyl alcohol, polyvinyl chloride, polyvinyl acetate and the like.

In some embodiments, the backing layer includes one or more ethylene oxide polymers. In certain embodiments ethylene oxide polymers useful for a backing layer may include homopolymers or mixtures of ethylene oxide polymers of varying molecular weight e.g., of about 10,000 Da to about 10,000,000 Da. In some embodiments ethylene oxide polymers useful for a backing layer include mixtures of ethylene oxide polymers of varying average molecular weight of, e.g., about 100,000 to about 1,500,000 Daltons. Such ethylene oxide polymers are commercially available from various sources. For example, poly(ethylene) oxide polymers having an average molecular weight range of about 10,000 to 1,000,000 Da are available from the Dow Chemical Company under the tradename "POLYOX™."

In certain embodiments the backing layer comprises ethylcellulose. One illustrative suitable ethyl cellulose has a viscosity of 90-110 mPa*s as a 5% solution in 80% toluene, 20% ethanol. In certain embodiments, the weight of the ethylcellulose ranges from about 1 up to 80% of the backing layer, or from about 20% to about 80%, or from about 40% to about 80%, or from about 50 to 70%, or about 62.5%.

In some embodiments, a backing layer further includes one or more plasticizers to alter the stiffness and solubility of the dental strip. Examples of plasticizers useful for incorporation in a film backing include, but are not limited to, glycols such as propylene glycol, polyethylene glycol (PEG), polyhydric alcohols such as glycerin and sorbitol and glycerol esters such as glycerol triacetate. In certain embodiments the plasticizer comprises an oil (e.g., castor oil).

In some embodiments, the plasticizer is present at about 0.1% to about 0.5%, or from about 0.5% to about 1%, or from about 1% to about 3%, for from 3% to about 10%, or from about 10% to 20%, or from about 20% to about 50%, or from about 30% to about 40%, or about 37.5% by weight of the backing layer.

In various embodiments the backing layer can be prepared using conventional extrusion or solvent casting processes. For example, to prepare a film by solvent casting polymer material may be dissolved in a sufficient amount of a solvent that is compatible with the polymer. In some embodiments, examples of suitable solvents include but are not limited to water, alcohols, acetone, ethyl acetate or mixtures thereof.

In embodiments that optionally include a plasticizer, after a solution of the polymer has been formed, a plasticizer can be added with stirring, and heat is applied if necessary to aid dissolution until a clear and homogeneous solution of polymer and plasticizer has been formed. The solution can be coated onto a suitable carrier material and dried to form a film.

In some embodiments, the carrier material has a surface tension that allows the polymer solution to spread evenly across the intended carrier width without soaking in to form a destructive bond between the two substrates. Examples of suitable carrier materials include, but are not limited to glass, stainless steel, teflon, polyethylene-impregnated kraft paper, and the like. In some embodiments, the film is dried.

In certain embodiments the backing layer is generally less than about 1 mm thick, preferably less than about 0.05 mm thick, and more preferably from about 0.001 to about 0.03 mm thick. In certain embodiments the backing layer material is less than about 0.1 mm thick, and/or from about 0.005 mm to about 0.02 mm thick. In some embodiments, the backing layer has a thickness of 20 to 1500 μm, or a thickness of about 30 to 1000 μm.

In certain embodiments the backing layer is substantially water impermeable. In illustrative, but non-limiting embodiments such a backing layer can comprise material(s) such as ethyl cellulose, propyl cellulose, polyethylene, polypropylene, polyolefin, polyurethane, polyethylene terephthalate, polylactic acid, polyacrylates, and ethylene vinyl acetate, combinations thereof, and/or other water impermeable orally compatible polymers.

In certain embodiments the backing layer can be substantially water permeable. In certain embodiments such water permeable materials are soluble in the oral cavity (e.g., they are water or saliva soluble). Illustrative, but non-limiting water permeable materials include but are not limited to hydroxypropylmethylcellulose, hydroxypropylcellulose, and/or hydroxyethylcellulose, starch paper, rice paper, natural gum, pullulan paper, or mixtures thereof. Such embodiments are very convenient for consumer use as they may not require removal after treatment, but simply dissolve during use. They may also provide added safety during overnight use, because there is no chance of accidentally swallowing a backing layer that becomes loose during sleeping.

In various embodiments the shape of the backing layer is any shape and size that covers the desired oral surface(s). The width of the backing layer will also depend upon the oral surface area to be covered. In one example, the width of the strip is from about 0.5 cm to about 4 cm, or from about 1 cm to about 2 cm, or from about 2 cm to 4 cm, or about 3.2 cm. In one example, the length of the strip is from about 1 cm to about 15 cm, or from about 1 cm to about 5 cm, or from about 5 cm to 10 about cm, or from about 10 cm to about 15 cm, or about 4.9 cm, or about 9.8 cm. In certain non-limiting embodiments, the area of the dental strip is about 5 to about 30 $cm^2$, or about 9.7 $cm^2$, or about 19.4 $cm^2$. In certain embodiments the backing layer comprises rounded corners. Rounded corners is defined as not having any sharp angles or points.

In certain embodiments the backing layer can contain shallow pockets. When the delivery layer is coated on a such a backing layer, additional delivery layer material fills shallow pockets to provide reservoirs of additional material.

Additionally, the shallow pockets can help to provide texture to the delivery system. When such pockets are present, the backing layer will typically have an array of shallow pockets. Illustrative the shallow pockets can be approximately 0.4 mm across and 0.1 mm deep. In certain embodiments, when shallow pockets are included in the backing layer and a delivery layer is applied to it in various thicknesses, the overall thickness of the dental strip is generally less than about 1 mm, or less than about 0.5 mm.

Typically the backing layer is selected to provide a desired flexural stiffness to facilitate application of the strip to the tooth surface and retention of the strip thereon. Flexural stiffness is a material property that is a function of a combination of strip thickness, width, and material modulus of elasticity.

In certain embodiments the backing layer has a flexural stiffness (as measured by a Brookfield CT3 Texture Analyzer) of less than about 5 grams/cm. In certain embodiments the backing layer has a flexural stiffness less than about 4 grams/cm, or from about 0.1 grams/cm to about 3 grams/cm, or about 2.77 grams/cm. In certain embodiments the flexural stiffness of the backing layer is substantially constant and does not change during normal use. In certain other embodiments, however, the backing layer dissolves during use and accordingly the flexural stiffness varies (decreases) over time.

In certain embodiments the backing layer material does not need to be hydrated for the strip to achieve the low flexural stiffness in the above-specified ranges. The relatively low stiffness enables the strip of material to cover the contours of the oral surface with very little force being exerted. That is, conformity to the contours of the oral surface of the wearer's mouth is maintained because there is little residual force within the strip of material to cause it to return to its shape just prior to its application to the oral surface, i.e. substantially flat. In various embodiments the backing layer's flexibility enables it to contact soft tissue over an extended period of time without irritation. In various embodiments the backing layer does not require pressure to maintain adhesion of the dental strip to the oral (tooth) surface. In various embodiments the dental strip is held in place on the oral surface by adhesive attachment provided by delivery layer (or by additional adhesion layer materials incorporated into the strip).

In various embodiments the viscosity and general tackiness of the delivery layer(s) cause the dental strip to be adhesively attached to the oral surface without substantial slippage from the frictional forces created by the lips, teeth, tongue and other oral surfaces rubbing against the strip of while talking, drinking, etc. Typically, however, this adhesion to the oral surface is low enough to allow the strip of material to be easily removed by the wearer by simply peeling off the strip of material using ones finger, fingernail or rubbing with a soft implement such as a cotton balls and swabs or gauze pads, or a tooth brush. In certain embodiments the delivery system is easily removable from the oral surfaces without the use of an instrument, a chemical solvent or agent or excessive friction. Such chemical solvents include organic solvent known for use in the oral cavity such as alcohols, and other safe solvents such as water.

In certain embodiments the peel force required to remove the delivery layer with a non-dissolvable backing layer from the oral surface ranges from about 1 gram to about 350 grams for a 17.3 cm$^2$ strip. In certain embodiments the peel force is from about 1 g to about 10 grams, or about 10 g to about 40 grams, or from about 20 grams to about 60 grams, or from about 60 g to about 120 g, or from about 120 g to about 200 g, or from about 200 g to about 350 g, or from about 300 to 320 grams.

The low peel force can be facilitated by the low flexural stiffness of the backing layer. That is a strip of material having high flexural stiffness higher would require an aggressive adhesive to stop the strip of material from pulling it away from the contours of the oral surface it is attached to.

In certain embodiments the backing layer comprises a colorant and/or flavor agent, or the delivery and backing layers comprise a colorant and/or flavor agents.

Delivery Layer.

The dental strips described herein comprise a delivery layer (containing one or more STAMPs and/or simple AMPs) applied to the backing layer. In various embodiments the delivery layer when contacted, e.g., to a tooth surface, additionally acts as an adhesive layer to attach the dental strip to the tooth surface. The delivery layer is typically applied to one surface of the backing layer/film. In some embodiments, the delivery layer is coated onto the film backing. In some embodiments the delivery layer is hydratable. In various embodiments the delivery layer includes a water-swellable polymer or combination of polymers, and one or more STAMPs (and/or simple AMPs).

In certain embodiments the delivery layer may exhibit tackiness, or an adhesive quality, prior to coming in contact with water or saliva. In other embodiments, the delivery layer exhibits increased tackiness or adhesive quality upon coming in contact with water or saliva. In certain embodiments the delivery layer includes suitable additives such as flavorants, colorants, and/or preservatives.

In various embodiments the delivery layer is fabricated from one or more materials that maintain the stability and activity of the active agents (e.g., STAMPs and/or simple AMPs) contained therein and that provide release kinetics that maintain a concentration of active agent for a duration of time sufficient to provide the desired therapeutic and/or prophylactic effect (e.g., to kill or inhibit S. mutans in the oral cavity).

The delivery layer containing the STAMPs (or simple AMPs) can be in a variety of forms. In certain embodiments the delivery layer is or forms a gel, particularly an aqueous gel. A typical gel is a high viscosity matrix formed from gelling agents known in the art. Preferred gelling agents are safe for oral use. In certain embodiments the gelling agents do not readily dissolve in saliva, and do not react with or inactivate the STAMPs (or AMPs) oral care compounds incorporated into (or deposited on) them.

Generally, the gelling agent is a swellable polymer. Furthermore, the gel formed with these agents provide sufficient adhesive attachment of the film material to the targeted area of the mouth. In certain embodiments the level of gelling agent to form the delivery layer gel composition is from about 0.1% to about 15%, or from about 1% to about 10%, or preferably from about 2% to about 8%, or from about 4% to about 6%, by weight of the delivery layer material. Suitable gelling agents include, but are not limited to carboxypolymethylene, carboxymethyl cellulose, carboxypropyl cellulose, poloxamers, carrageenan, Veegum, carboxyvinyl polymers, and natural gums such as gum karaya, xanthan gum, Guar gum, gum arabic, gum tragacanth, and mixtures thereof. One illustrative gelling agent for use in the dental strips is carboxypolymethylene (obtainable from B. F. Goodrich Company under the tradename CARBOPOL®). Illustrative carbopols include Carbopol 934, 940, 941, 956 and mixtures thereof.

In certain embodiments the delivery layer comprises a polyvinylpyrrolidone, and in certain embodiments is a polyvinylpyrrolidone with a molecular weight of about 50,000 to about 300,000.

While a polyvinylpyrrolidone delivery layer typically provides sufficient adhesiveness to a tooth surface, in certain embodiments, additional gelling agents may also be included in the formula to help delivery layer adhere to the tissues of the oral cavity. Suitable agents include both polymers with limited water solubility as well as polymers lacking water solubility. These polymers deposit a thin film on both the oral cavity's soft and hard tissues when saliva combines with the instant composition. Suitable limited water solubility adhesives include: hydroxy ethyl or propyl cellulose. Adhesives lacking water solubility include: ethyl cellulose. Still another possible material suitable for use in the instant composition is a combination of GANTREZ™ copolymer and the semisynthetic, water-soluble polymer carboxymethyl cellulose. It is noted that GANTREZ™ AN copolymers contain alternating units of methylvinylether and maleic anhydride. The fundamental character of this polymerization provides that a maleic anhydride unit is adjacent to a methylvinylether unit and vice versa, resulting in a true alternating copolymer.

If the delivery layer comprises an aqueous gel, the water present in the gel compositions should preferably be deionized and free of organic impurities. In certain embodiments water comprises from about 0.1% to 95%, or from about 0.5% to about 90%, or from about 1% to about 5%, or about 1% by weight of delivery layer. This amount of water includes the free water that is added plus that amount that is introduced with other materials.

In certain embodiments a pH adjusting agent may also be added to optimize the storage stability of the delivery layer and STAMPs or AMPs disposed therein or thereon and to make the substance safe for oral tissue. These pH adjusting agents, or buffers, can be any material that is suitable to adjust the pH of the oral delivery layer. Suitable materials include, but are not limited to sodium bicarbonate, sodium phosphate, sodium hydroxide, ammonium hydroxide, ethanolamine, triethanolamine, citric acid, hydrochloric acid, sodium citrate, and combinations thereof. In certain embodiments the pH adjusting agents are added in sufficient amounts so as to adjust the pH of the delivery layer to about 4.5 to about 11, or from about 5.5 to about 8.5, or from about 6 to about 7. In certain embodiments pH adjusting agents are present in an amount of from about 0.01% to about 15%, or from about 0.05% to about 5%, by weight of the delivery layer material.

In certain embodiments an additional carrier material may also be added to the delivery layer. In certain embodiments carrier materials can be humectants. Suitable humectants include, but are not limited to glycerin, sorbitol, polyethylene glycol, propylene glycol, and other edible polyhydric alcohols. When present, humectants typically range in amount of from about 1% or from about 5%, or from about 10% up to about 80% or up to about 50% by weight of the delivery layer material. In addition to the above materials, a number of other components can also be added to the delivery layer. Additional components include, but are not limited to, flavoring agents, sweetening agents, xylitol, opacifiers, coloring agents, and chelants such as ethylenediaminetetraacettic acid.

In certain embodiments the delivery layer is distributed on the backing film as a plurality of dots or regions or as a substantially continuous layer. In various embodiments the delivery layer (e.g., dots or layer) range in thickness from about 20 μm to about 500 μm. In certain embodiments the delivery layer contains the specifically targeted antimicrobial peptide at an amount ranging from about 0.1 mg/cm$^2$ up to about 20 mg/cm$^2$ of dental strip. In certain embodiments the dental strip contains a total amount of specifically targeted antimicrobial peptide ranging from about 1 mg/strip, or from about 2 mg/strip, or from about 4 mg/strip or from about 8 mg/strip up to about 50 mg/strip, or up to about 40 mg/strip, or up to about 30 mg/strip, or up to about 20 mg/strip., and/or comprises about 9.2 mg/strip or about 18.4 mg/strip., or about 36.8 mg/strip, or about 73.6 mg/strip, or about 147.2 mg/strip, or about 193.8 mg/strip, or about 387.6 mg/strip. In various embodiments the dental strip, when applied to a tooth surface delivers sufficient specifically targeted antimicrobial peptide to kill or to inhibit the growth and/or proliferation of S. mutans on the tooth surface and/or adjacent gums.

In various embodiments the delivery layer is provided on the strip in a substantially dry form. However, in certain embodiments, the orally compatible polymer comprising the adhesive is hydratable and/or dissolvable in the mouth. In certain embodiments the orally compatible polymer dissolves over a period of time ranging from about 1 minute or from about 2 minutes or from about 5 minutes, or from about 10 minutes up to about 3 hours, or up to about 2 hours, or up to about 1 hour, or up to about 45 minutes, or up to about 30 minutes, or up to about 20 minutes In certain embodiments the orally compatible polymer comprising the adhesive comprises a material selected from the group consisting of a polyvinylpyrrolidone, (hydroxypropyl) methylcellulose, polyvinyl alcohol, hydroxyethyl/hydroxypropyl cellulose, and methacrylate/acrylate copolymers and/or their esters.

In certain embodiments the delivery layer further comprises a colorant and/or a flavor agent.

In some embodiments, a delivery layer further includes one or more plasticizers to alter the stiffness and solubility of the dental strip. Examples of plasticizers useful for incorporation in a delivery or adhesive film include, but are not limited to, glycols such as propylene glycol, polyethylene glycol (PEG), polyhydric alcohols such as glycerin and sorbitol and glycerol esters such as glycerol triacetate. In certain embodiments the plasticizer comprises an oil (e.g., castor oil).

In some embodiments, the plasticizer is present at about 0.1% or from about 0.5%, or from about 1%, or from about 3% up to about 30%, or up to about 20%, or up to about 15%, or up to about 10% by weight of the delivery or adhesive layer, or about 18% by weight of the delivery layer.

The amount of delivery layer material containing STAMP(s) and/or simple AMPs applied to the dental strip or oral surface depends upon the size and capacity of the dental strip, concentration of the active agent(s) (e.g., STAMP(s) and/or AMPs), the duration of application. In certain embodiments generally less than about 1 gram of active agent is applied to the tooth surface, or from about 1 mg, or from about 5 mg up to about 500 mg, or from about 50 mg to 100 mg, or from about 75 mg to 150 mg, or from about 100 mg to 200 mg, or from about 125 mg to 250 mg, or from about 200 to 500 mg.

In certain embodiments the amount of STAMP and/or simple AMP amount of oral care substance per square cm of material is less than about 5 grams/cm$^2$, or from about 0.00001 to about 0.08 grams/cm$^2$, or about 0.0002 g/cm$^2$ to about 0.010 g/cm$^2$, or from 0.0009 g/cm$^2$ to about 0.003 g/cm$^2$.

In certain embodiments the dental strip comprises about 90 mg to 100 mg polyvinylpyrrolidone; and about 5 mg to about 80 mg specifically targeted antimicrobial peptide (e.g., C16G2 or other STAMP described herein). In certain embodiments, the dental strip comprises about 5 mg to about 10 mg, or about 10 mg to about 20 mg, or about 20 mg to about 30 mg, or about 30 mg to about 40 mg, or from about 40 mg to about 50 mg, or from about 50 mg to about 60 mg, or from about 60 mg to about 70 mg, or from about 70 mg to about 80 mg targeted antimicrobial peptide. In certain embodiments the dental strip comprises about 3 mg to about 4 mg sucralose. In certain embodiments the dental strip comprises about 25 mg to about 30 mg flavoring agent.

It will be recognized that while in certain embodiments the dental strips described herein comprise a C16G2 STAMP, in various embodiments any of the other STAMPs described herein can be utilized as well as combinations of any of the STAMPs described herein. Additionally in certain embodiments, any of the simple antimicrobial peptides described herein can be used alone or in combination with STAMPs in the dental strips described herein.

In certain embodiments the dental strip is fabricated by combining the STAMP with the orally compatible polymer and depositing the polymer on the backing layer (e.g., by printing, dripping, spraying, and the like). The layer is dried and then, in certain embodiments, a release film is added on top of the adhesive. The strips can then be cut to size as desired.

Certain illustrative, but non-limiting embodiments of dental strips are shown in Tables 5-7 in Example 1. The various embodiments and formulations of dental strips are illustrative and non-limiting. Using the teaching provided herein numerous other STAMP-releasing dental strips will be available to one of skill in the art.

Additional Agents.

In certain embodiments the dental strips can additionally include one or more active agents other than STAMPs and/or AMPs. In certain embodiments the active agents comprise a positively charged compound that is antimicrobial and/or that promotes remineralization. In certain embodiments the dental strips additionally include a fluoride. In certain embodiments the fluoride comprises an agent selected from the group consisting of sodium fluoride, stannous fluoride, sodium monofluorophosphate, zinc hexafluorosilicate, sodium hexafluorosilicate, ammonium fluoride, calcium fluoro-phosphate ($Ca_5[F(PO_4)_3]$) or fluorapatite, fluorine-doped hydroxyapatite (e.g., $Ca_5(PO_4)_3(OH,F)$, calcium fluoride ($CaF_2$) or fluorite or fluorspar, $TiF_4$, and acidulated fluoride.

In certain embodiments the additional active agents can comprise one or more remineralization agents. Illustrative remineralization agents include, but are not limited to, hydroxyapatite, fluorapatite, Tri-Calcium Phosphate (TCP), $CaKPO_4$, $Ca_2NaK(PO_4)_2$, casein phosphopeptide/amorphous calcium phosphate, bioactive glass, ACP (calcium sulfate and dipotassium phosphate), xylitol, and a polyphenol (e.g., proanthocyanidin (PA).

Tri-Calcium phosphate (TCP) is a hybrid material created with a milling technique that fuses beta tricalcium phosphate and sodium lauryl sulfate or fumaric acid. This blending results in a "functionalized" calcium and a "free" phosphate, designed to increase the efficacy of fluoride remineralization. TCP provides catalytic amounts of calcium to boost fluoride efficacy and can coexist with fluoride in a dental varnish as contemplated herein.

In casein phosphopeptide/amorphous calcium phosphate remineralization agents, casein phosphopeptides (CPPs) are typically produced from the tryptic digest of casein, aggregated with calcium phosphate and purified through ultrafiltration. Casein has the ability to stabilize calcium and phosphate ions by releasing small sequences of casein phosphopeptides (CPPs) through partial enzymic digestion that led to the development of a remineralization technology based on casein phosphopeptide-stabilized amorphous calcium phosphate complexes (CPP-ACP) and casein phosphopeptide-stabilized amorphous calcium fluoride phosphate complexes (CPP-ACFP).

The ACP technology utilizes a two-phase delivery system to keep the calcium and phosphorous components from reacting with each other before use. Accordingly, the two phases of the ACP technology can be incorporated into the two components comprising the dental strip systems described herein. Current sources of calcium and phosphorous are two salts, calcium sulfate and dipotassium phosphate. When the two salts are mixed, they rapidly form ACP that can precipitate on to the tooth surface. This precipitated ACP can then readily dissolve into the saliva and can be available for tooth remineralization.

Bioactive glass (BIOGLASS®) acts as a biomimetic mineralizer matching the body's own mineralizing traits while also affecting cell signals in a way that benefits the restoration of tissue structure and function. Bioglass® in an aqueous environment immediately begins surface reaction in three phases, leaching and exchange of cations, network dissolution of $SiO_2$ and precipitation of calcium and phosphate to form an apatite layer. The critical stages for glass surface reactions, the initial $Na^+$ and $H^+/H_3O^+$ ion exchange and de-alkalinization of the glass surface layer are quite rapid, within minutes of implantation and exposure to body fluids. The net negative charge on the surface and loss of sodium causes localized breakdown of the silica network with the resultant formation of silanol (SiOH) groups, which then repolymerize into a silica-rich surface layer. Within 3-6 h in vitro, the calcium phosphate layer will crystallize into the carbonated hydroxyapatite (CAP) layer, which is essentially the bonding layer. Chemically and structurally, this apatite is nearly identical to bone and tooth mineral. Bioactive glass formulations commonly used contain 45 wt % $SiO_2$ 4.5 wt % $Na_2O$ and CaO and 6 wt % $P_2O_5$. NOVAMIN®, a trade name for bioactive glass, is manufactured by Novamin Technologies Inc. (Alachua, Fla., USA). It has been demonstrated that fine particulate bioactive glasses (<90 µm) incorporated into an aqueous dentifrice have the ability to clinically reduce the tooth hypersensitivity through the occlusion of dentinal tubules by the formation of the CAP layer.

In certain embodiments, peptides or proteins comprising repeats of the tripeptides DSS or ESS can be incorporated in the delivery layer. Proteins and peptides containing DSS-like repeats are involved in the rebuilding of tooth structure, such as remineralization of enamel and rebuilding of dentin. Synthetic peptides comprising DSS or ESS repeats are contemplated, as well as proteins that contain these sequence repeats, such as dentin sialophosphoprotein and dentin phosphoprotein. In certain embodiments the peptide includes a single DSS or ESS. In certain embodiments the peptide comprises 2, 3, 4, 5, 6, 7, 8, 9, 10, 11, or 12 repeats of DSS or ESS. In certain embodiments the repeats are contiguous.

In certain embodiments, a combination of arginine and insoluble calcium compounds can be present in the delivery layer. Arginine-calcium carbonate compounds have been shown to occlude exposed dentinal tubules and reduce dental sensitivity, and may contribute to enamel remineralization. In certain embodiments, the amount of arginine-calcium carbonate is from about 1 to 10%, or about 8% by weight.

Xylitol is a non-cariogenic five-carbon sugar alcohol that occurs naturally in plants and is used as a substitute for sugar. Xylitol has the ability to reduce dental plaque formation, make plaque less adhesive, neutralize plaque acids by decreasing the production of lactic acid, reduce the levels of *S. mutans*, reduce cavities by up to 80%, demonstrate significant long-term reduction in caries (88-93%), assist in the remineralization of tooth enamel, reduce gum tissue inflammation, and help with dry mouth and bad breath.

In certain embodiments, antibacterial or antiseptic agents such as bleach, or antiseptic agents with general positive charge can be incorporated into the delivery layer. These agents include but are not limited to chlorhexidine, cetylpyridimium chloride, positively charged antimicrobial nanoparticles, and polyhexamethylene biguanide (PHMB). The cationic character of these agents allows for rapid release from the delivery layer during use.

It has been suggested that the preservation and stability of dentin collagen may be essential during the remineralization process, because it acts as a scaffold for mineral deposition. It has also been suggested that the presence of an organic matrix may reduce the progression of erosion in dentin. One of the important strategies regarding preventive therapies for root caries is to promote remineralization of demineralized dentin.

Polyphenols are plant-derived substances that have antioxidant and anti-inflammatory properties. They are believed to interact with microbial membrane proteins, enzymes and lipids, thereby altering cell permeability and permitting the loss of proteins, ions and macromolecules. One such polyphenol is proanthocyanidin (PA), which is a bioflavanoidcontaining benzene-pyran-phenolic acid molecular nucleus. The PA accelerates the conversion of soluble collagen to insoluble collagen during development and increases collagen synthesis to potentially aid in the remineralization of demineralized dentin.

The foregoing remineralization agents are illustrative and non-limiting. Numerous other remineralization agents are known and can readily be incorporated into the strip systems described herein.

In various embodiments the remineralization agent(s) may be present in the delivery layer(s) of the dental strip in amounts of from about 1 weight percent to about 20 weight percent, or up to about 15 weight percent, or up to about 10 weight percent, or up to about 5 weight percent, such as from about 2 weight percent up to about 5 weight percent (e.g., after combination of the first component with the second component). In certain embodiments the remineralization agent(s) comprise about 2 weight percent of the dental strip (e.g., after combination of the first component with the second component). In certain embodiments CPP-ACT is present in the dental strip at about 1 weight percent up to about 2 weight percent. In certain embodiments TCP is present at about 5 weight percent or less. In certain embodiments xylitol (when used as a remineralization is present at about 1 weight percent or about 2 weight percent or about 5 weight percent up to about 30 weight percent. In certain embodiments xylitol is present at about 20 weight percent.

The fluoride or remineralization agent can be mixed into the delivery layer. In certain embodiments the fluoride and/or remineralization agent is provided in a separate delivery layer. In certain embodiments the separate layer comprises a substantially continuous lamina that can be deposited above or below the delivery layer. In certain embodiments the separate layer comprises disposition in domains on the backing layer that are separate from the domains containing the STAMP(s) and/or AMPs.

The Release Liner

In various embodiments the dental strip is provided with a release liner disposed on the delivery layer. The release liner can typically be formed from any material that exhibits less affinity for (adhesion to) the delivery layer than the delivery layer material exhibits for itself and for the backing layer so that the release liner can be removed from the strip without disrupting the delivery layer(s).

In certain embodiments the release liner preferably comprises a sheet of material such as polyethylene, paper, polyester, or other material that, in certain embodiments, can be coated with a non-stick type of material to facilitate release from the dental strip when desired. Thus, for example, in certain embodiments, the release liner material may be coated with wax, silicone, teflon, fluoropolymers, or other non-stick type materials. One illustrative but non-limiting release liner is a polyethylene terephthalate and polytetrafluoroethylene film (e.g., SCOTCHPAK®, produced by 3M). In another illustrative but non-limiting release liner is a polyester and an ethylene vinyl acetate copolymer. In certain embodiments the release liner is cut to substantially the same size and shape as the underlying dental strip or the release liner can be cut to a size that is larger than the dental strip to provide a readily accessible means for separating the material from the strip.

In certain embodiments the release liner can be formed from a brittle material that cracks when the strip is flexed or from multiple pieces of material or a scored piece of material. In certain embodiments the release liner can be in two (or more) overlapping pieces such as a typical adhesive strip bandage design. Various release liners are well known to those of skill in the art (see, e.g., Kirk-Othmer Encyclopedia of Chemical Technology, Fourth Edition, Volume 21, pp. 207-218; and the like).

In certain embodiments the release liner ranges in thickness from about 50 to about 200 µm.

Specifically Targeted Antimicrobial Peptide (or AMP) in or on the Delivery Layer.

The delivery layer preferably contains, or has disposed thereon, one or more STAMPs and/or simple AMPs active at a level where upon directed use, they promotes the benefit sought by the wearer (e.g., inhibition of *S. mutans*, decrease in caries formation, etc.) without detriment to the oral surface it is applied to.

In certain embodiments the specifically targeted antimicrobial peptide(s) incorporated into the dental strips described herein comprise a targeting peptide that binds *Streptococcus mutans*. In various embodiments the targeting peptide is attached to an antimicrobial via chemical conjugation. In other embodiments, the targeting peptide is attached directly to an antimicrobial or an amino acid, or through a peptide linker to form a single polypeptide comprising at least one targeting domain and at least one antimicrobial domain.

In certain embodiments the targeting peptides bind (e.g., specifically bind) is the C16G2 STAMP whose amino acid sequence consists of the sequence TFFRLFNRSFTQAL-GKGGGKNLRIIRKGIHIIKKY (SEQ ID NO:2). This STAMP comprises a fragment of the competence stimulating peptide (CSP) having the amino acid sequence TFFRLFNRSFTQALGK (SEQ ID NO:3) as a targeting peptide attached to the antimicrobial peptide KNLRIIRKGI-HIIKKY (SEQ ID NO:4) by a 3 Gly linker. In various embodiments the peptide is amidated at the carboxyl terminus.

The STAMPs contemplated for use in the formulations described herein are not limited to C16G2. Any of a number of targeting peptides can be attached to any of a number of antimicrobial peptides, e.g., as described below.

It will be noted that in various embodiments the targeting peptide comprises a peptide that ranges in length from 5 amino acid, or from 6 amino acids, or from 7 amino acids, or from 8 amino acids up to about 50 amino acids, or up to about 40 amino acids, or up to about 30 amino acids, or up to about 20 amino acids. Similarly, in various embodiments, the antimicrobial peptide comprises a peptide that ranges in length from 5 amino acids, or from 6 amino acids, or from 7 amino acids, or from 8 amino acids, or from 9 amino acids, or from 10 amino acids up to about 100 amino acids, or up to about 80 amino acids, or up to about 60 amino acids, or up to about 50 amino acids, or up to about 40 amino acids, or up to about 30 amino acids, or up to about 20 amino acids.

Targeting Peptides that Bind *S. mutans*.

A number of peptides can be used as targeting peptides in the targeted antimicrobial peptides contemplated herein. In certain embodiments the targeting peptide is one that binds, inter alia to *S. mutans*. In certain embodiments the targeting peptide specifically binds to *S. mutans*.

Illustrative peptides that bind *S. mutans* include, but are not limited to a peptide that comprises or consists of an amino acid sequence selected from the group consisting of SGSLSTFFRLFNRSFTQALGK (CSP, SEQ ID NO:5) or a fragment thereof, EMRLSKFFRDFILQRKK (CSP1, (SEQ ID NO:6) or a fragment thereof, and EMRISRIILD-FLFLRKK (CSP2, (SEQ ID NO:7), NIFEYFLE (SEQ ID NO:8). or a fragment thereof.

In certain embodiments the targeting peptide comprises or consists of an the amino acid sequence of competence stimulating peptide (CSP) or a fragment thereof. Illustrative CSP fragments that bind *S. mutans* are shown in Table 1.

TABLE 1

Illustrative CSP fragments.

| Amino Acid Sequence | SEQ ID NO |
|---|---|
| TFFRLFNR | 9 |
| TFFRLFNRS | 10 |
| TFFRLFNRS | 11 |
| TFFRLFNRSF | 12 |
| TFFRLFNRSFT | 13 |
| TFFRLFNRSFTQ | 14 |
| TFFRLFNRSFTQA | 15 |
| TFFRLFNRSFTQAL | 16 |
| TFFRLFNRSFTQALG | 17 |
| TFFRLFNRSFTQALGK | 18 |
| STFFRLFNR | 19 |
| STFFRLFNRS | 20 |
| STFFRLFNRS | 21 |
| STFFRLFNRSF | 22 |
| STFFRLFNRSFT | 23 |
| STFFRLFNRSFTQ | 24 |
| STFFRLFNRSFTQA | 25 |
| STFFRLFNRSFTQAL | 26 |
| STFFRLFNRSFTQALG | 27 |
| STFFRLFNRSFTQALGK | 28 |
| LSTFFRLFNR | 29 |
| LSTFFRLFNRS | 30 |
| LSTFFRLFNRS | 31 |
| LSTFFRLFNRSF | 32 |
| LSTFFRLFNRSFT | 33 |
| LSTFFRLFNRSFTQ | 34 |
| LSTFFRLFNRSFTQA | 35 |
| LSTFFRLFNRSFTQAL | 36 |
| LSTFFRLFNRSFTQALG | 37 |
| LSTFFRLFNRSFTQALGK | 38 |
| SLSTFFRLFNR | 39 |
| SLSTFFRLFNRS | 40 |
| SLSTFFRLFNRS | 41 |
| SLSTFFRLFNRSF | 42 |
| SLSTFFRLFNRSFT | 43 |
| SLSTFFRLFNRSFTQ | 44 |

TABLE 1-continued

Illustrative CSP fragments.

| Amino Acid Sequence | SEQ ID NO |
|---|---|
| SLSTFFRLFNRSFTQA | 45 |
| SLSTFFRLFNRSFTQAL | 46 |
| SLSTFFRLFNRSFTQALG | 47 |
| SLSTFFRLFNRSFTQALGK | 48 |
| GSLSTFFRLFNR | 49 |
| GSLSTFFRLFNRS | 50 |
| GSLSTFFRLFNRS | 51 |
| GSLSTFFRLFNRSF | 52 |
| GSLSTFFRLFNRSFT | 53 |
| GSLSTFFRLFNRSFTQ | 54 |
| GSLSTFFRLFNRSFTQA | 55 |
| GSLSTFFRLFNRSFTQAL | 56 |
| GSLSTFFRLFNRSFTQALG | 57 |
| GSLSTFFRLFNRSFTQALGK | 58 |
| SGSLSTFFRLFNR | 59 |
| SGSLSTFFRLFNRS | 60 |
| SGSLSTFFRLFNRS | 61 |
| SGSLSTFFRLFNRSF | 62 |
| SGSLSTFFRLFNRSFT | 63 |
| SGSLSTFFRLFNRSFTQ | 64 |
| SGSLSTFFRLFNRSFTQA | 65 |
| SGSLSTFFRLFNRSFTQAL | 66 |
| SGSLSTFFRLFNRSFTQALG | 67 |

Other suitable targeting peptides that bind *S. mutans* include, but are not limited to peptides that comprise or consist of the amino acid sequence $$X^1-X^2-F-R-X^5-X^6-X^7-R-X^9-X^{10}-X^{11}-X^{12}-X^{13}-X^{14}-X^{15}-X^{16}$$ (SEQ ID NO:68)

or the inverse of said amino acid sequence, wherein $X^1$ is a polar amino acid, or A; $X^2$ is F, W, Q, A, or an analog thereof; $X^5$ is a hydrophobic amino acid; $X^6$ is a hydrophobic amino acid, N, Q, or an analog thereof; $X^7$ is a polar amino acid, A, F, or an analog thereof; $X^9$ is a polar amino acid, A or an analog thereof; $X^{10}$ is a hydrophobic amino acid, Q, A, or an analog thereof; $X^{11}$ is a hydrophobic amino acid; $X^{12}$ is Q, A, or an analog thereof; $X^{13}$ is a non-polar amino acid; X14 is a hydrophobic amino acid; X15 is a non-polar amino acid, N, S, D, or an analog thereof; X16 is a polar amino acid, F, A, or an analog thereof; and said peptide ranges in length up to 100 amino acids. The peptide does not comprise or consist of the amino acid sequence of C16 (TFFRLFNRSFTQALGK (SEQ ID NO:69).

In certain embodiments, $X^1$ is a polar amino acid or A, and in certain embodiments A or T; and/or $X^2$ is F, W, Q, A, and in certain embodiments F; and/or $X^5$ is a hydrophobic amino acid in certain embodiments L or A; and in certain embodiments L; and/or $X^6$ is a hydrophobic amino acid, N or Q, in certain embodiments F, L, N, A, or Q; in certain embodiments hydrophobic; and in certain embodiments F; and/or $X^7$ is a polar amino acid, A, or F; in certain embodiments a polar amino acid or A; in certain embodiments N, A, S, D, or F; in certain embodiments N or A, and in certain embodiments N; and/or $X^9$ is a polar amino acid or A, in certain embodiments S or A, and in certain embodiments preferably S; and/or $X^{10}$ is a hydrophobic amino acid, Q, or A, in certain embodiments a hydrophobic amino acid, in certain embodiments F or L, and in certain embodiments F; $X^{11}$ is a hydrophobic amino acid, in certain embodiments T or A, and in certain embodiments T; and/or $X^{12}$ is a Q or A, and in certain embodiments Q; and/or $X^{13}$ is a non-polar amino acid, in certain embodiments P or A, and in certain embodiments preferably A; and/or $X^{14}$ is a hydrophobic amino acid, in certain embodiments L or A, and in certain embodiments L; and/or $X^{15}$ is a non-polar amino acid, N, S, or D, in certain embodiments G, A, F, N, S, or D, and in certain embodiments G or A; and/or $X^{16}$ is a polar amino acid, F, or A, in certain embodiments a polar amino acid, in certain embodiments K or Q, and in certain embodiments K.

In certain embodiments the targeting peptide comprises or consists of one or more of the amino acid sequences shown in Table 2.

TABLE 2

*S. mutans* targeting peptides. Anti-biofilm activity level (% viability remaining for *S. mutans*) is shown.

| Name | Amino Acid Sequence | SEQ ID NO | % viability remaining |
|---|---|---|---|
| C16AG2 (N7, L14) | AFFRAFNRAFAQALAK | 70 | 16 |
| C16AG2 (T1) | TFFRAFARAFAQAAAK | 71 | 18 |
| C16AG2 (L14) | AFFRAFARAFAQALAK | 72 | 20 |
| C16AG2 (L5) | AFFRLFARAFAQAAAK | 73 | 21 |
| F2F6F10-L2L6L10_C16G2 | TLFRLLNRSLTQALGK | 74 | 26 |
| G15-F15_C16G2 | TFFRLFNRSFTQALFK | 75 | 29 |
| F10-L10_C16G2 | TFFRLFNRSLTQALGK | 76 | 30 |
| G15-N15_C16G2 | TFFRLFNRSFTQALNK | 77 | 30 |
| C16AG2 | AFFRAFARAFAQAAAK | 78 | 30 |
| C16AG2 (N7) | AFFRAFNRAFAQAAAK | 79 | 34 |
| G15-S15_C16G2 | TFFRLFNRSFTQALSK | 80 | 37 |
| C16AG2 (S9) | AFFRAFARSFAQAAAK | 81 | 38 |
| C16AG2 (G15) | AFFRAFARAFAQAAGK | 82 | 38 |
| C16AG2 (T11) | AFFRAFARAFTQAAAK | 83 | 39 |
| K16-Q16_C16G2 | TFFRLFNRSFTQALGQ | 84 | 42 |
| F6-L6_C16G2 | TFFRLLNRSFTQALGK | 85 | 43 |
| F2-W2_C16G2 | TWFRLFNRSFTQALGK | 86 | 45 |
| C16AG2 (F14) | AFFRAFARAFAQAFAK | 87 | 46 |
| F2 to Q2_C16G2 | TQFRLFNRSFTQALGK | 88 | 47 |
| G15-D15_C16G2 | TFFRLFNRSFTQALDK | 89 | 47 |
| G15-A15_C16G2 | TFFRLFNRSFTQALAK | 90 | 47 |
| K16-E16_C16G2 | TFFRLFNRSFTQALGE | 91 | 48 |
| N7-S7_C16G2 | TFFRLFSRSFTQALGK | 92 | 50 |
| K16-A16_C16G2 | TFFRLFNRSFTQALGA | 93 | 51 |
| N7-D7_C16G2 | TFFRLFDRSFTQALGK | 94 | 52 |
| K16-F16_C16G2 | TFFRLFNRSFTQALGF | 95 | 53 |
| C16AG2 (T1, S9, T11) | TFFRAFARSFTQAAAK | 96 | 56 |
| C16AG2 (T1, L5, S9, T11, G15) | TFFRLFARSFTQAAGK | 97 | 57 |

TABLE 2-continued

S. mutans targeting peptides. Anti-biofilm activity level (% viability remaining for S. mutans) is shown.

| Name | Amino Acid Sequence | SEQ ID NO | % viability remaining |
|---|---|---|---|
| ΔA13_ΔG15_C16G2 | TFFRLFNRSFTQ L K | 98 | 57 |
| K16-S16_C16G2 | TFFRLFNRSFTQALGS | 99 | 59 |
| F2-L2_C16G2 | TLFRLFNRSFTQALGK | 100 | 63 |
| N7-F6 / N21-I24 | TFFRLNFRSFTQALGK | 101 | 65 |
| F10 to Q10_C16G2 | TFFRLFNRSQTQALGK | 102 | 73 |
| Scan-16 | TFFRLFAAAFTQALGK | 103 | 73 |
| Scan-24 | TFFRLFNRSFTQALGK** | 104 | 75 |
| Scan-17 | TFFRLFNRSAAAALGK | 105 | 76 |
| N7-F10 / N21-I32 | TFFRLFFRSNTQALGK*** | 106 | 76 |
| Scan-22 | TFFRLFNRSFTQPLGK | 107 | 77 |
| F2/6/10-A2/6/10_C16G2 | TAFRLANRSATQALGK | 108 | 78 |
| Scan-18 | TFFRLFNRSFTQAAAA | 109 | 78 |
| F6 to Q6_C16G2 | TFFRLQNRSFTQALGK | 110 | 79 |
| Scan-23 | TFFRLFNRSFTQALPK | 111 | 79 |
| TFF-TYY_C16G2 | TYYRLFNRSFTQALGK | 112 | 80 |
| ΔN7_C16G2 | TFFRLF RSFTQALGK | 113 | 84 |
| F7/11/15 sub Q_C16G2 | TQFRLQNRSQTQALGK | 114 | 93 |

Antimicrobial Peptides.

In certain embodiments, the targeting peptides described herein (e.g., peptides shown in Table 1 and Table 2) can be attached to one or more antimicrobial peptides to form selectively targeted antimicrobial peptides (STAMPs) that are disposed onto or incorporated into the delivery layer(s) compromising the dental strips described herein. In certain embodiments the antimicrobial peptides (e.g., the AMPs described herein) are used as simple AMPs without attachment of targeting moieties. Numerous antimicrobial peptides are well known to those of skill in the art.

In certain embodiments the antimicrobial peptides comprise one or more amino acid sequences described for example below in Table 3). In certain embodiments the antimicrobial peptides comprise one or more amino acid sequences described in the "Collection of Anti-Microbial Peptides" (CAMP) an online database developed for advancement the understanding of antimicrobial peptides (see, e.g., Thomas et al. (2009) Nucleic Acids Res., 1-7.doi: 10.1093/nar/gkp1021) available at www.bicnirrh.res.in/antimicrobial.

TABLE 3

Novel antimicrobial peptides, target microorganisms and MIC values.

| ID | Organism/MIC | Sequence | SEQ ID NO |
|---|---|---|---|
| G2 | | KNLRIIRKGIHIIKKY* | 115 |
| Novispirin G10 | | KNLRRIIRKGIHIIKKYG | 116 |
| Novispirin T10 | | KNLRRIIRKTIHIIKKYG | 117 |
| Novispirin G7 | | KNLRRIGRKIIHIIKKYG | 118 |
| Novispirin T7 | | KNLRRITRKIIHIIKKYG | 119 |
| Ovispirin | | KNLRRIIRKIIHIIKKYG | 120 |

TABLE 3-continued

Novel antimicrobial peptides, target microorganisms and MIC values.

| ID | Organism/MIC | Sequence | SEQ ID NO |
|---|---|---|---|
| PGG | | GLLRRLRKKIGEIFKKYG | 121 |
| Protegrin-1 | | RGGRLCYCRRRFCVCVGR* | 122 |
| K-1 | S. mutans, 25 µM | GLGRVIGRLIKQIIWRR | 123 |
| K-2 | S. mutans, 12.5 µM | VYRKRKSILKIYAKLKGWH | 124 |
| K-7 | S. mutans, 12.5 µM | NYRLVNAIFSKIFKKKFIKF | 125 |
| K-8 | S. mutans, 4 µM | KILKFLFKKVF | 126 |
| K-9 | S. mutans, 4 µM | FIRKFLKKWLL | 127 |
| K-10 | S. mutans, 4 µM | KLFKFLRKHLL | 128 |
| K-11 | S. mutans, 4 µM | KILKFLFKQVF | 129 |
| K-12 | S. mutans, 8 µM | KILKKLFKFVF | 130 |
| K-13 | S. mutans, 16 µM | GILKKLFTKVF | 131 |
| K-14 | S. mutans, 8 µM | LRKFLHKLF | 132 |
| K-15 | S. mutans, 4 µM | LRKNLRWLF | 133 |
| K-16 | S. mutans, 8 µM<br>P. aeruginosa, 12.5 µM<br>MRSA, 25 µM | FIRKFLQKLHL | 134 |
| K-17 | S. mutans, 8 µM | FTRKFLKFLHL | 135 |
| K-18 | S. mutans, 16 µM | KKFKKFKVLKIL | 136 |
| K-19 | S. mutans, 16 µM | LLKLLKLKKLKF | 137 |
| K-20 | S. mutans, 8 µM | FLKFLKKFFKKLKY | 138 |
| K-21 | S. mutans, 8 µM | GWLKMFKKIIGKFGKF | 139 |
| K-22 | S. mutans, 8 µM | GIFKKFVKILYKVQKL | 140 |
| 1T-88 | | GRLVLEITADEVKALGEALAN<br>AKI | 141 |
| PF-531 | A. baumannii, 25 µM<br>P. aeruginosa, 50 µM<br>T. rubrum, 50 µM<br>A. niger, 25 µM<br>B. subtilis, 25 µM<br>C. difficile, 12.5 µM<br>C. jeikeium, 6.25 µM<br>S. epidermidis, 50 µM<br>S. mutans, 12.5 µM | YIQFHLNQQPRPKVKKIKIFL | 142 |
| PF-527 | P. aeruginosa, 50 µM<br>T. rubrum, 25 µM<br>A. niger, 50 µM<br>B. subtilis, 12.5 µM<br>C. jeikeium, 6.25 µM<br>MRSA, 50 µM<br>S. epidermidis, 25 µM | GSVIKKRRKRMAKKKHRKLL<br>KKTRIQRRRAGK | 143 |
| PF-672 | C. albicans, 1.56 µM<br>T. rubrum, 0.78 µM<br>A. niger, 3 µM<br>B. subtilis, 0.78 µM<br>E. faecalis, 3.13 µM<br>MRSA, 1.56 µM<br>S. epidermidis, 0.39 µM | MRFGSLALVAYDSAIKHSWPR<br>PSSVRRLRM | 144 |

TABLE 3-continued

Novel antimicrobial peptides, target microorganisms and MIC values.

| ID | Organism/MIC | Sequence | SEQ ID NO |
|---|---|---|---|
| PF-606 | E. coli, 50 µM<br>MRSA, 50 µM<br>S. epidermidis, 50 µM<br>S. mutans, 50 µM<br>S. pneumoniae, 50 µM | FESKILNASKELDKEKKVNTALSFNSHQDFAKAYQNGKI | 145 |
| PF-547 | T. rubrum, 25 µM<br>B. subtilis, 25 µM<br>S. mutans, 12.5 µM | WSRVPGHSDTGWKVWHRW | 146 |
| PF-006 | A. baumannii, 50 µM<br>B. subtilis, 25 µM<br>MRSA, 50 µM | MGIIAGIIKFIKGLIEKFTGK | 147 |
| PF-545 | A. niger, 50 µM<br>B. subtilis, 25 µM<br>MRSA, 50 µM | RESKLIAMADMIRRRI | 148 |
| PF-278 | C. albicans, 50 µM<br>T. rubrum, 50 µM<br>S. epidermidis, 50 µM | LSLATFAKIFMTRSNWSLKRFNRL | 149 |
| PF-283 | T. rubrum, 50 µM<br>B. subtilis, 50 µM<br>S. epidermidis, 50 µM | MIRIRSPTKKKLNRNSISDWKSNTSGRFFY | 150 |
| PF-307 | C. albicans, 50 µM<br>T. rubrum, 50 µM<br>B. subtilis, 50 µM | MKRRRCNWCGKLFYLEEKSKEAYCCKECRKKAKKVKK | 151 |
| PF-168 | T. rubrum, 50 µM<br>A. niger, 50 µM<br>MRSA, 50 µM | VLPFPAIPLSRRRACVAAPRPRSRQRAS | 152 |
| PF-538 | A. baumannii, 25 µM<br>C. difficile, 25 µM | KNKKQTDILEKVKEILDKKKKTKSVGQKLY | 153 |
| PF-448 | A. niger, 25 µM<br>S. pneumoniae, 50 µM | SLQSQLGPCLHDQRH | 154 |
| PF-583 | MRSA, 50 µM<br>S. epidermidis, 50 µM | KFQGEFTNIGQSYIVSASHMSTSLNTGK | 155 |
| PF-600 | E. coli, 50 µM<br>S. pneumoniae, 50 µM | TKKIELKRFVDAFVKKSYENYILERELKKLIKAINEELPTK | 156 |
| PF-525 | A. niger, 50 µM<br>S. pneumoniae, 50 µM | KFSDQIDKGQDALKDKLGDL | 157 |
| PF-529 | A. niger, 50 µM<br>S. pneumoniae, 50 µM | LSEMERRRLRKRA | 158 |
| PF-148 | A. niger, 50 µM<br>B. subtilis, 50 µM | RRGCTERLRRMARRNAWDLYAEHFY | 159 |
| PF-530 | A. baumannii, 25 µM | SKFKVLRKIIIKEYKGELMLSIQKQR | 160 |
| PF-522 | C. difficile, 25 µM | FELVDWLETNLGKILKSKSA | 161 |
| PF-497 | B. subtilis, 50 µM | LVLRICTDLFTFIKWTIKQRKS | 162 |
| PF-499 | B. subtilis, 50 µM | VYSFLYVLVIVRKLLSMKKRIERL | 163 |
| PF-322 | B. subtilis, 50 µM | GIVLIGLKLIPLLANVLR | 164 |
| PF-511 | S. pneumoniae, 50 µM | VMQSLYVKPPLILVTKLAQQN | 165 |
| PF-512 | S. pneumoniae, 50 µM | SFMPEIQKNTIPTQMK | 166 |
| PF-520 | S. pneumoniae, 50 µM | LGLTAGVAYAAQPTNQPTNQPTNQPTNQPTNQPRW | 167 |

TABLE 3-continued

Novel antimicrobial peptides, target microorganisms and MIC values.

| ID | Organism/MIC | Sequence | SEQ ID NO |
|---|---|---|---|
| PF-521 | S. pneumoniae, 50 μM | CGKLLEQKNFFLKTR | 168 |
| PF-523 | S. pneumoniae, 50 μM | ASKQASKQASKQASKQASKQASRSLKNHLL | 169 |
| PF-524 | S. pneumoniae, 50 μM | PDAPRTCYHKPILAALSRIVVTDR | 170 |
| PF-209 | MRSA, 50 μM | NYAVVSHT | 171 |
| PF-437 | S. pneumoniae, 50 μM | FQKPFTGEEVEDFQDDDEIPTII | 172 |
| CAM135 | | GWRLIKKILRVFKGL | 173 |
| B-33 | | FKKFWKWFRRF | 174 |
| B-34 | | LKRFLKWFKRF | 175 |
| B-35 | | KLFKRWKHLFR | 176 |
| B-36 | | RLLKRFKHLFK | 177 |
| B-37 | | FKTFLKWLHRF | 178 |
| B-38 | | IKQLLHFFQRF | 179 |
| B-39 | | KLLQTFKQIFR | 180 |
| B-40 | | RILKELKNLFK | 181 |
| B-41 | | LKQFVHFIHRF | 182 |
| B-42 | | VKTLLHIFQRF | 183 |
| B-43 | | KLVEQLKEIFR | 184 |
| B-44 | | RVLQEIKQILK | 185 |
| B-45 | | VKNLAELVHRF | 186 |
| B-46 | | ATHLLHALQRF | 187 |
| B-47 | | KLAENVKEILR | 188 |
| B-48 | | RALHEAKEALK | 189 |
| B-49 | | FHYFWHWFHRF | 190 |
| B-50 | | LYHFLHWFQRF | 191 |
| B-51 | | YLFQTWQHLFR | 192 |
| B-52 | | YLLTEFQHLFK | 193 |
| B-53 | | FKTFLQWLHRF | 194 |
| B-54 | | IKTLLHFFQRF | 195 |
| B-55 | | KLLQTFNQIFR | 196 |
| B-56 | | TILQSLKNIFK | 197 |
| B-57 | | LKQFVKFIHRF | 198 |
| B-58 | | VKQLLKIFNRF | 199 |
| B-59 | | KLVQQLKNIFR | 200 |
| B-60 | | RVLNQVKQILK | 201 |
| B-61 | | VKKLAKLVRRF | 202 |
| B-62 | | AKRLLKVLKRF | 203 |
| B-63 | | KLAQKVKRVLR | 204 |

TABLE 3-continued

Novel antimicrobial peptides, target microorganisms and MIC values.

| ID | Organism/MIC | Sequence | SEQ ID NO |
|---|---|---|---|
| B-64 | | RALKRIKHVLK | 205 |
| 1C-1 | | RRRRWWW | 206 |
| 1C-2 | | RRWWRRW | 207 |
| 1C-3 | | RRRWWWR | 208 |
| 1C-4 | | RWRWRWR | 209 |
| 2C-1 | | RRRFWWR | 210 |
| 2C-2 | | RRWWRRF* | 211 |
| 2C-3 | | RRRWWWF* | 212 |
| 2C-4 | | RWRWRWF* | 213 |
| 3C-1 | | RRRRWWK | 214 |
| 3C-2 | | RRWWRRK | 215 |
| 3C-3 | | RRRWWWK | 216 |
| 3C-4 | | RWRWRWK | 217 |
| 4C-1 | | RRRKWWK | 218 |
| 4C-2 | | RRWKRRK | 219 |
| 4C-3 | | RRRKWWK | 220 |
| 4C-4 | | RWRKRWK | 221 |
| a-3 | | LHLLHQLLHLLHQF* | 222 |
| a-4 | | AQAAHQAAHAAHQF* | 223 |
| a-5 | | KLKKLLKKLKKLLK | 224 |
| a-6 | | LKLLKKLLKLLKKF* | 225 |
| a-7 | | LQLLKQLLKLLKQF* | 226 |
| a-8 | | AQAAKQAAKAAKQF* | 227 |
| a-9 | | RWRRWWRHFHHFFH* | 228 |
| a-10 | | KLKKLLKRWRRWWR | 229 |
| a-11 | | RWRRLLKKLHHLLH* | 230 |
| a-12 | | KLKKLLKHLHHLLH* | 231 |
| BD-1 | | FVFRHKWVWKHRFLF | 232 |
| BD-2 | | VFIHRHVWVHKHVLF | 233 |
| BD-3 | | WRWRARWRWRLRWRF | 234 |
| BD-4 | | WRIHLRARLHVKFRF | 235 |
| BD-5 | | LRIHARFKVHIRLKF | 236 |
| BD-6 | | FHIKFRVHLKVRFHF | 237 |
| BD-7 | | FHVKIHFRLHVKFHF | 238 |
| BD-8 | | LHIHAHFHVHIHLHF | 239 |
| BD-9 | | FKIHFRLKVHIRFKF | 240 |
| BD-10 | | FKAHIRFKLRVKFHF | 241 |

TABLE 3-continued

Novel antimicrobial peptides, target microorganisms and MIC values.

| ID | Organism/MIC | Sequence | SEQ ID NO |
|---|---|---|---|
| BD-11 | | LKAKIKFKVKLKIKF | 242 |
| BD-12 | | WIWKHKFLHRHFLF | 243 |
| BD-13 | | VFLHRVIKHKLVF | 244 |
| BD-14 | | FLHKHVLRHRIVF | 245 |
| BD-15 | | VFKHKIVHRHILF | 246 |
| BD-16 | | FLFKHLFLHRIFF | 247 |
| BD-17 | | LFKHILIHRVIF | 248 |
| BD-18 | | FLHKHLFKHKLF | 249 |
| BD-19 | | VFRHRFIHRHVF | 250 |
| BD-20 | | FIEIKLVHKHVLF | 251 |
| BD-21 | | VLRHLFRHRIVF | 252 |
| BD-22 | | LVHKLILRHLLF | 253 |
| BD-23 | | VFKRVLIHKLIF | 254 |
| BD-24 | | IVRKFLFRHKVF | 255 |
| BD-25 | | VLKHVIAHKRLF | 256 |
| BD-26 | | FIRKFLFKHLF | 257 |
| BD-27 | | VIRHVWVRKLF | 258 |
| BD-28 | | FLFRHRFRHRLVF | 259 |
| BD-29 | | LFLHKHAKHKFLF | 260 |
| BD-30 | | FKHKFKHKFIF | 261 |
| BD-31 | | LRHRLRHRLIF | 262 |
| BD-32 | | LILKFLFKFVF | 263 |
| BD-33 | | VLIRILVRVIF | 264 |
| BD-34 | | FRHRFRHRF | 265 |
| BD-35 | | LKHKLKHKF | 266 |
| BD-36 | | FKFKHKLIF | 267 |
| BD-37 | | LRLRHRVLF | 268 |
| BD-38 | | FKFLFKFLF | 269 |
| BD-39 | | LRLFLRWLF | 270 |
| BD-40 | | FKFLFKHKF | 271 |
| BD-41 | | LRLFLRHRF | 272 |
| BD-42 | | FKFLFKF | 273 |
| BD-43 | | LRLFLRF | 274 |
| AA-1 | | HHFFHHFHHFFHHF* | 275 |
| AA-2 | | FHFFHHFFHFFHHF* | 276 |
| AA-3 | | KLLKGATFHFFHHFFHFFHHF | 277 |
| AA-4 | | KLLKFHFFHHFFHFFHHF | 278 |
| AA-5 | | FHFFHHFFHFFHHFKLLK | 279 |

TABLE 3-continued

Novel antimicrobial peptides, target microorganisms and MIC values.

| ID | Organism/MIC | Sequence | SEQ ID NO |
|---|---|---|---|
| RIP | | YSPWTNF* | 280 |
| LL-37 | | LLGDFFRKSKEKIGKEFKRIVQRIKDFLRNLVPRTES | 281 |
| Cys-LL-37 | | CLLGDFFRKSKEKIGKEFKRIVQRIKDFLRNLVPRTES | 282 |
| LL-37(17-32) | | FKRIVQRIKDFLRNLV | 283 |
| Cys-LL-37-Cys | | CLLGDFFRKSKEKIGKEFKRIVQRIKDFLRNLVPRTESC | 284 |
| LL-37FK-13 | | FKRIVQRIKDFLR | 285 |
| LL-37FKR | | FKRIVQRIKDFLRNLVPRTES | 286 |
| LL-37GKE | | GKEFKRIVQRIKDFLRNLVPR | 287 |
| LL-37KRI | | KRIVQRIKDFLRNLVPRTES | 288 |
| LL-37LLG | | LLGDFFRKSKEKIGKEFKRIV | 289 |
| LL-37RKS | | RKSKEKIGKEFKRIVQRIKDFLRNLVPRTES | 290 |
| LL-37SKE | | SKEKIGKEFKRIVQRIKDFLR | 291 |
| LL-37-Cys | | LLGDFFRKSKEKIGKEFKRIVQRIKDFLRNLVPRTESC | 292 |
| BD2.21 | | KLFKFLRKHLL | 293 |
| AF5 | | FLKFLKKFFKKLK | 294 |
| | | FIGAIARLLSKIFGKR | 295 |
| | | GIFSKLAGKKIKNLLISG | 296 |
| | | GIFSKLAGKKIKNLLISGLKG | 297 |
| | | GLFSKFVGKGIKNFLIKGVK | 298 |
| | | KAYSTPRCKGLFRALMCWL | 299 |
| | | KIFGAIWPLALGALKNLIK | 300 |
| | | GWGSFFKKAAHVGKHVGKAALTHYL | 301 |
| | | RGLRRLGRKIAHGVKKYG | 302 |
| | | RGLRRLGRKIAHGVKKYGPTVLRIIRIAG | 303 |
| | | KIAHGVKKYGPTVLRIIR | 304 |
| | | LLGDFFRKSKEKIGKEFKRIVQRIKDFLRNLVPRTES | 305 |
| | | FLPLIGRVLSGIL | 306 |
| | | IGKFLKKAKKFGKAFVKILKK | 307 |
| | | GKFLKKAKKFGKAFVKIL | 308 |
| | | WFLKFLKKFFKKLKY | 309 |
| | | RGLRRLGRKIAHGVKKY | 310 |
| | | LLGDFFRKSKEKI | 311 |

TABLE 3-continued

Novel antimicrobial peptides, target microorganisms and MIC values.

| ID | Organism/MIC | Sequence | SEQ ID NO |
|---|---|---|---|
| | | ILRWPWWPWRRK | 312 |
| | | KLFGALWPLALGALKNLLK | 313 |

A number of antimicrobial peptides are also disclosed in U.S. Pat. Nos. 7,271,239, 7,223,840, 7,176,276, 6,809,181, 6,699,689, 6,420,116, 6,358,921, 6,316,594, 6,235,973, 6,183,992, 6,143,498, 6,042,848, 6,040,291, 5,936,063, 5,830,993, 5,428,016, 5,424,396, 5,032,574, 4,623,733, which are incorporated herein by reference for the disclosure of particular antimicrobial peptides.

In certain embodiments the antimicrobial peptides comprise one or more amino acid sequences described in the "Collection of Anti-Microbial Peptides" (CAMP) an online database developed for advancement the understanding of antimicrobial peptides (see, e.g., Thomas et al. (2009) *Nucleic Acids Res.*, 2009, 1-7. doi:10.1093/nar/gkp1021) available at www.bicnirrh.res.in/antimicrobial.

In certain embodiments, the antimicrobial peptide is a novaspririn, a novaspirin fragment or analog, e.g., as shown above in Table 3. In certain embodiments constructs are contemplated where one or more of the targeting peptides described herein are attached (e.g., directly or through a linker) to a modulated version of novispirin G10 designated G2 (KNLRIIRKGIHIIKKY (SEQ ID NO:314). In this case, the C terminal amino acids can be removed and an internal arginine can be eliminated to facilitate chemical synthesis. Novispirin G10 (the "parent molecule") is an antimicrobial alpha-helical octadecapeptide structurally related to cathelicidins and other innate immunity peptides.

Joining Targeting Peptides to Antimicrobial Peptides.
Chemical Conjugation.

In certain embodiments the targeting peptides are attached directly to the antimicrobial peptides antimicrobial peptides via naturally occurring reactive groups or the targeting peptide(s) and/or the antimicrobial peptides can be functionalized to provide such reactive groups.

In various embodiments the targeting peptides are attached to the antimicrobial peptides via one or more linking agents. Thus, in various embodiments the targeting peptides and the antimicrobial peptides can be conjugated via a single linking agent or multiple linking agents. For example, the targeting peptide and the antimicrobial peptide can be conjugated via a single multifunctional (e.g., bi-, tri-, or tetra-) linking agent or a pair of complementary linking agents. In another embodiment, the targeting peptide and the antimicrobial peptides are conjugated via two, three, or more linking agents. Suitable linking agents include, but are not limited to, e.g., functional groups, affinity agents, stabilizing groups, and combinations thereof.

In certain embodiments the linking agent is or comprises a functional group. Functional groups include monofunctional linkers comprising a reactive group as well as multifunctional crosslinkers comprising two or more reactive groups capable of forming a bond with two or more different functional targets (e.g., labels, proteins, macromolecules, semiconductor nanocrystals, or substrate). In some preferred embodiments, the multifunctional crosslinkers are heterobifunctional crosslinkers comprising two or more different reactive groups.

Suitable reactive groups include, but are not limited to thiol (—SH), carboxylate (COOH), carboxyl (—COOH), carbonyl, amine (NH$_2$), hydroxyl (—OH), aldehyde (—CHO), alcohol (ROH), ketone (R$_2$CO), active hydrogen, ester, sulfhydryl (SH), phosphate (—PO$_3$), or photoreactive moieties. Amine reactive groups include, but are not limited to e.g., isothiocyanates, isocyanates, acyl azides, NHS esters, sulfonyl chlorides, aldehydes and glyoxals, epoxides and oxiranes, carbonates, arylating agents, imidoesters, carbodiimides, and anhydrides. Thiol-reactive groups include, but are not limited to e.g., haloacetyl and alkyl halide derivates, maleimides, aziridines, acryloyl derivatives, arylating agents, and thiol-disulfides exchange reagents. Carboxylate reactive groups include, but are not limited to e.g., diazoalkanes and diazoacetyl compounds, such as carbonyldiimidazoles and carbodiimides. Hydroxyl reactive groups include, but are not limited to e.g., epoxides and oxiranes, carbonyldiimidazole, oxidation with periodate, N,N'-disuccinimidyl carbonate or N-hydroxylsuccimidyl chloroformate, enzymatic oxidation, alkyl halogens, and isocyanates. Aldehyde and ketone reactive groups include, but are not limited to e.g., hydrazine derivatives for schiff base formation or reduction amination. Active hydrogen reactive groups include, but are not limited to e.g., diazonium derivatives for mannich condensation and iodination reactions. Photoreactive groups include, but are not limited to e.g., aryl azides and halogenated aryl azides, benzophenones, diazo compounds, and diazirine derivatives.

Other suitable reactive groups and classes of reactions useful in forming chimeric moieties (targeted antimicrobial peptides) include those that are well known in the art of bioconjugate chemistry. Currently favored classes of reactions available with reactive chelates are those which proceed under relatively mild conditions. These include, but are not limited to, nucleophilic substitutions (e.g., reactions of amines and alcohols with acyl halides, active esters), electrophilic substitutions (e.g., enamine reactions), and additions to carbon-carbon and carbon-heteroatom multiple bonds (e.g., Michael reaction, Diels-Alder addition). These and other useful reactions are discussed in, for example, March (1985) *Advanced Organic Chemistry*, 3rd Ed., John Wiley & Sons, New York, Hermanson (1996) *Bioconjugate Techniques*, Academic Press, San Diego; and Feeney et al. (1982) *Modification of Proteins; Advances in Chemistry Series*, Vol. 198, American Chemical Society, Washington, D.C..

A "linker" or "linking agent" as used herein, is a molecule that is used to join two or more molecules. In certain embodiments the linker is typically capable of forming covalent bonds to both molecule(s) (e.g., the targeting peptide and the antimicrobial peptide). Suitable linkers are well known to those of skill in the art and include, but are not limited to, straight or branched-chain carbon linkers, heterocyclic carbon linkers, or peptide linkers. In certain embodiments the linkers can be joined to the constituent amino acids through their side groups (e.g., through a disulfide linkage to cysteine). However, in certain embodiments, the linkers will be joined to the alpha carbon amino and carboxyl groups of the terminal amino acids.

A bifunctional linker having one functional group reactive with a group on one molecule (e.g., a targeting peptide), and another group reactive on the other molecule (e.g., an antimicrobial peptide), can be used to form the desired conjugate. Alternatively, derivatization can be performed to provide functional groups. Thus, for example, procedures for the generation of free sulfhydryl groups on peptides are also known (See U.S. Pat. No. 4,659,839).

In certain embodiments the linking agent is a heterobifunctional crosslinker comprising two or more different reactive groups that form a heterocyclic ring that can interact with a peptide. For example, a heterobifunctional crosslinker such as cysteine may comprise an amine reactive group and a thiol-reactive group can interact with an aldehyde on a derivatized peptide. Additional combinations of reactive groups suitable for heterobifunctional crosslinkers include, for example, amine- and sulfhydryl reactive groups; carbonyl and sulfhydryl reactive groups; amine and photoreactive groups; sulfhydryl and photoreactive groups; carbonyl and photoreactive groups; carboxylate and photoreactive groups; and arginine and photoreactive groups. In one embodiment, the heterobifunctional crosslinker is SMCC.

Many procedures and linker molecules for attachment of various molecules to peptides or proteins are known (see, e.g., European Patent Application No. 188,256; U.S. Pat. Nos. 4,671,958, 4,659,839, 4,414,148, 4,699,784; 4,680,338; 4,569,789; and 4,589,071; and Borlinghaus et al. (1987) Cancer Res. 47: 4071-4075).

Fusion Proteins.

In certain embodiments the targeted antimicrobial peptide can be chemically synthesized or expressed as a recombinant fusion protein (i.e., a chimeric fusion protein).

In certain embodiments the chimeric fusion proteins are synthesized using recombinant DNA methodology. Generally this involves creating a DNA sequence that encodes the fusion protein, placing the DNA in an expression cassette under the control of a particular promoter, expressing the protein in a host, isolating the expressed protein and, if required, renaturing the protein.

DNA encoding the fusion proteins can be prepared by any suitable method, including, for example, cloning and restriction of appropriate sequences or direct chemical synthesis by methods such as the phosphotriester method of Narang et al. (1979)*Meth. Enzymol.* 68: 90-99; the phosphodiester method of Brown et al. (1979) *Meth. Enzymol.* 68: 109-151; the diethylphosphoramidite method of Beaucage et al. (1981) *Tetra. Lett.,* 22: 1859-1862; and the solid support method of U.S. Pat. No. 4,458,066.

Chemical synthesis produces a single stranded oligonucleotide. This can be converted into double stranded DNA by hybridization with a complementary sequence or by polymerization with a DNA polymerase using the single strand as a template. One of skill would recognize that while chemical synthesis of DNA is limited to sequences of about 100 bases, longer sequences can be obtained by the ligation of shorter sequences.

Alternatively, subsequences can be cloned and the appropriate subsequences cleaved using appropriate restriction enzymes. The fragments can then be ligated to produce the desired DNA sequence.

In certain embodiments, DNA encoding targeted antimicrobial peptides may be cloned using DNA amplification methods such as polymerase chain reaction (PCR). Thus, for example, the nucleic acid encoding a targeting peptide is PCR amplified, using a sense primer containing the restriction site for NdeI and an antisense primer containing the restriction site for HindIII. This produces a nucleic acid encoding the targeting sequence and having terminal restriction sites. Similarly nucleic acids encoding an antimicrobial peptide and/or antimicrobial peptide/linker/spacer can be provided having complementary restriction sites. Ligation of sequences and insertion into a vector produces a vector encoding the fusion protein.

While the targeting peptides and AMPs can be directly joined together, one of skill will appreciate that they can be separated by a peptide spacer/linker consisting of one or more amino acids. Generally the spacer will have no specific biological activity other than to join the proteins or to preserve some minimum distance or other spatial relationship between them. However, the constituent amino acids of the spacer may be selected to influence some property of the molecule such as the folding, net charge, or hydrophobicity.

The nucleic acid sequences encoding the fusion proteins can be expressed in a variety of host cells, including *E. coli*, other bacterial hosts, yeast, and various higher eukaryotic cells such as the COS, CHO and HeLa cells lines and myeloma cell lines. The recombinant protein gene will be operably linked to appropriate expression control sequences for each host. For *E. coli* this includes a promoter such as the T7, trp, or lambda promoters, a ribosome binding site and preferably a transcription termination signal. For eukaryotic cells, the control sequences will include a promoter and preferably an enhancer derived from immunoglobulin genes, SV40, cytomegalovirus, etc., and a polyadenylation sequence, and may include splice donor and acceptor sequences.

The plasmids can be transferred into the chosen host cell by well-known methods such as calcium chloride transformation for *E. coli* and calcium phosphate treatment or electroporation for mammalian cells. Cells transformed by the plasmids can be selected by resistance to antibiotics conferred by genes contained on the plasmids, such as the amp, gpt, neo and hyg genes.

Once expressed, the recombinant fusion proteins can be purified according to standard procedures of the art, including ammonium sulfate precipitation, affinity columns, column chromatography, gel electrophoresis and the like (see, generally, R. Scopes (1982) *Protein Purification*, Springer-Verlag, N.Y.; Deutscher (1990)*Methods in Enzymology* Vol. 182: *Guide to Protein Purification.*, Academic Press, Inc. N.Y.). Substantially pure compositions of at least about 90 to 95% homogeneity are preferred, and 98 to 99% or more homogeneity are most preferred for pharmaceutical uses. Once purified, partially or to homogeneity as desired, the polypeptides may then be used therapeutically.

One of skill in the art would recognize that after chemical synthesis, biological expression, or purification, the fusion protein may possess a conformation substantially different than the native conformations of the constituent polypeptides. In this case, it may be necessary to denature and reduce the polypeptide and then to cause the polypeptide to re-fold into the preferred conformation. Methods of reducing and denaturing proteins and inducing re-folding are well known to those of skill in the art (See, Debinski et al. (1993) *J. Biol. Chem.*, 268: 14065-14070; Kreitman and Pastan (1993) *Bioconjug. Chem.*, 4: 581-585; and Buchner, et al. (1992)*Anal. Biochem.*, 205: 263-270).

One of skill would recognize that modifications can be made to the fusion proteins without diminishing their biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids placed on either terminus to create conveniently located restriction sites or termination codons.

As indicated above, in various embodiments an amino acid, or a peptide linker/spacer is used to join the one or more targeting peptides to one or more antimicrobial peptide(s). In various embodiments the peptide linker is relatively short, typically less than about 10 amino acids, preferably less than about 8 amino acids and more preferably about 1 or to or 3 to about 5 amino acids. Suitable illustrative linkers include, but are not limited to PSGSP ((SEQ ID NO:315), ASASA (SEQ ID NO: 316), or GGG. In certain embodiments longer linkers such as (GGGGS)$_3$ (SEQ ID NO:317) can be used. Illustrative linking amino acids and peptide linkers and other linkers are shown in Table 4.

TABLE 4

Illustrative peptide and non-peptide linkers.

| Linker | SEQ ID NO: |
|---|---|
| P | |
| S | |
| G | |
| AAA | |
| GGG | |
| SGG | |
| SAT | |
| PYP | |
| ASA | |
| GGGG | 318 |
| PSPSP | 319 |
| PSPSP | 320 |
| KKKK | 321 |
| RRRR | 322 |
| ASASA | 323 |
| GGSGGS | 324 |
| GGGGS | 325 |
| GGGGS GGGGS | 326 |
| GGGGS GGGGS GGGGS | 327 |
| GGGGS GGGGS GGGGS GGGGS | 328 |
| GGGGS GGGGS GGGGS GGGGS GGGGS | 329 |
| GGGGS GGGGS GGGGS GGGGS GGGGS GGGGS | 330 |
| 2-nitrobenzene or O-nitrobenzyl | |
| Nitropyridyl disulfide | |
| Dioleoylphosphatidylethanolamine (DOPE) | |
| S-acetylmercaptosuccinic acid | |
| 1, 4, 7, 10-tetraazacyclododecane-1, 4, 7, 10-tetracetic acid (DOTA) | |
| β-glucuronide and β-glucuronide variants | |
| Poly(alkylacrylic acid) | |

TABLE 4-continued

Illustrative peptide and non-peptide linkers.

| Linker | SEQ ID NO: |
|---|---|
| Benzene-based linkers (for example: 2,5-Bis(hexyloxy)-1,4-bis[2,5-bis(hexyloxy)-4-formyl-phenylenevinylene]benzene) and like molecules | |
| Disulfide linkages | |
| Poly(amidoamine) or like dendrimers linking multiple target and killing peptides in one molecule | |
| Carbon nanotubes | |
| Hydrazone and hydrazone variant linkers | |
| PEG of any chain length | |
| Succinate, formate, acetate butyrate, other like organic acids | |
| Aldols, alcohols, or enols | |
| Peroxides | |
| alkane or alkene groups of any chain length | |
| One or more porphyrin or dye molecules containing free amide and carboxylic acid groups | |
| One or more DNA or RNA nucleotides, including polyamine and polycarboxyl-containing variants | |
| Inulin, sucrose, glucose, or other single, di or polysaccharides | |
| Linoleic acid or other polyunsaturated fatty acids | |
| Variants of any of the above linkers containing halogen or thiol groups | |

(In various embodiments any of the amino-acid-based linkers could be L peptides, D peptides, combinations of L and D residues, β-peptides, and the like).

Multiple Targeting Peptides and/or AMPs.

As indicated above, in certain embodiments, the chimeric moieties described herein can comprise multiple targeting peptides attached to a single antimicrobial peptide or multiple antimicrobial peptides attached to a single targeting peptide, or multiple targeting peptides attached to multiple antimicrobial peptides.

Where the chimeric construct is a fusion protein this is easily accomplished by providing multiple domains that are targeting domains attached to one or more antimicrobial peptide domains. In various embodiments the multiple targeting domains and/or multiple effector domains can be attached to each other directly or can be separated by linkers (e.g., amino acid or peptide linkers as described above).

When the chimeric construct is a chemical conjugate linear or branched configurations are readily produced by using branched or multifunctional linkers and/or a plurality of different linkers.

Protecting Groups.

While the various peptides described herein may be shown with no protecting groups, in certain embodiments they can bear one, two, three, four, or more protecting groups. In various embodiments, the protecting groups can be coupled to the C- and/or N-terminus of the peptide(s) and/or to one or more internal residues comprising the peptide(s) (e.g., one or more R-groups on the constituent amino acids can be blocked). Thus, for example, in certain embodiments, any of the peptides described herein can bear, e.g., an acetyl group protecting the amino terminus and/or an amide group protecting the carboxyl terminus.

Methods of Use

Figure 6:
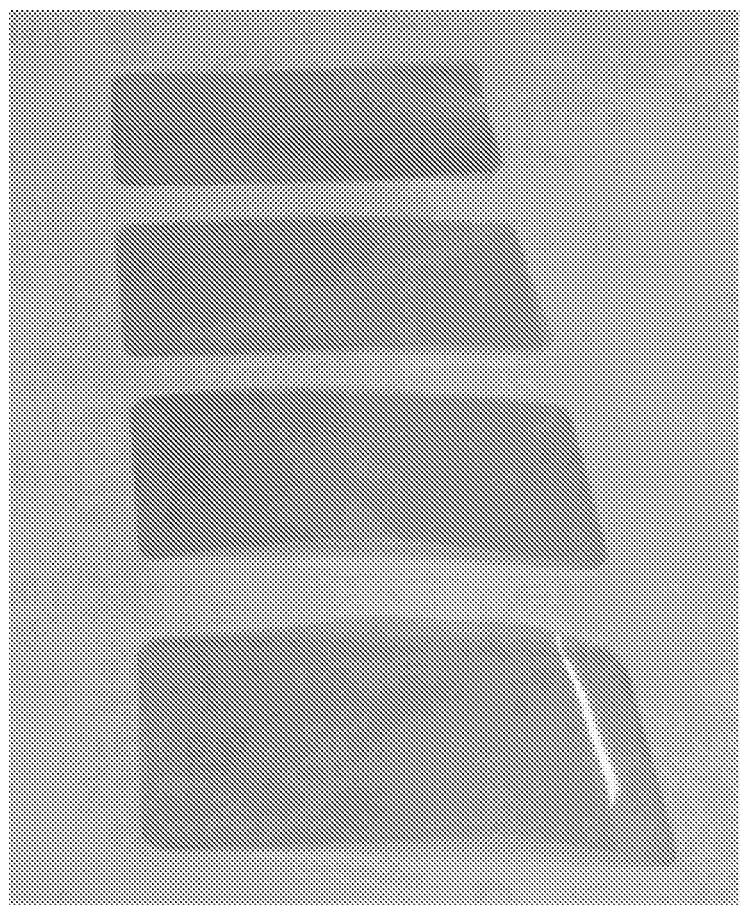
FIG. 6 illustrates a set of four dental strips sufficient to cover molars and bicuspids to ensure that the biological niche of *S. mutans* is treated.

In certain embodiments when using the dental strips described herein, the dental strip is applied to the desired oral surface by the wearer. The side of the dental strip bearing the delivery is contacted with the oral surface (e.g., the tooth surface) and the dental strip can be shaped by the user to form a continuous layer over a plurality of teeth. In certain embodiments the dental strips are applied to cover both molars and bicuspids. To facilitate such application, in certain embodiments the dental strips are provided in groups of four (see, e.g., FIG. 6 to facilitate such coverage.

The delivery layer(s) provide a vehicle for the STAMP(s) (and/or simple AMPs) as well as tackiness between the oral surfaces and the dental strip thereby holding the strip of material in place for extended periods of time. In certain embodiments the dental strip is used for a period of time ranging from about 1 minute or from about 2 minutes or from about 5 minutes, or from about 10 minutes up to about 1 hour, or up to about 45 minutes, or up to about 30 minutes, or up to about 20 minutes. In certain embodiments the dental strip is removed by the user after the desired period of time, while in other embodiments the dental strip simply dissolves over the required period of time.

After use there may be a residual amount of delivery layer material remaining on the tooth or gum surface. The amount of residual material is typically not great and can readily be removed by use of a swab, a tooth brush, or a rinse.

Kits.

In certain embodiments the kits are provided containing the STAMP (or AMP)-releasing dental strip(s) as described herein. In certain embodiments the kit contains four strips, to cover upper and lower molars and bicuspids. In various embodiments each strip is disposed in a sealed plastic or foil bag/container.

In addition, the kits optionally include labeling and/or instructional materials providing directions (i.e., protocols) for the use of the dental strips described herein. Certain instructional materials describe the use of the dental strips to therapeutically or prophylactically to inhibit or prevent infection and/or to inhibit the formation of dental caries. The instructional materials may also, optionally, application methods, counter indications, and the like.

While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention.

Example 1

STAMP-Releasing Dental Strips

C16G2 Strip Formulation

In certain embodiments STAMP-releasing dental strips are provided. In various embodiments such dental strips comprise and release the C16G2 STAMP. Without being bound to a theory, it is believed the dental strips described herein provide an effective dosage of C16G2 STAMP to the tooth surface than application using a gel system.

Thus, in certain embodiments a C16G2 strip drug product is manufactured for administration as a dental strip product. The dental strip typically utilizes GRAS or compendia excipients. In certain embodiments the C16G2 strip product can be provided in 4 sealed pouches (1 per quadrant) and each strip can be removed from a peal-able transfer backing prior to administration. The qualitative and qualitative compositions of illustrative dental strip products (delivery/adhesive layer(s)) are shown in Tables 5-7 below.

TABLE 5

Qualitative and quantitative composition of a 9.2 mg C16G2 delivery layer drug product.

| Component | Function | Amount per dose |
|---|---|---|
| C16G2 | Drug Substance | 9.2 mg* |
| Polyvinylpyrrolidone, K90 | Polymer | 94.7 mg |
| Sucralose, NF | Flavoring Agent | 3.2 mg |
| Cool Mint Flavor | Flavoring agent | 26.3 mg |
| FD&C Blue No. 1 | Coloring Agent | 0.1 mg |

NF = National Formulary,
*= Nominal peptide amount (corrected for peptide content in the drug substance)

TABLE 6

Qualitative and quantitative composition of an 18.4 mg C16G2 delivery layer drug product.

| Component | Function | Amount per dose |
|---|---|---|
| C16G2 | Drug Substance | 18.4 mg* |
| Polyvinylpyrrolidone, K90 | Polymer | 94.7 mg |
| Sucralose, NF | Flavoring Agent | 3.2 mg |
| Cool Mint Flavor | Flavoring agent | 26.3 mg |
| FD&C Blue No. 1 | Coloring Agent | 0.1 mg |

NF = National Formulary,
*= Nominal peptide amount (corrected for peptide content in the drug substance)

TABLE 7

Qualitative and quantitative composition of a 36.8 mg C16G2 delivery layer drug product.

| Component | Function | Amount per dose |
|---|---|---|
| C16G2 | Drug Substance | 36.8 mg* |
| Polyvinylpyrrolidone, K90 | Polymer | 95.7 mg |
| Sucralose, NF | Flavoring Agent | 3.7 mg |
| Cool Mint Flavor | Flavoring agent | 26.1 mg |
| FD&C Blue No. 1 | Coloring Agent | 0.1 mg |

NF = National Formulary,
*= Nominal peptide amount (corrected for peptide content in the drug substance)

Placebo Strip Formulation

In certain embodiments for evaluation purposes a placebo dental strip is formulated. Typically the placebo strip does not contain active ingredients. It utilizes generally recognized as safe (GRAS) or compendia excipients. To maintain a study blind, the Placebo product can also be provided in 4 sealed pouches and each strips can be removed from a pealable transfer backing prior to administration. In certain embodiments each strip contains the same excipients as the active strip, but the C16G2 is omitted.

Figure 7:
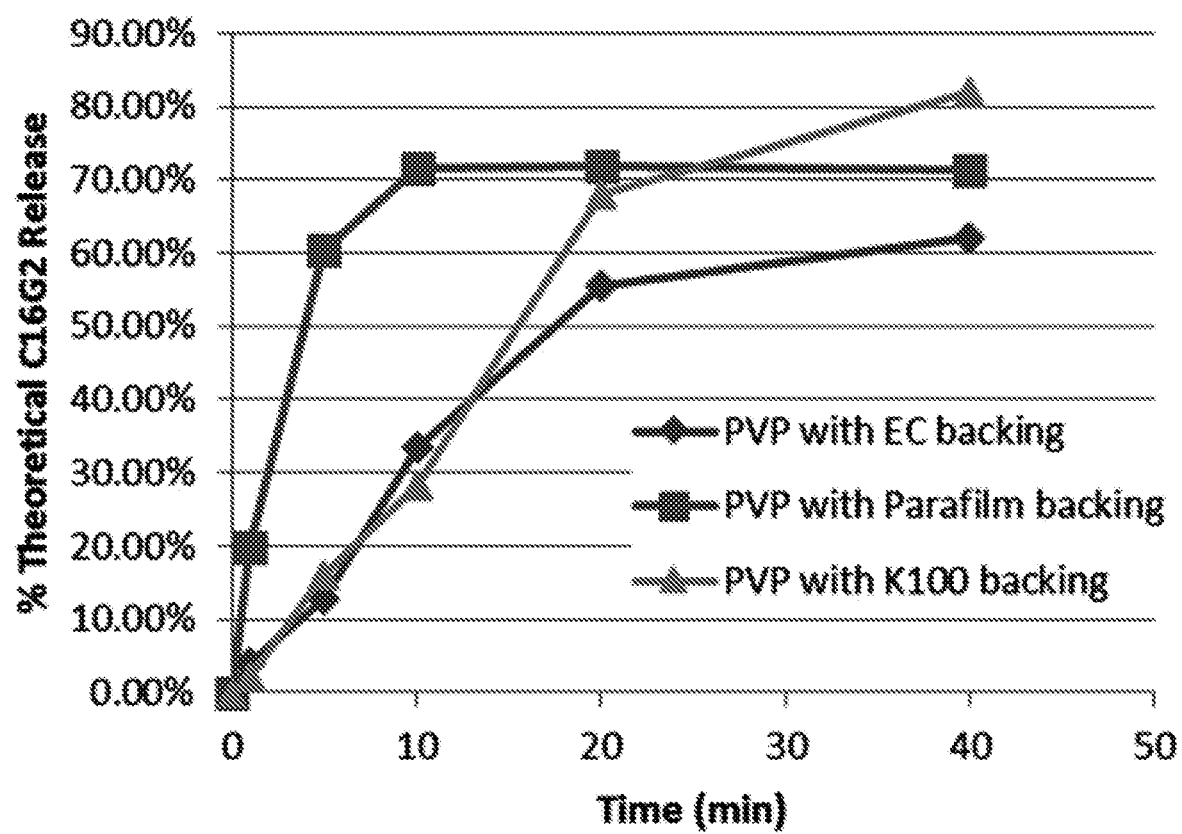
FIG. 7 illustrates rapid C16G2 percent release and total release from dental strips with a PVP delivery layer and various backing layers.

A comparison of total C16G2 and percent C16G2 release from dental strips and a varnish is shown in FIG. 7.

Illustrative Backing Layer.

In one illustrative, but non-limiting embodiments, the delivery layer described above, is provided on a backing layer comprising about 62.5% (w/w) ethylcellulose (with a viscosity of 90-110 mPa*s as a 5% solution in 80% toluene, 20% ethanol) and 37.5% (w/w) Castor oil.

Illustrative Release Liner.

In certain embodiments the delivery layer(s) described above, can be provided with or without a backing layer in combination with a release layer (e.g., a polyethylene terephthalate and polytetrafluoroethylene release liner).

The foregoing dental strip formulations are illustrative and not limiting. Using the teachings provided herein numerous other STAMP-releasing dental strips will be available to one of skill in the art. For example, 2 strips per pack could be constructed to cover ½ the mouth each, rather than one quadrant of the mouth per strip, where the amount of peptide and excipients could be doubled from those shown in Tables 5 to 7.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A dental strip for the delivery of effective amounts of specifically targeted antimicrobial peptides (STAMPs), said dental strip comprising:

an orally compatible backing layer; and a delivery layer disposed on one surface of said backing layer wherein said delivery layer comprises:

about 90 mg to 100 mg polyvinylpyrrolidone (K90);

about 5 mg up to about 80 mg of a specifically targeted antimicrobial peptide (STAMP) capable of binding and killing Streptococcus mutans;

about 3 mg up to about 4 mg sucralose as a first flavoring agent;

about 20 mg up to about 30 mg of a second flavoring agent other than sucralose; and a coloring agent;

wherein said delivery layer maintains the stability and activity of the STAMP and releases an effective amount of said STAMP when said dental strip is disposed against teeth in an oral cavity; and wherein said STAMP comprises a targeting peptide comprising an amino acid sequence selected from the group consisting of SGSLSTFFRLFNRSFTQALGK (SEQ ID NO:5), EMRLSKFFRDFILQRKK (SEQ ID NO:6), EMRISRIILDFLFLRKK (SEQ ID NO:7), NIFEYFLE (SEQ ID NO:8), TFFRLFNR (SEQ ID NO:9), TFFRLFNRS (SEQ ID NO:10), TFFRLFNRS (SEQ ID NO:11), TFFRLFNRSF (SEQ ID NO:12), TFFRLFNRSFT (SEQ ID NO:13), TFFRLFNRSFTQ (SEQ ID NO:14), TFFRLFNRSFTQA (SEQ ID NO:15), TFFRLFNRSFTQAL (SEQ ID NO:16), TFFRLFNRSFTQALG (SEQ ID NO:17), TFFRLFNRSFTQALGK (SEQ ID NO:18), STFFRLFNR (SEQ ID NO:19), STFFRLFNRS (SEQ ID NO:20), STFFRLFNRS (SEQ ID NO:21), STFFRLFNRSF (SEQ ID NO:22), STFFRLFNRSFT (SEQ ID NO:23), STFFRLFNRSFTQ (SEQ ID NO:24), STFFRLFNRSFTQA (SEQ ID NO:25), STFFRLFNRSFTQAL (SEQ ID NO:26), STFFRLFNRSFTQALG (SEQ ID NO:27), STFFRLFNRSFTQALGK (SEQ ID NO:28), LSTFFRLFNR (SEQ ID NO:29), LSTFFRLFNRS (SEQ ID NO:30), LSTFFRLFNRS (SEQ ID NO:31), LSTFFRLFNRSF (SEQ ID NO:32), LSTFFRLFNRSFT (SEQ ID NO:33), LSTFFRLFNRSFTQ (SEQ ID NO:34), LSTFFRLFNRSFTQA (SEQ ID NO:35), LSTFFRLFNRSFTQAL (SEQ ID NO:36), LSTFFRLFNRSFTQALG (SEQ ID NO:37), LSTFFRLFNRSFTQALGK (SEQ ID NO:38), SLSTFFRLFNR (SEQ ID NO:39), SLSTFFRLFNRS (SEQ ID NO:40), SLSTFFRLFNRS (SEQ ID NO:41), SLSTFFRLFNRSF (SEQ ID NO:42), SLSTFFRLFNRSFT (SEQ ID NO:43), SLSTFFRLFNRSFTQ (SEQ ID NO:44), SLSTFFRLFNRSFTQA (SEQ ID NO:45), SLSTFFRLFNRSFTQAL (SEQ ID NO:46), SLSTFFRLFNRSFTQALG (SEQ ID NO:47), SLSTFFRLFNRSFTQALGK (SEQ ID NO:48), GSLSTFFRLFNR (SEQ ID NO:49), GSLSTFFRLFNRS (SEQ ID NO:50), GSLSTFFRLFNRS (SEQ ID NO:51), GSLSTFFRLFNRSF (SEQ ID NO:52), GSLSTFFRLFNRSFT (SEQ ID NO:53), GSLSTFFRLFNRSFTQ (SEQ ID NO:54), GSLSTFFRLFNRSFTQA (SEQ ID NO:55), GSLSTFFRLFNRSFTQAL (SEQ ID NO:56), GSLSTFFRLFNRSFTQALG (SEQ ID NO:57), GSLSTFFRLFNRSFTQALGK (SEQ ID NO:58), SGSLSTFFRLFNR (SEQ ID NO:59), SGSLSTFFRLFNRS (SEQ ID NO:60), SGSLSTFFRLFNRS (SEQ ID NO:61), SGSLSTFFRLFNRSF (SEQ ID NO:62), SGSLSTFFRLFNRSFT (SEQ ID NO:63), SGSLSTFFRLFNRSFTQ (SEQ ID NO:64), SGSLSTFFRLFNRSFTQA (SEQ ID NO:65), SGSLSTFFRLFNRSFTQAL (SEQ ID NO:66), and SGSLSTFFRLFNRSFTQALG (SEQ ID NO:67), AFFRAFNRAFAQALAK (SEQ ID NO:70), TFFRAFARAFAQAAAK (SEQ ID NO:71), AFFRAFARAFAQALAK (SEQ ID NO:72), AFFRLFARAFAQAAAK (SEQ ID NO:73), TLFRLLNRSLTQALGK (SEQ ID NO:74), TFFRLFNRSFTQALFK (SEQ ID NO:75), TFFRLFNRSLTQALGK (SEQ ID NO:76), TFFRLFNRSFTQALNK (SEQ ID NO:77), AFFRAFARAFAQAAAK (SEQ ID NO:78), AFFRAFNRAFAQAAAK (SEQ ID NO:79), TFFRLFNRSFTQALSK (SEQ ID NO:80), AFFRAFARSFAQAAAK (SEQ ID NO:81), AFFRAFARAFAQAAGK (SEQ ID NO:82), AFFRAFARAFTQAAAK (SEQ ID NO:83), TFFRLFNRSFTQALGQ (SEQ ID NO:84), TFFRLLNRSFTQALGK (SEQ ID NO:85), TWFRLFNRSFTQALGK (SEQ ID NO:86), AFFRAFARAFAQAFAK (SEQ ID NO:87), TQFRLFNRSFTQALGK (SEQ ID NO:88), TFFRLFNRSFTQALDK (SEQ ID NO:89), TFFRLFNRSFTQALAK (SEQ ID NO:90), TFFRLFNRSFTQALGE (SEQ ID NO:91), TFFRLFSRSFTQALGK (SEQ ID NO:92), TFFRLFNRSFTQALGA (SEQ ID NO:93), TFFRLFDRSFTQALGK (SEQ ID NO:94), TFFRLFNRSFTQALGF (SEQ ID NO:95), TFFRAFARSFTQAAAK (SEQ ID NO:96), TFFRLFARSFTQAAGK (SEQ ID NO:97), TFFRLFNRSFTQ L K (SEQ ID NO:98), TFFRLFNRSFTQALGS (SEQ ID NO:99), TLFRLFNRSFTQALGK (SEQ ID NO:100), TFFRLNFRSFTQALGK (SEQ ID NO:101), TFFRLFNRSQTQALGK (SEQ ID NO:102), TFFRLFAAAFTQALGK (SEQ ID NO:103), TFFRLFNRSFTQALGK (SEQ ID NO:104), TFFRLFNRSAAAALGK (SEQ ID NO:105), TFFRLFFRSNTQALGK (SEQ ID NO:106), TFFRLFNRSFTQPLGK (SEQ ID NO:107), TAFRLANRSATQALGK (SEQ ID NO:108), TFFRLFNRSFTQAAAA (SEQ ID NO:109), TFFRLQNRSFTQALGK (SEQ ID NO:110), TFFRLFNRSFTQALPK (SEQ ID NO:111), TYYRLFNRSFTQALGK (SEQ ID NO:112), TFFRLF RSFTQALGK (SEQ ID NO:113), and TQFRLQNRSQTQALGK (SEQ ID NO:114) attached to an antimicrobial peptide comprising an amino acid sequence selected from the group consisting of KNLRIIRKGIHIIKKY (SEQ ID NO:4), GLGRVIGRLIKQIIWRR (SEQ ID NO:123), VYRKRKSILKIYAKLKGWH (SEQ ID NO:124), NYRLVNAIFSKIFKKKFIKF (SEQ ID NO:125), KILKFLFKKVF (SEQ ID NO:126), FIRKFLKKWLL (SEQ ID NO:127), KLFKFLRKHLL (SEQ ID NO:128), KILKFLFKQVF (SEQ ID NO:129), KILKKLFKFVF (SEQ ID NO:130), GILKKLFTKVF (SEQ ID NO:131), LRKFLHKLF (SEQ ID NO:132), LRKNLRWLF (SEQ ID NO:133), FIRKFLQKLHL (SEQ ID NO:134), FTRKFLKFLHL (SEQ ID NO:135), KKFKKFKVLKIL (SEQ ID NO:136), LLKLLKLKKLKF (SEQ ID NO:137), FLKFLKKFFKKLKY (SEQ ID NO:138), GWLKMFKKIIGKFGKF (SEQ ID NO:139), GIFKKFVKILYKVQKL (SEQ ID NO:140), YIQFHLNQQPRPKVKKIKIFL (SEQ ID NO:142), FESKILNASKELDKEKKVNTALSFNSHQDFAKAYQNGKI (SEQ ID NO:145), and WSRVPGHSDTGWKVWHRW (SEQ ID NO:146).

2. The dental strip of claim 1, wherein:
said delivery layer is distributed on said backing layer as a plurality of dots or regions; or
said delivery layer is distributed on said backing layer as a substantially continuous layer.

3. The dental strip of claim 1, wherein said delivery layer ranges in thickness from about 20 μm up to about 500 μm.

4. The dental strip of claim 1, wherein:
said dental strip, when applied to a tooth surface delivers sufficient specifically targeted antimicrobial peptide to kill or to inhibit the growth and/or proliferation of S. mutans on said tooth surface and/or adjacent gums; and/or
said delivery layer is provided on said strip in a substantially dry form or the orally compatible polymer comprising said delivery layer is hydratable and/or dissolvable in the mouth; and/or
said orally compatible polymer dissolves over a period of time ranging from about 1 minute or from about 2 minutes or from about 5 minutes, or from about 10 minutes up to about 1 hour, or up to about 45 minutes, or up to about 30 minutes, or up to about 20 minutes.

5. The dental strip of claim 1, wherein:
said backing layer comprises one or more materials selected from the group consisting of hydroxypropylmethylcellulose, hydroxypropylcellulose, hydroxyethylcellulose, and polyethylene glycol; or
said backing layer is water impermeable; or
said backing layer comprises a material selected from the group consisting of ethyl cellulose, propyl cellulose, polyethylene, polypropylene, polyolefin, polyurethane, polyethylene terephthalate, polylactic acid, polyacrylates, and ethylene vinyl acetate.

6. The dental strip of claim 1, wherein a release liner film is disposed on said delivery layer.

7. The dental strip of claim 6, wherein:
said release liner can be peeled from the underlying delivery layer without substantially removing said delivery layer from said backing layer; and/or
said release liner comprises a material selected from the group consisting of polyethylene, polypropylene, various polyurethanes, polyethylene terephthalate, polytetrafluoroethylene, polysiloxanes, and combinations thereof; and/or
said release liner comprises a polyethylene terephthalate and polytetrafluoroethylene film; and/or
said release liner ranges in thickness from about 10 μm to about 200 μm, or about 25 μm to about 100 μm, or about 80 μm.

8. The dental strip of claim 1, wherein said dental strip comprises about 25 mg to about 30 mg of said second flavoring agent.

9. The dental strip of claim 8, wherein said backing layer comprises ethylcellulose with a viscosity of 90 to 110 mPa as a 5% solution in 80% toluene, 20% ethanol.

10. The dental strip of claim 1, wherein the delivery layer comprises a formulation selected from the group consisting of:

| Component | Function | Amount per Strip |
|---|---|---|
| Specifically targeted antimicrobial peptide | Active Agent | 9.2 mg |
| Polyvinylpyrrolidone, K90 | Polymer | 94.7 mg |
| Sucralose, NF | Flavoring Agent | 3.2 mg |
| Cool Mint Flavor | Flavoring agent | 26.3 mg |
| FD&C Blue No. 1 | Coloring Agent | 0.1 mg, |

| Component | Function | Strip |
|---|---|---|
| Specifically targeted antimicrobial peptide | Active Agent | 18.4 mg |
| Polyvinylpyrrolidone, K90 | Polymer | 94.7 mg |
| Sucralose, NF | Flavoring Agent | 3.2 mg |
| Cool Mint Flavor | Flavoring agent | 26.3 mg |
| FD&C Blue No. 1 | Coloring Agent | 0.1 mg, | and

| Component | Function | Amount per strip |
|---|---|---|
| Specifically targeted antimicrobial peptide | Active Agent | 36.8 mg |

-continued

| Component | Function | Amount per strip |
|---|---|---|
| Polyvinylpyrrolidone, K90 | Polymer | 95.7 mg |
| Sucralose, NF | Flavoring Agent | 3.7 mg |
| Cool Mint Flavor | Flavoring agent | 26.1 mg |
| FD&C Blue No. 1 | Coloring Agent | 0.1 mg. |

11. The dental strip of claim 1, wherein:
the amino acid sequence of said targeting peptide consists of the sequence TFFRLFNRSFTQALGK (SEQ ID NO:104); and
the amino acid sequence of said antimicrobial peptide consists of the sequence KNLRIIRKGIHIIKKY (SEQ ID NO:4).

12. The dental strip of claim 1, wherein:
said dental strip contains a fluoride; and/or
said dental strip comprises a fluoride disposed in said delivery layer; and/or
said dental strip comprises a fluoride selected from the group consisting of sodium fluoride, stannous fluoride, sodium monofluorophosphate, zinc hexafluorosilicate, sodium hexafluorosilicate, ammonium fluoride, calcium fluoro-phosphate ($Ca_5[F(PO_4)_3]$) or fluorapatite, fluorine-doped hydroxyapatite, calcium fluoride ($CaF_2$) or fluorite or fluorspar, diofluorisilane, $TiF_4$, and acidulated fluoride; and/or
said dental strip additionally contains a positively charged compound that is antimicrobial and/or that promotes remineralization; and/or
said dental strip contains a compound selected from the group consisting of cetylpyridinium chloride, benzalkonium chloride, chlorhexidine, polyhexamethylene biguanide (PHMB), cationic antimicrobial nanoparticles, bleach, synthetic peptides comprising a single DSS or ESS or repeats of DSS or ESS, dentin-sialophosphoprotein (DSP), dentin phosphoprotein, Arg-calcium carbonate, and xylitol.

13. A method of reducing or preventing the formation of dental caries disease in a mammal, said method comprising applying a dental strip of claim 1 to the teeth of said mammal.

14. A kit comprising:
a container containing a dental strip of claim 1.

* * * * *